US012575323B2

(12) United States Patent
Lui et al.

(10) Patent No.: US 12,575,323 B2
(45) Date of Patent: Mar. 10, 2026

(54) COMPOUND FOR ORGANIC OPTOELECTRONIC DIODE, COMPOSITION FOR ORGANIC OPTOELECTRONIC DIODE, ORGANIC OPTOELECTRONIC DIODE, AND DISPLAY DEVICE

(71) Applicant: SAMSUNG SDI CO., LTD., Yongin-si (KR)

(72) Inventors: Jinhyun Lui, Suwon-si (KR); Dong Min Kang, Suwon-si (KR); Dong Wan Ryu, Suwon-si (KR); Ho Kuk Jung, Suwon-si (KR); Sangshin Lee, Suwon-si (KR); Jaehoon Kim, Suwon-si (KR); Changwoo Kim, Suwon-si (KR); Chang Ju Shin, Suwon-si (KR); Namheon Lee, Suwon-si (KR); Sung-Hyun Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 1107 days.

(21) Appl. No.: 17/622,415

(22) PCT Filed: Jun. 26, 2020

(86) PCT No.: PCT/KR2020/008390
§ 371 (c)(1),
(2) Date: Dec. 23, 2021

(87) PCT Pub. No.: WO2020/263029
PCT Pub. Date: Dec. 30, 2020

(65) Prior Publication Data

US 2022/0384738 A1 Dec. 1, 2022

(30) Foreign Application Priority Data

Jun. 28, 2019 (KR) ........................ 10-2019-0078081
Jun. 25, 2020 (KR) ........................ 10-2020-0078023

(51) Int. Cl.
*H10K 85/60* (2023.01)
*C07D 405/04* (2006.01)
(Continued)

(52) U.S. Cl.
CPC ....... *H10K 85/6574* (2023.02); *C07D 405/04* (2013.01); *C07D 487/04* (2013.01);
(Continued)

(58) Field of Classification Search
CPC ............. H01L 51/0073; H01L 51/0067; H01L 51/0052; H01L 51/0072; H01L 51/5016; C07D 405/04; C07D 487/04; C09K 11/06
See application file for complete search history.

(56) References Cited

U.S. PATENT DOCUMENTS 11,495,747 B2 * 11/2022 Lee ........................ H05B 33/20
2014/0001456 A1 1/2014 Mizutani et al.
(Continued)

FOREIGN PATENT DOCUMENTS

CN 109265450 A 1/2019
EP 3 670 510 A2 6/2020
(Continued)

OTHER PUBLICATIONS

Machine-generated English-language translation of WO-2020130394-A1.*

(Continued)

*Primary Examiner* — Vu A Nguyen
(74) *Attorney, Agent, or Firm* — Lee IP Law, P.C.

(57) ABSTRACT a compound for an organic optoelectronic device represented by a combination of Chemical Formula 1 and 2, a composition for an organic optoelectronic device including the same, an organic optoelectronic device, and a display device.

(Continued)

100

Details of Chemical Formulas 1 and 2 are as described in the specification.

6 Claims, 1 Drawing Sheet

(51) Int. Cl.

| | |
|---|---|
| ***C07D 487/04*** | (2006.01) |
| ***C09K 11/06*** | (2006.01) |
| ***H10K 50/11*** | (2023.01) |
| ***H10K 101/00*** | (2023.01) |
| ***H10K 101/10*** | (2023.01) |

(52) U.S. Cl.
CPC ............ *C09K 11/06* (2013.01); *H10K 85/615* (2023.02); *H10K 85/654* (2023.02); *H10K 85/6572* (2023.02); *C09K 2211/1018* (2013.01); *H10K 50/11* (2023.02); *H10K 2101/10* (2023.02); *H10K 2101/90* (2023.02)

(56) References Cited

U.S. PATENT DOCUMENTS

| | | | | |
|---|---|---|---|---|
| 2016/0072073 | A1 | 3/2016 | Lee et al. | |
| 2016/0079546 | A1 | 3/2016 | Park et al. | |
| 2019/0198780 | A1* | 6/2019 | Kim | H10K 85/6576 |
| 2022/0037594 | A1* | 2/2022 | Lee | C07D 209/86 |

FOREIGN PATENT DOCUMENTS

| | | | | |
|---|---|---|---|---|
| EP | 3 904 353 | A1 | 11/2021 | |
| JP | 6335288 | B2 | 5/2018 | |
| KR | 10-2012-0104067 | A | 9/2012 | |
| KR | 10-2016-0041822 | A | 4/2016 | |
| KR | 10-2016-0115626 | A | 10/2016 | |
| KR | 10-2017-0107919 | A | 9/2017 | |
| KR | 10-1814875 | B1 | 1/2018 | |
| KR | 10-2018-0038834 | A | 4/2018 | |
| KR | 10-2018-0040296 | A | 4/2018 | |
| KR | 10-1847347 | B1 | 4/2018 | |
| KR | 10-2018-0049266 | A | 5/2018 | |
| KR | 10-2018-0076358 | A | 7/2018 | |
| KR | 10-2018-0099436 | A | 9/2018 | |
| KR | 10-2019-0002206 | A | 1/2019 | |
| KR | 10-2019-0006448 | A | 1/2019 | |
| KR | 10-2019-0013353 | A | 2/2019 | |
| KR | 10-2019-0038246 | A | 4/2019 | |
| KR | 10-2019-0043898 | A | 4/2019 | |
| KR | 10-2021294 | B1 | 9/2019 | |
| KR | 10-2020-0070462 | A | 6/2020 | |
| KR | 10-2020-0077203 | A | 6/2020 | |
| KR | 10-2020-0077371 | A | 6/2020 | |
| KR | 10-2020-0081300 | A | 7/2020 | |
| KR | 10-2020-0145198 | A | 12/2020 | |
| KR | 10-2022-0002192 | A | 1/2022 | |
| TW | I541232 | B | 7/2016 | |
| TW | I543232 | B | 7/2016 | |
| WO | WO 2013/077352 | A1 | 5/2013 | |
| WO | WO 2019-027212 | A1 | 2/2019 | |
| WO | WO 2019-066250 | A1 | 4/2019 | |
| WO | WO-2020130389 | A1 * | 6/2020 | H10K 85/657 |
| WO | WO-2020130394 | A1 * | 6/2020 | C09K 11/06 |

OTHER PUBLICATIONS

Machine-generated English-language translation of WO-2020130389-A1.*
European Third Party Notification dated Jan. 23, 2023.
European Search Report dated Jun. 16, 2023, of the corresponding European Patent Application No. 20833191.8.
International Search Report dated Oct. 12, 2020 for PCT/KR2020/008390.

* cited by examiner

【Figure 1】
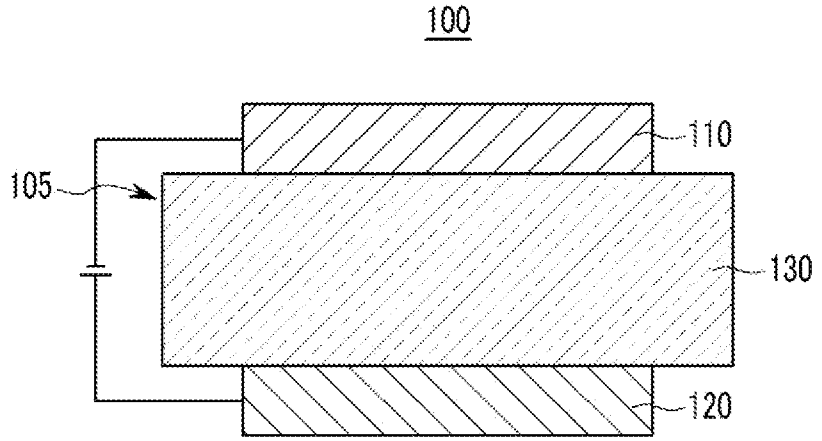
【Figure 2】
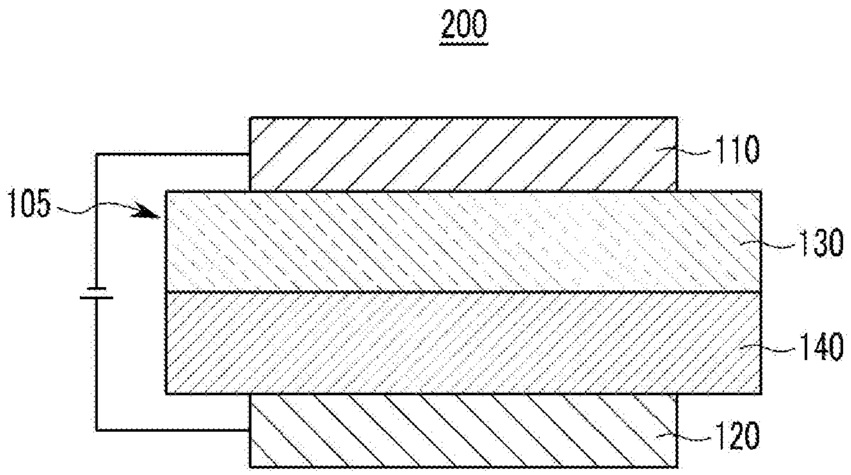

COMPOUND FOR ORGANIC OPTOELECTRONIC DIODE, COMPOSITION FOR ORGANIC OPTOELECTRONIC DIODE, ORGANIC OPTOELECTRONIC DIODE, AND DISPLAY DEVICE

CROSS REFERENCE TO RELATED APPLICATIONS

This is the U.S. national phase application based on PCT Application No. PCT/KR2020/008390, filed Jun. 26, 2020, which is based on Korean Patent Application No. 10-2019-0078081, filed Jun. 28, 2019, and Korean Patent Application No. 10-2020-0078023, filed Jun. 25, 2020, the entire contents of all of which are hereby incorporated by reference.

TECHNICAL FIELD

A compound for an organic optoelectronic device, a composition for an organic optoelectronic device, an organic optoelectronic device, and a display device are disclosed. It relates to a compound for an organic optoelectronic device, a composition for an organic optoelectronic device, an organic optoelectronic device and a display device.

BACKGROUND ART

An organic optoelectronic device (organic optoelectronic diode) is a device that converts electrical energy into photoenergy, and vice versa.

An organic optoelectronic device may be classified as follows in accordance with its driving principles. One is a photoelectric diode where excitons are generated by photoenergy, separated into electrons and holes, and are transferred to different electrodes to generate electrical energy, and the other is a light emitting diode where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and performance of an organic light emitting diode may be affected by organic materials disposed between electrodes.

DISCLOSURE

Technical Problem

An embodiment provides a compound for an organic optoelectronic device capable of realizing an organic optoelectronic device having high efficiency and a long life-span.

Another embodiment provides a composition for an organic optoelectronic device including the compound for an organic optoelectronic device.

Another embodiment provides an organic optoelectronic device including the compound for an organic optoelectronic device or the composition for an organic optoelectronic device.

Another embodiment provides a display device including the organic optoelectronic device.

Technical Solution

According to an embodiment, a compound for an organic optoelectronic device represented by a combination of Chemical Formula 1 and Chemical Formula 2 is provided.

[Chemical Formula 1]

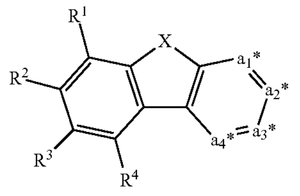

[Chemical Formula 2]

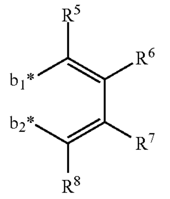

In Chemical Formula 1 and Chemical Formula 2,

X is O or S, adjacent two of $a_1$* to $a_4$* are independently linking carbon linked to $b_1$* and $b_2$*, respectively, $b_1$* and $b_2$* are independently linking carbon, the rest of $a_1$* to $a_4$* not linked to $b_1$* and $b_2$* are independently C—$R^a$, $R^a$ and $R^1$ to $R^8$ are independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^a$ and $R^1$ to $R^8$ is a group represented by Chemical Formula A,

[Chemical Formula A]

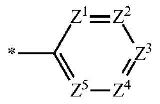

wherein, in Chemical Formula A, $Z^1$ to $Z^5$ are independently N or C—$R^b$, at least one of $Z^1$ to $Z^5$ is N, $R^b$ is independently hydrogen, deuterium, a substituted or unsubstituted C1 to C20 alkyl group, a substituted or unsubstituted C6 to C30 aryl group, or a combination thereof, $R^1$ to $R^4$ and $R^b$ are independently present or adjacent groups thereof are linked to form a substituted or unsubstituted aliphatic monocyclic ring, a substituted or unsubstituted aliphatic polycyclic ring, a substituted or unsubstituted aromatic monocyclic ring, a substituted or unsubstituted aromatic polycyclic ring, a substituted or unsubstituted heteroaromatic monocyclic ring, or a substituted or unsubstituted heteroaromatic polycyclic ring, and the "substituted" refers to replacement of at least one hydrogen by deuterium, a cyano group, a C1 to C10 alkyl group, or a C6 to C20 aryl group.

According to another embodiment, a composition for an organic optoelectronic device includes a first compound for an organic optoelectronic device including the aforementioned compound for an organic optoelectronic device, and a second compound for an organic optoelectronic device represented by Chemical Formula 3; or a combination of Chemical Formula 4 and Chemical Formula 5.

[Chemical Formula 3]

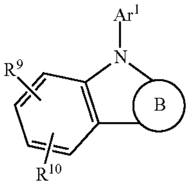

In Chemical Formula 3, $Ar^1$ is a substituted or unsubstituted C6 to C30 aryl group, a substituted or unsubstituted C2 to C30 heterocyclic group, or a combination thereof, and cyclic B is represented by Chemical Formula B-1 or Chemical Formula B-2,

[Chemical Formula B-1]

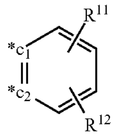

[Chemical Formula B-2]

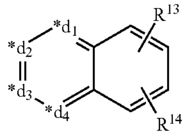

$C_1$ and $*C_2$ of Chemical Formula B-1 are independently linking carbon, adjacent two of $*d_1$ to $*d_4$ in Chemical Formula B-2 are independently linking carbon, and the other two that are not linked are independently C—$R^d$, $R^d$ and $R^9$ and $R^{14}$ are independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^d$ and $R^9$ and $R^{14}$ is a group represented by Chemical Formula C,

[Chemical Formula C]

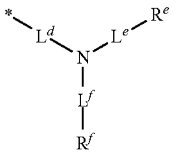

wherein, in Chemical Formula C, $L^d$ to $L^f$ are independently a single bond, or a substituted or unsubstituted C6 to C20 arylene group, $R^e$ and $R^f$ are independently a substituted or unsubstituted C6 to C30 aryl group, a substituted or unsubstituted C2 to C30 heterocyclic group, or a combination thereof, and

* is a linking point;

[Chemical Formula 4]

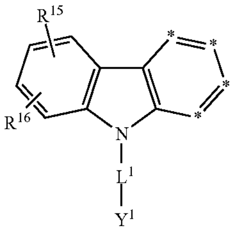

[Chemical Formula 5]

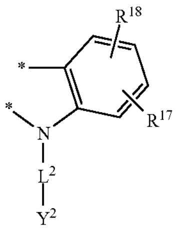

wherein, in Chemical Formula 4 and Chemical Formula 5, $Y^1$ and $Y^2$ are independently a substituted or unsubstituted C6 to C20 aryl group, or a substituted or unsubstituted C2 to C30 heterocyclic group, two adjacent *'s of Chemical Formula 4 are linked to Chemical Formula 5,

*'s of Chemical Formula 4 not linked to Chemical Formula 5 are independently C-$L^g$-$R^g$, $L^g$, $L^1$, and $L^2$ are independently a single bond, or a substituted or unsubstituted C6 to C20 arylene group, and $R^g$ and $R^{15}$ to $R^{18}$ are independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group.

According to another embodiment, an organic optoelectronic device includes an anode and a cathode facing each other, and at least one organic layer disposed between the anode and the cathode, wherein the organic layer includes the compound for an organic optoelectronic device or composition for an organic optoelectronic device.

According to another embodiment, a display device including the organic optoelectronic device is provided.

Advantageous Effects

An organic optoelectronic device having high efficiency and a long life-span may be realized.

DESCRIPTION OF THE DRAWINGS

FIGS. 1 and 2 are cross-sectional views showing organic light emitting diodes according to embodiments.

BEST MODE

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a cyano group, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, or a combination thereof.

In one example of the present invention, the "substituted" refers to replacement of at least one hydrogen of a substituent or a compound by deuterium, a cyano group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, the "substituted" refers to replacement of at least one hydrogen of a substituent or a compound by deuterium, a cyano group, a C1 to C20 alkyl group, or a C6 to C30 aryl group. In addition, specific examples of the present invention, the "substituted" refers to replacement of at least one hydrogen of a substituent or a compound by deuterium, a cyano group, a C1 to C5 alkyl group, or a C6 to C18 aryl group. In addition, specific examples of the present invention, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

In the present specification "adjacent groups thereof are linked to each other to form a substituted or unsubstituted aliphatic monocyclic ring, a substituted or unsubstituted aliphatic polycyclic ring, a substituted or unsubstituted aromatic monocyclic ring, a substituted or unsubstituted aromatic polycyclic ring, a substituted or unsubstituted heteroaromatic monocyclic ring, or a substituted or unsubstituted heteroaromatic polycyclic ring" means that adjacent groups are linked to each other to form a substituted or unsubstituted aliphatic monocyclic ring or a substituted or unsubstituted aliphatic polycyclic ring, adjacent groups are linked to each other to form a substituted or unsubstituted aromatic monocyclic ring or a substituted or unsubstituted aromatic polycyclic ring, a substituted or unsubstituted heteroaromatic monocyclic ring, or a substituted or unsubstituted heteroaromatic polycyclic ring, and for example means that any two adjacent substituents directly substituted on an aromatic ring or a heteroaromatic ring are linked to each other to form an additional ring.

For example, when two adjacent groups of $Z^1$ to $Z^5$ in Chemical Formula A in the present specification are each C—$R^b$, adjacent $R^b$'s may be linked to each other to form a substituted or unsubstituted aliphatic monocyclic ring, a substituted or unsubstituted aliphatic polycyclic ring, a substituted or unsubstituted aromatic monocyclic ring, a substituted or unsubstituted aromatic polycyclic ring, a substituted or unsubstituted heteroaromatic monocyclic ring, or a substituted or unsubstituted heteroaromatic polycyclic ring.

In an embodiment, adjacent $R^b$'s are linked to each other to form a substituted or unsubstituted aromatic monocyclic additional ring, and thereby Chemical Formula A may be a substituted or unsubstituted quinolinyl group, a substituted or unsubstituted isoquinolinyl group, or a substituted or unsubstituted It may be a substituted quinazolinyl group.

In another embodiment, adjacent $R^b$'s may be linked to each other to form a substituted or unsubstituted aromatic polycyclic additional ring, and thereby Chemical Formula A may be a substituted or unsubstituted benzoquinazolinyl group.

In another embodiment, adjacent $R^b$'s may be linked to each other to form a substituted or unsubstituted heteroaromatic polycyclic additional ring and thereby Chemical Formula A may be a substituted or unsubstituted benzofuranpyrimidinyl group, or a substituted or unsubstituted benzothiophenepyrimidinyl group.

In the present specification when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but is not limited thereto.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoquinazolinyl group, a substituted or unsubstituted benzofuranpyrimidinyl group, a substituted or unsubstituted benzothiophenepyrimidinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but is not limited thereto.

In the specification, hole characteristics refer to an ability to donate an electron to form a hole when an electric field is applied and that a hole formed in the anode may be easily injected into the light emitting layer, and a hole formed in a light emitting layer may be easily transported into an anode and transported in the light emitting layer due to conductive characteristics according to a highest occupied molecular orbital (HOMO) level.

In addition, electron characteristics refer to an ability to accept an electron when an electric field is applied and that an electron formed in a cathode may be easily injected into the light emitting layer, and an electron formed in a light emitting layer may be easily transported into a cathode and transported in the light emitting layer due to conductive characteristics according to a lowest unoccupied molecular orbital (LUMO) level.

A compound for an organic optoelectronic device according to an embodiment may be represented by a combination of Chemical Formula 1 and Chemical Formula 2.

[Chemical Formula 1]

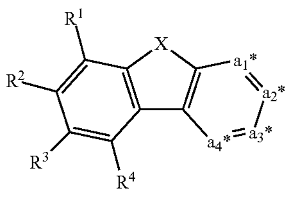

[Chemical Formula 2]

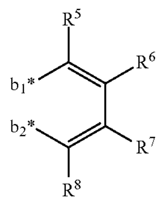

In Chemical Formula 1 and Chemical Formula 2,

X is O or S, adjacent two of $a_1$* to $a_4$* are independently linking carbon linked to $b_1$* and $b_{2*}$, $b_1$* and $b_2$* are independently linking carbon, the rest of $a_1$* to $a_4$* not linked to $b_1$* and $b_2$* are independently C—$R^a$, $R^a$ and $R^1$ to $R^8$ are independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^a$ and $R^1$ to $R^8$ is a group represented by Chemical Formula A,

[Chemical Formula A]

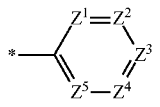

wherein, in Chemical Formula A, $Z^1$ to $Z^5$ are independently N or C—$R^b$, at least one of $Z^1$ to $Z^5$ is N, $R^b$ is independently hydrogen, deuterium, a substituted or unsubstituted C1 to C20 alkyl group, a substituted or unsubstituted C6 to C30 aryl group, or a combination thereof, $R^1$ to $R^4$ and $R^b$ are independently present or adjacent groups thereof are linked to form a substituted or unsubstituted aliphatic monocyclic ring, a substituted or unsubstituted aliphatic polycyclic ring, a substituted or unsubstituted aromatic monocyclic ring, a substituted or unsubstituted aromatic polycyclic ring, a substituted or unsubstituted heteroaromatic monocyclic ring, or a substituted or unsubstituted heteroaromatic polycyclic ring, and the "substituted" refers to replacement of at least one hydrogen by deuterium, a cyano group, a C1 to C10 alkyl group, or a C6 to C20 aryl group.

The compound for an organic optoelectronic device represented by the combination of Chemical Formula 1 and Chemical Formula 2 has a structure in which a substituent represented by Chemical Formula A is directly linked to additionally fusing dibenzofuran (or dibenzothiophene).

The compound having the additionally fused structure is desirable in expanding HOMO phore and stabilizing T1 energy levels, and as a result, the organic light emitting device to which the compound is applied may realize long life-span characteristics.

In addition, the compound has fast electron transport characteristics by directly substituting (without a linking group) the additionally fused structure with the substituent represented by Chemical Formula A, and this compound is applied. The organic light emitting device is advantageous for realizing low driving characteristics.

That is, by applying the compound represented by the combination of Chemical Formula 1 and Chemical Formula 2, it is possible to implement an organic light emitting device having low driving and long life-span characteristics.

For example, it may be represented by one of Chemical Formula 1-1 to Chemical Formula 1-9, depending on a fusion point of Chemical Formula 1 and Chemical Formula 2.

[Chemical Formula 1-1]

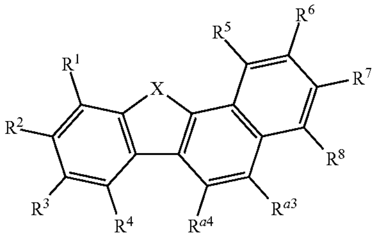

[Chemical Formula 1-2]

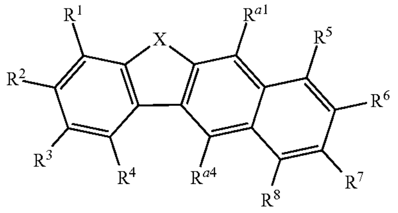

[Chemical Formula 1-3]

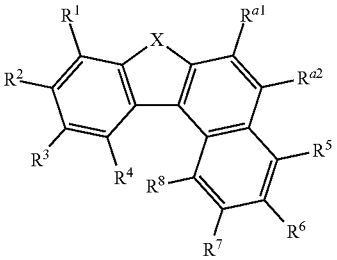

[Chemical Formula 1-4]

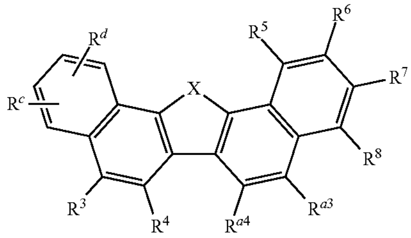

[Chemical Formula 1-5]

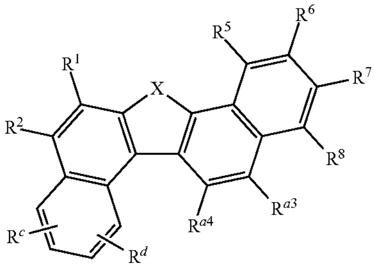

[Chemical Formula 1-6]

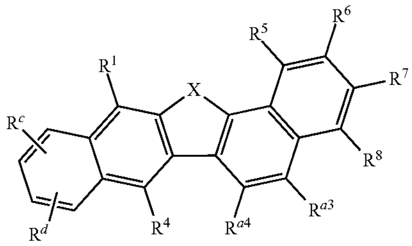

-continued

[Chemical Formula 1-7]

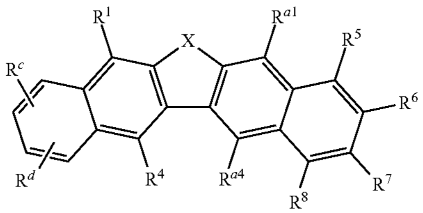

[Chemical Formula 1-8]

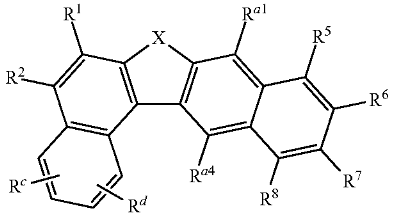

[Chemical Formula 1-9]

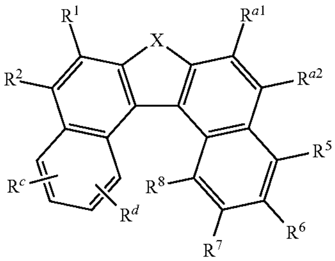

In Chemical Formula 1-1 to Chemical Formula 1-9, X and $R^1$ to $R^8$ are as described above, and $R^c$, $R^d$, and $R^{a1}$ to $R^{a4}$ are as defined for $R^1$ to $R^8$ described above.

As a specific example, it may be represented by Chemical Formula 1-1 or Chemical Formula 1-3, and in this case, a T1 energy level suitable for a phosphorescent host may be implemented, thereby showing a more advantageous effect.

For example, the compound for an organic optoelectronic device according to a specific substitution position of the group represented by Chemical Formula A may be represented by a combination of Chemical Formula 2 and one of Chemical Formula 1a to Chemical Formula 1d.

[Chemical Formula 1a]

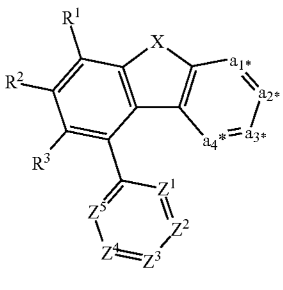

-continued

[Chemical Formula 1b]

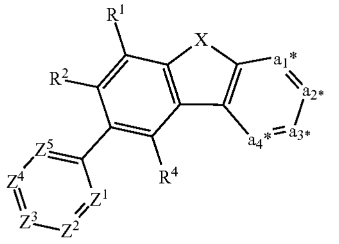

[Chemical Formula 1c]

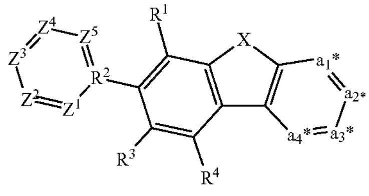

[Chemical Formula 1d]

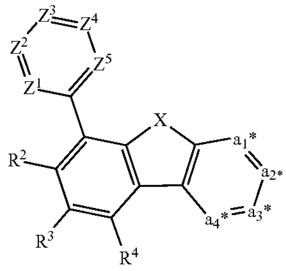

In Chemical Formula 1a to Chemical Formula 1d, X, $R^1$ to $R^4$, $a_1$* to $a_4$* and $Z^1$ to $Z^5$ are the same as described above.

Specifically, one of Chemical Formula 1a to Chemical Formula 1d combined with Chemical Formula 2 may be represented by one of Chemical Formula 1a-2-1 to Chemical Formula 1d-2-1, Chemical Formula 1a-2-2 to Chemical Formula 1d-2-2, Chemical Formula 1a-2-3 to Chemical Formula 1d-2-3, Chemical Formula 1a-2-4, Chemical Formula 1b-2-4, Chemical Formula 1a-2-5, Chemical Formula 1b-2-5, Chemical Formula 1a-2-6, Chemical Formula 1b-2-6, Chemical Formula 1a-2-7, Chemical Formula 1b-2-7, Chemical Formula 1a-2-8, and Chemical Formula 1b-2-8.

[Chemical Formula 1a-2-1]

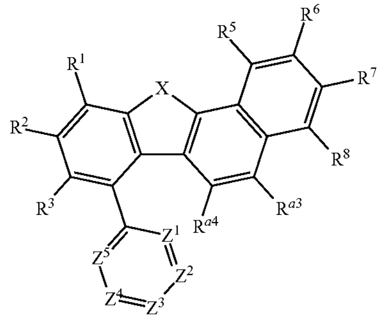

-continued

[Chemical Formula 1b-2-1]

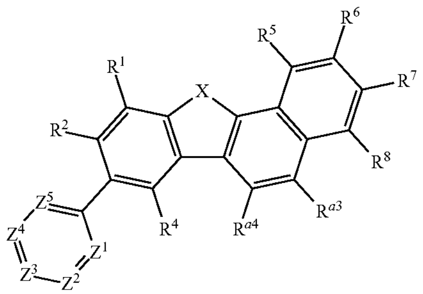

[Chemical Formula 1c-2-1]

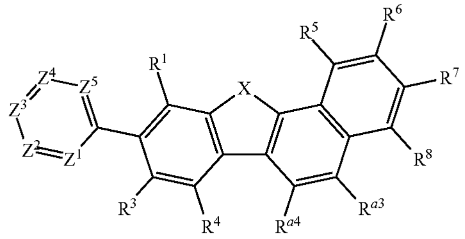

[Chemical Formula 1d-2-1]

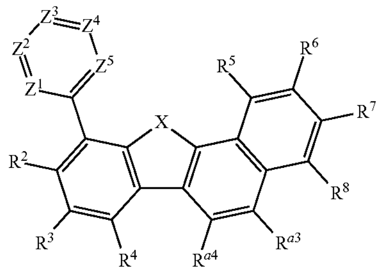

[Chemical Formula 1a-2-2]

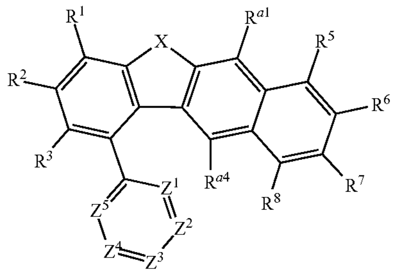

[Chemical Formula 1b-2-2]

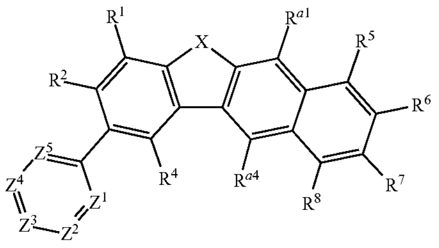

-continued
[Chemical Formula 1c-2-2]
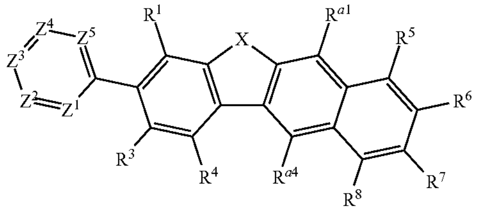
[Chemical Formula 1d-2-2]
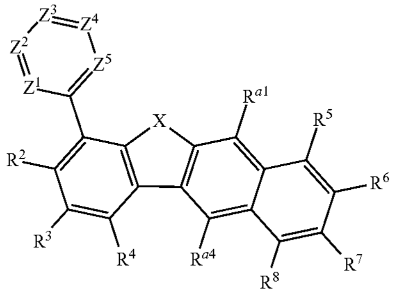
[Chemical Formula 1a-2-3]
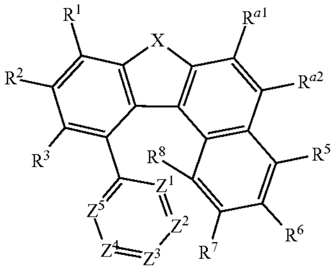
[Chemical Formula 1b-2-3]
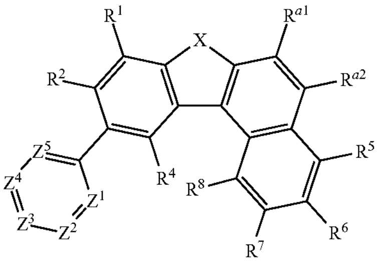
[Chemical Formula 1c-2-3]
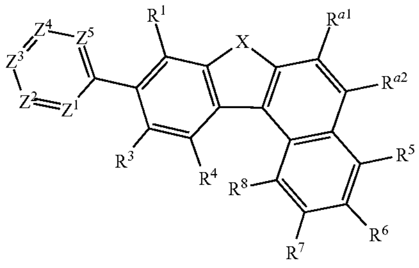
-continued
[Chemical Formula 1d-2-3]
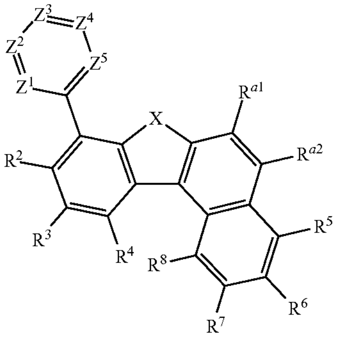
[Chemical Formula 1a-2-4]
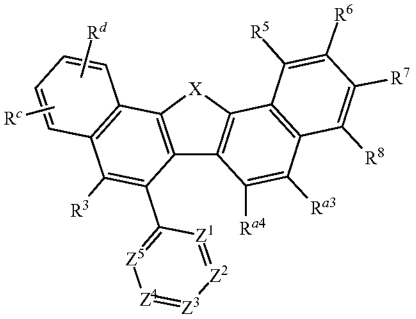
[Chemical Formula 1b-2-4]
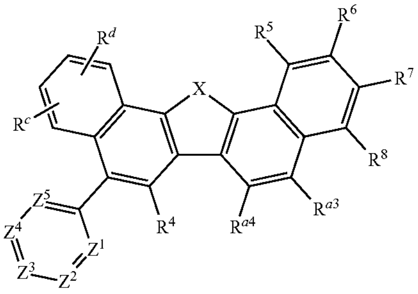
[Chemical Formula 1a-2-5]
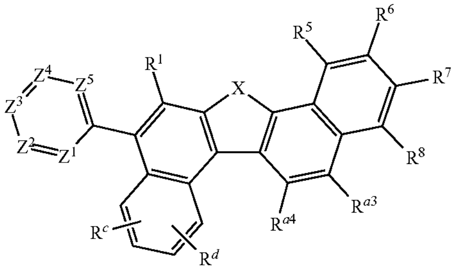
[Chemical Formula 1b-2-5]
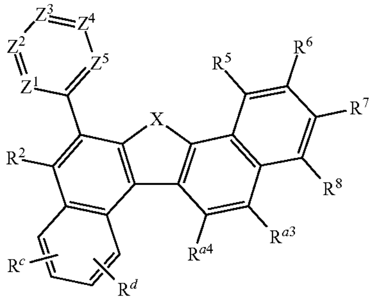

-continued

[Chemical Formula 1a-2-6]

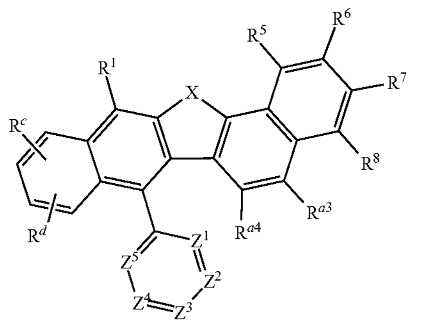

[Chemical Formula 1b-2-6]

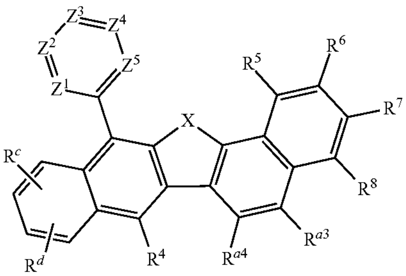

[Chemical Formula 1a-2-7]

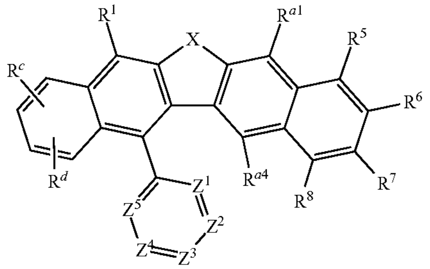

[Chemical Formula 1b-2-7]

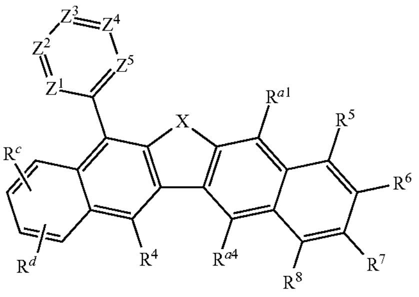

[Chemical Formula 1a-2-8]

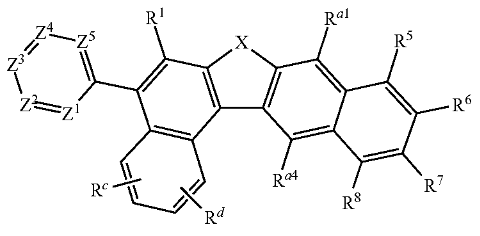

-continued

[Chemical Formula 1b-2-8]

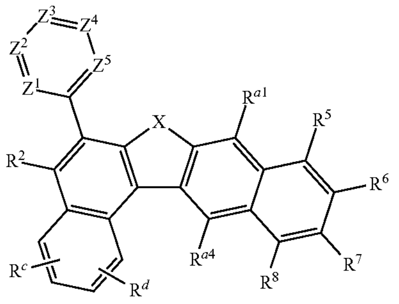

In Chemical Formula 1a-2-1 to Chemical Formula 1d-2-1, Chemical Formula 1a-2-2 to Chemical Formula 1d-2-2 and Chemical Formula 1a-2-3 to Chemical Formula 1d-2-3, Chemical Formula 1a-2-4, Chemical Formula 1b-2-4, Chemical Formula 1a-2-5, Chemical Formula 1b-2-5, Chemical Formula 1a-2-6, Chemical Formula 1b-2-6, Chemical Formula 1a-2-7, Chemical Formula 1b-2-7, Chemical Formula 1a-2-8, and Chemical Formula 1b-2-8, X, $R^c$, $R^d$, $R^1$ to $R^8$, $R^{a1}$ to $R^{a4}$ and $Z^1$ to $Z^5$ are the same as described above.

More specifically, the compound for an organic optoelectronic device according to an embodiment may be represented by Chemical Formula 1a-2-1 or Chemical Formula 1a-2-3.

As another example, the compound for an organic optoelectronic device according to a specific substitution position of the group represented by Chemical Formula A may be represented by a combination of Chemical Formula 2 and one of Chemical Formula 1e to Chemical Formula 1h.

[Chemical Formula 1e]

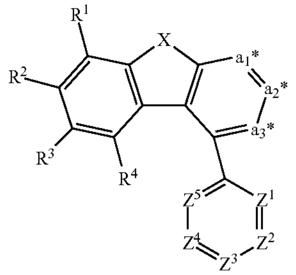

[Chemical Formula 1f]

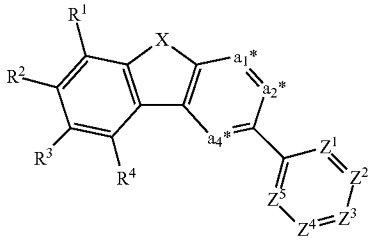

[Chemical Formula 1g]

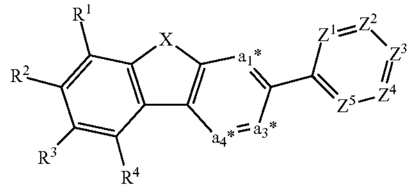

-continued

[Chemical Formula 1h]

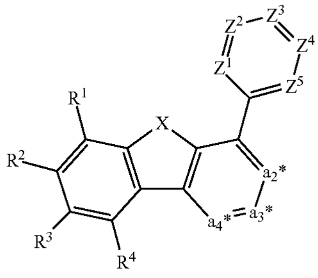

In Chemical Formula 1e to Chemical Formula 1h, $a_1$* to $a_4$*, $R^1$ to $R^4$, and $Z^1$ to $Z^5$ are the same as described above.

Specifically, one of Chemical Formula 1e to Chemical Formula 1h combined with Chemical Formula 2 may be represented by one of Chemical Formula 1e-2-1, Chemical Formula 1f-2-1, Chemical Formula 1e-2-2, Chemical Formula 1h-2-2, Chemical Formula 1g-2-3, Chemical Formula 1h-2-3, Chemical Formula 1e-2-5, Chemical Formula 1f-2-5, Chemical Formula 1e-2-6, Chemical Formula 1f-2-6, Chemical Formula 1e-2-8, and Chemical Formula 1f-2-8.

[Chemical Formula 1e-2-1]

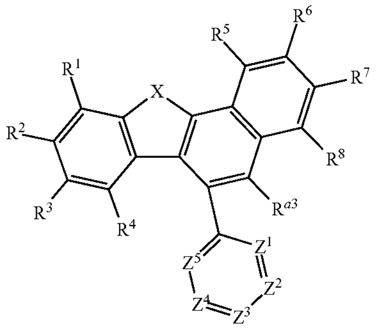

[Chemical Formula 1f-2-1]

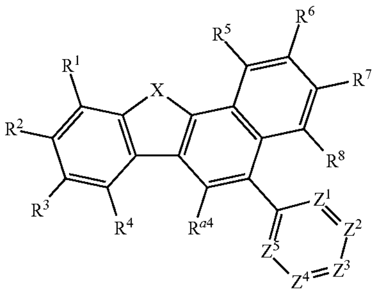

[Chemical Formula 1e-2-2]

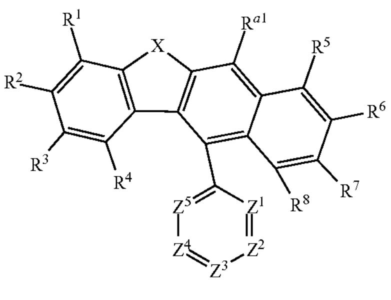

-continued

[Chemical Formula 1h-2-2]

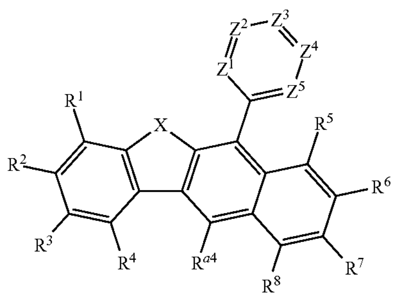

[Chemical Formula 1g-2-3]

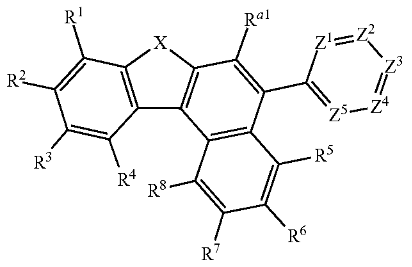

[Chemical Formula 1h-2-3]

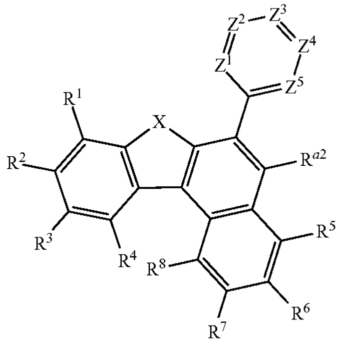

[Chemical Formula 1e-2-5]

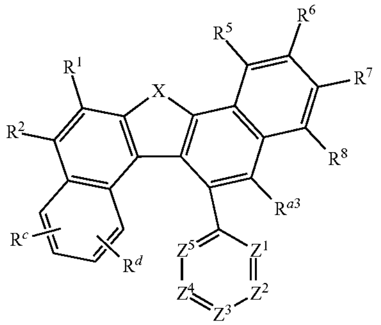

[Chemical Formula 1f-2-5]

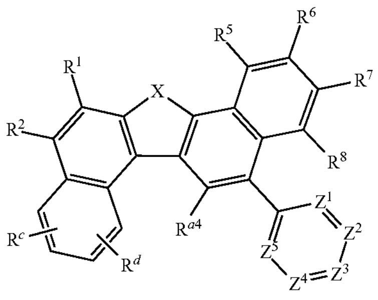

-continued

[Chemical Formula 1e-2-6]

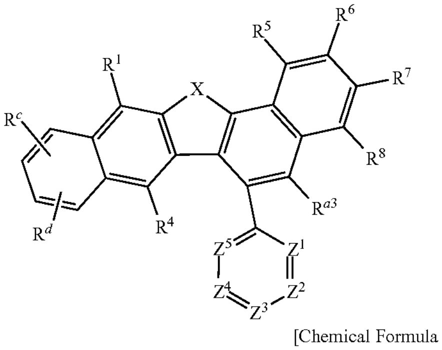

[Chemical Formula 1f-2-6]

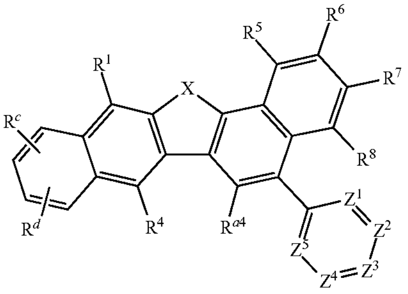

[Chemical Formula 1e-2-8]

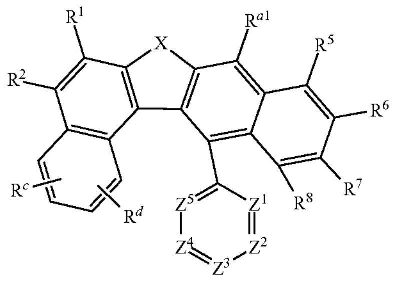

[Chemical Formula 1f-2-8]

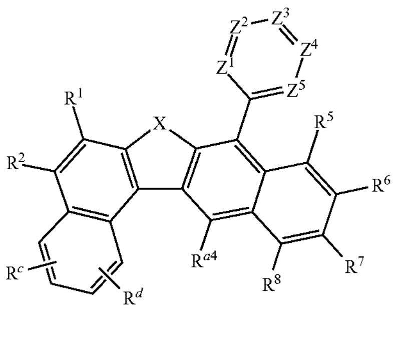

In Chemical Formula 1e-2-1, Chemical Formula 1f-2-1, Chemical Formula 1e-2-2, Chemical Formula 1h-2-2, Chemical Formula 1g-2-3, Chemical Formula 1h-2-3, Chemical Formula 1e-2-5, Chemical Formula 1f-2-5, Chemical Formula 1e-2-6, Chemical Formula 1f-2-6, Chemical Formula 1e-2-8, and Chemical Formula 1f-2-8, X, $R^c$, $R^d$, $R^1$ to $R^8$ and $R^{a1}$, $R^{a3}$, $R^{a4}$ and $Z^1$ to $Z^5$ are the same as described above.

More specifically, the compound for an organic optoelectronic device according to an embodiment may be selected from Chemical Formula 1e-2-1, Chemical Formula 1f-2-1, Chemical Formula 1e-2-1, Chemical Formula 1e-2-2, Chemical Formula 1g-2-3, and Chemical Formula 1h-2-3.

The compound for an organic optoelectronic device according to one of the most specific embodiments may be selected from Chemical Formula 1a-2-1, Chemical Formula 1e-2-1 and Chemical Formula 1e-2-2.

The $R^c$, $R^d$, $R^1$ to $R^8$, and $R^{a1}$ to $R^{a4}$ may be specifically hydrogen, deuterium, a cyano group, a halogen, a C1 to C10 alkyl group or a substituted or unsubstituted C6 to C12 aryl group, for example, all hydrogen, but are not limited thereto.

In Chemical Formula A, $Z^1$ to $Z^5$ may be specifically N or C—$R^b$, and at least two of $Z^1$ to $Z^5$ may be N.

The group represented by Chemical Formula A composed of $Z^1$ to $Z^5$, may be, specifically, a substituted or unsubstituted pyridyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted benzoquinazolinyl group, a substituted or unsubstituted benzofuranpyrimidinyl group, or a substituted or unsubstituted benzothiophenepyrimidinyl group.

For example the group represented by Chemical Formula A may be a substituted or unsubstituted pyrimidinyl group, or a substituted or unsubstituted triazinyl group.

In Chemical Formula A, $R^b$ may be a substituted or unsubstituted phenyl group, a substituted or unsubstituted biphenyl group, a substituted or unsubstituted terphenyl group, a substituted or unsubstituted triphenylene group, a substituted or unsubstituted fluorenyl group, a substituted or unsubstituted carbazolyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuranyl group, or a substituted or unsubstituted benzonaphthothiophenyl group.

When $R^b$ of Chemical Formula A is substituted, the substituent may be, for example, deuterium, a cyano group, a C1 to C5 alkyl group, a phenyl group, a biphenyl group, or a naphthyl group, but is not limited thereto.

As a more specific example, the group represented by Chemical Formula A may be selected from the substituents of Group I.

[Group I]

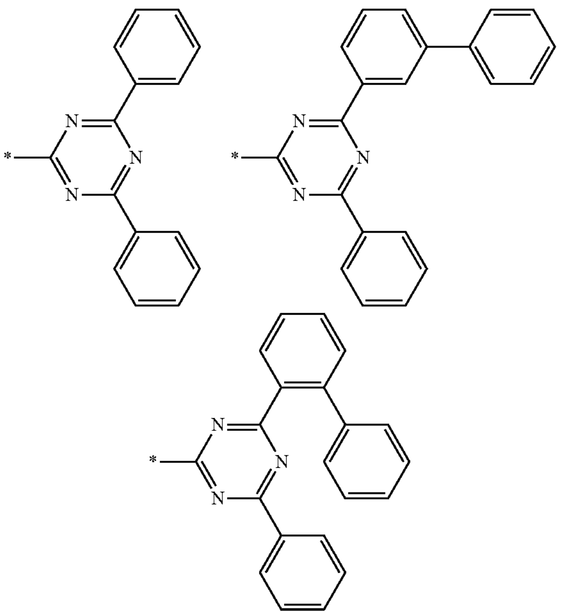

-continued
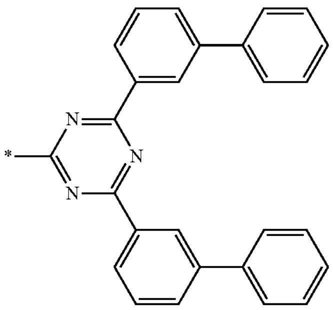
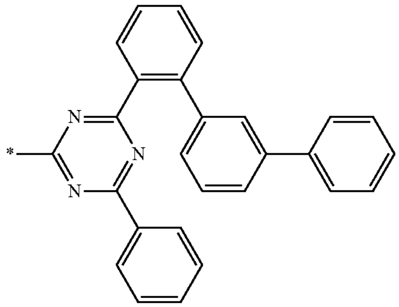
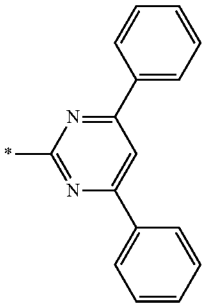
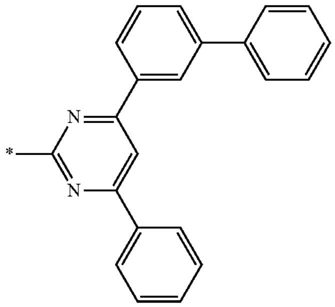
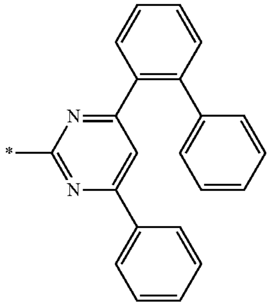
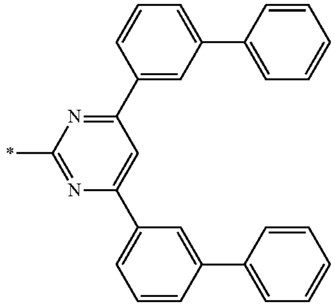
-continued
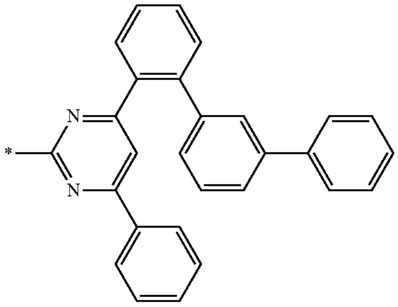
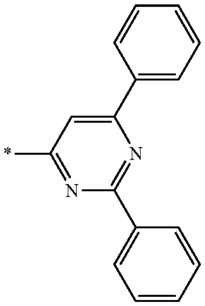
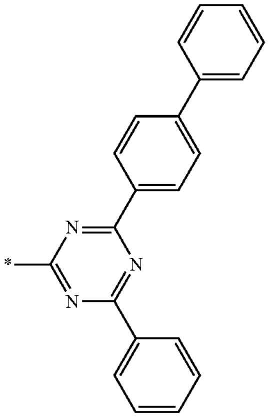
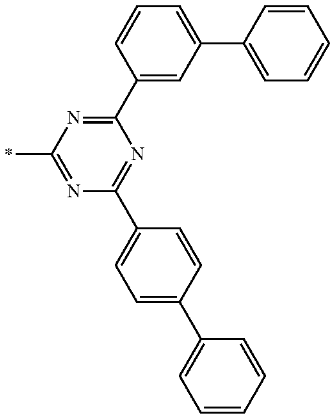
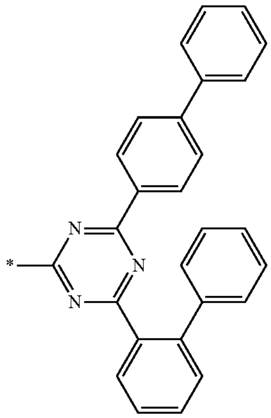

-continued
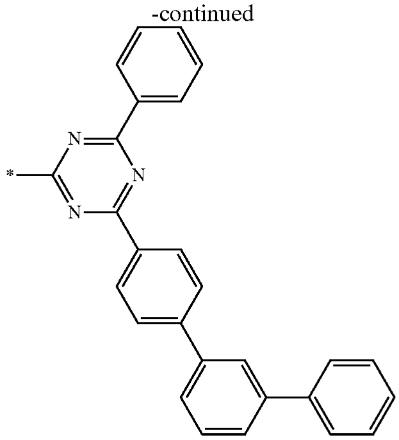
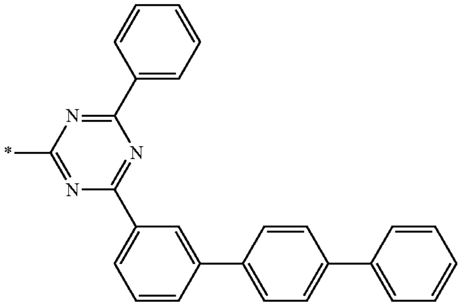
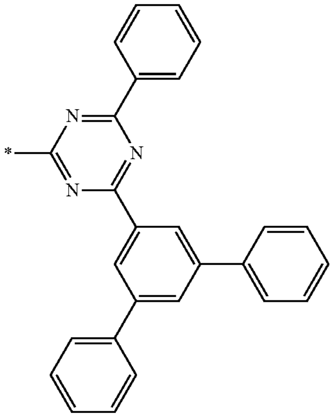
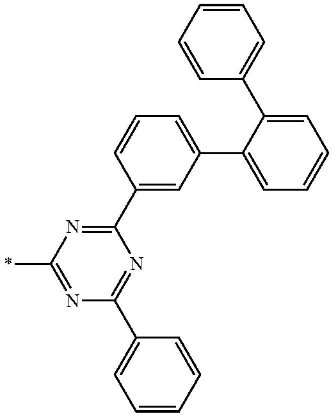
-continued
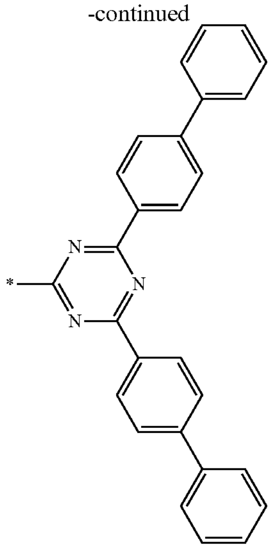
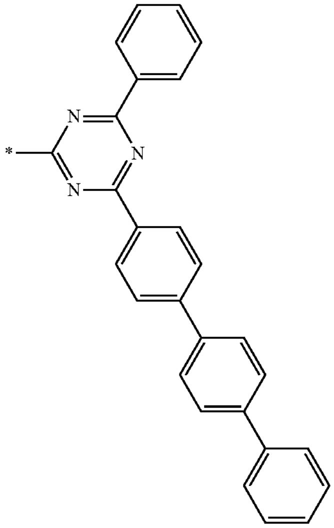
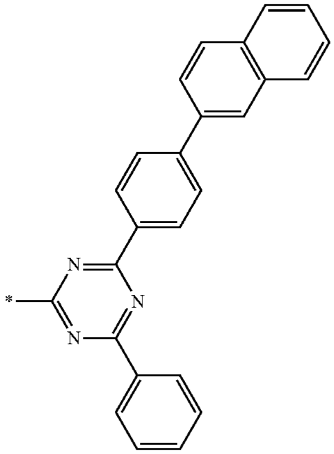

-continued
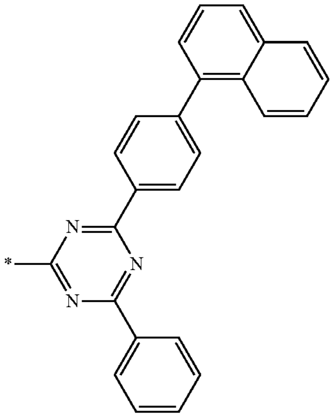
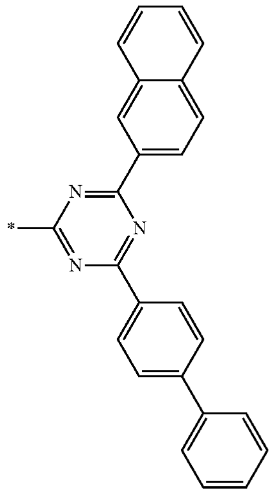
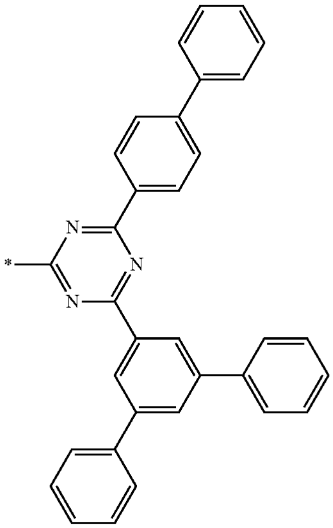
-continued
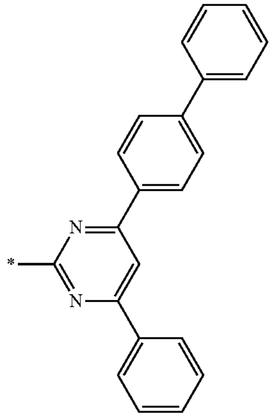
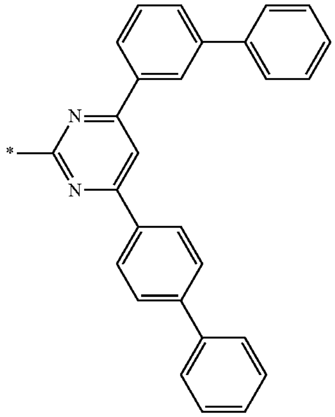
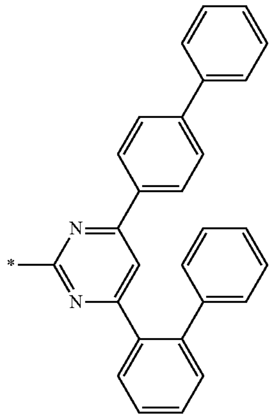
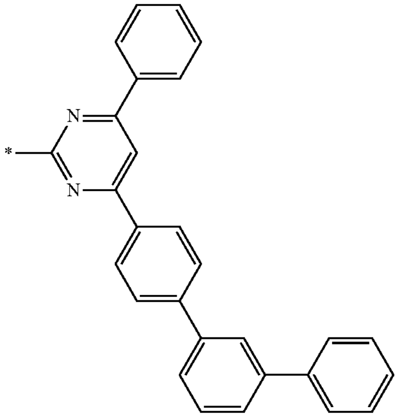

-continued
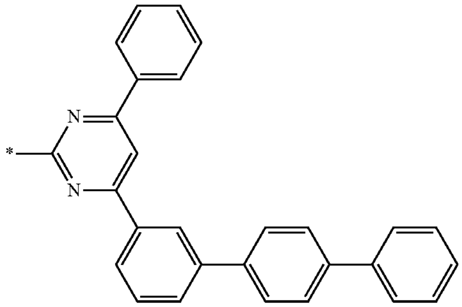
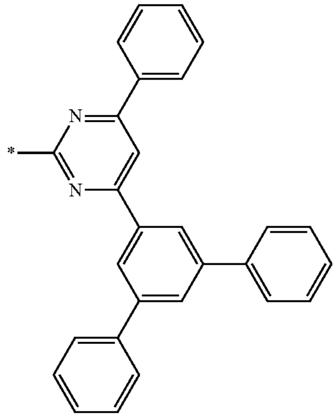
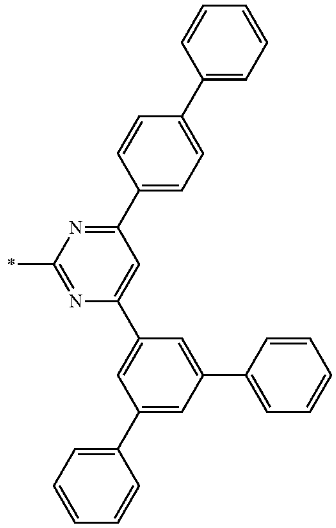
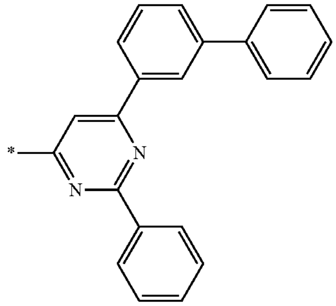
-continued
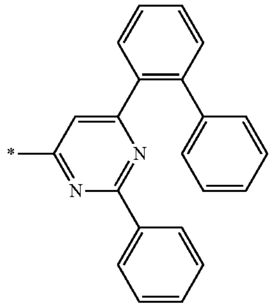
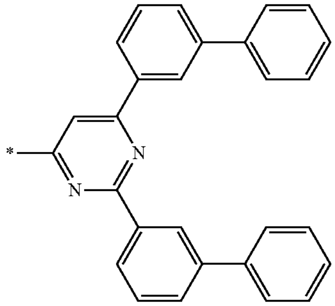
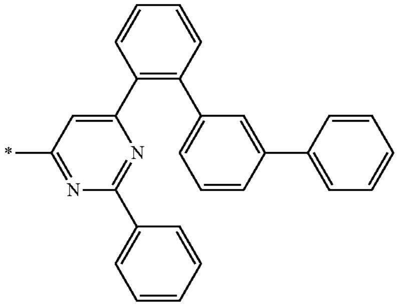
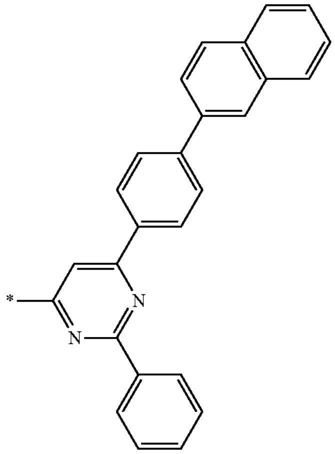

-continued
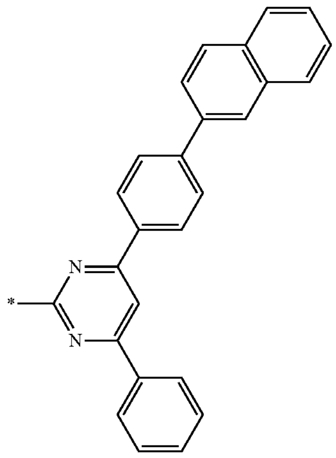
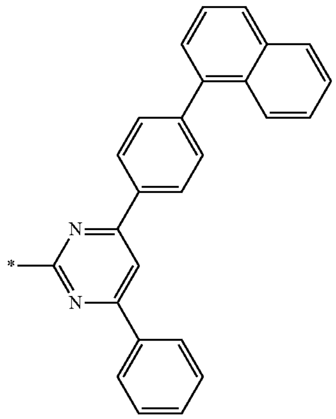
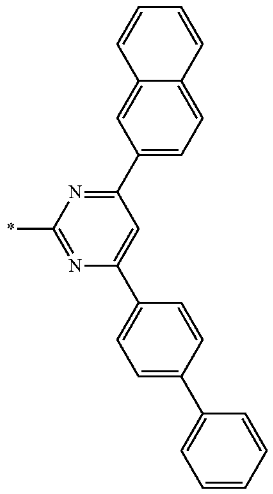
-continued
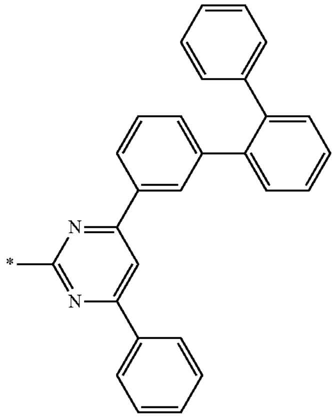
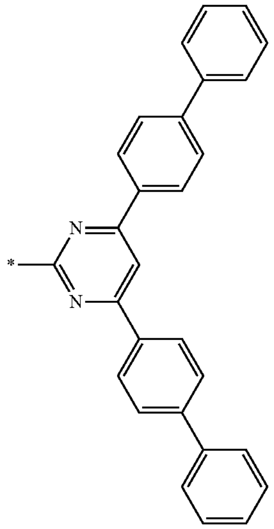
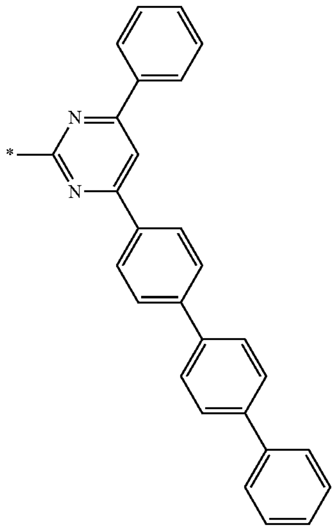

-continued
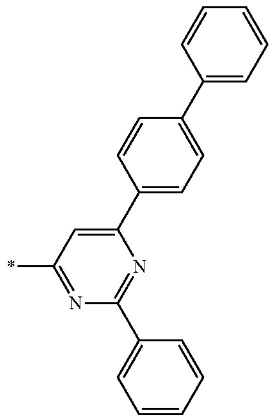
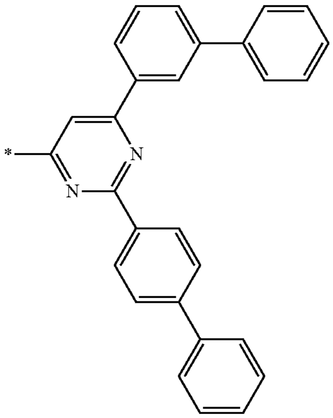
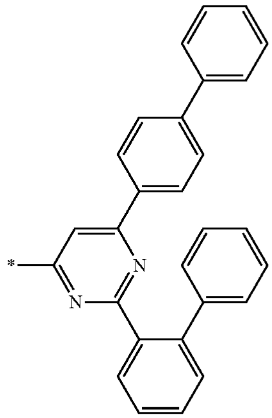
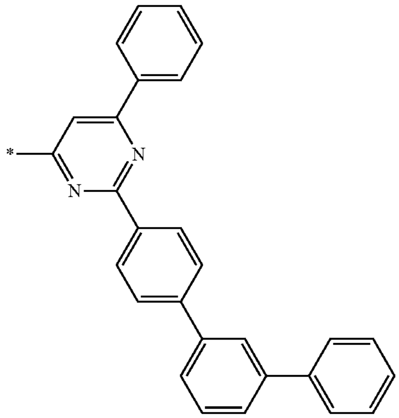
-continued
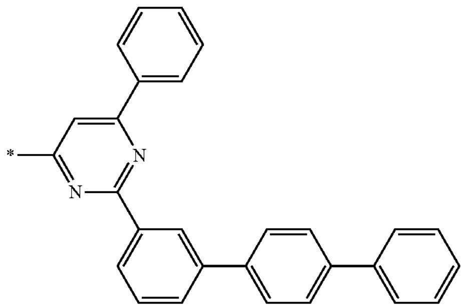
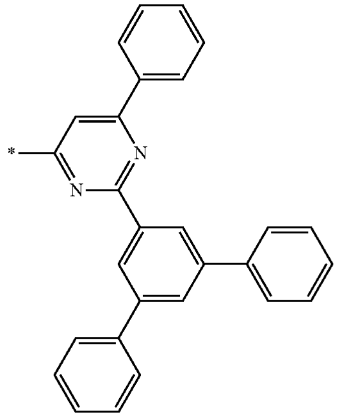
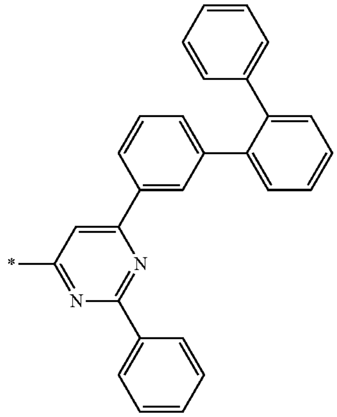
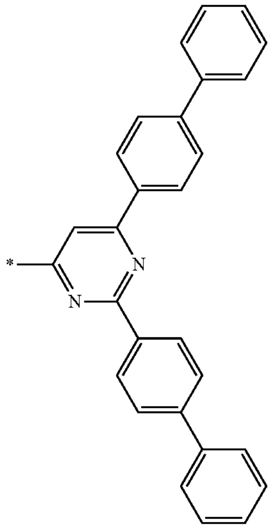

-continued
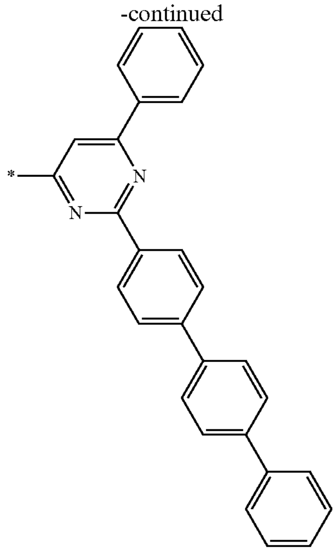
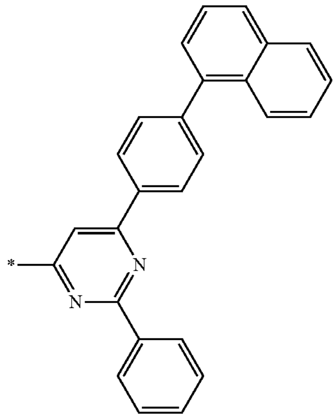
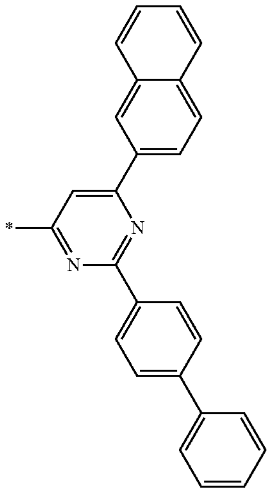
-continued
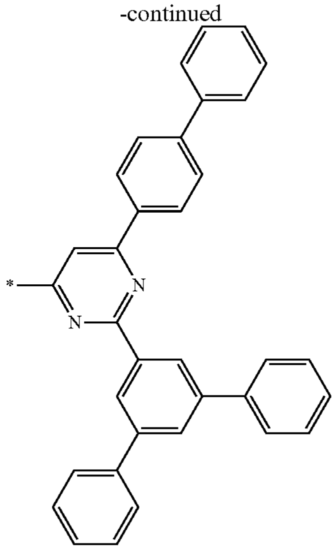
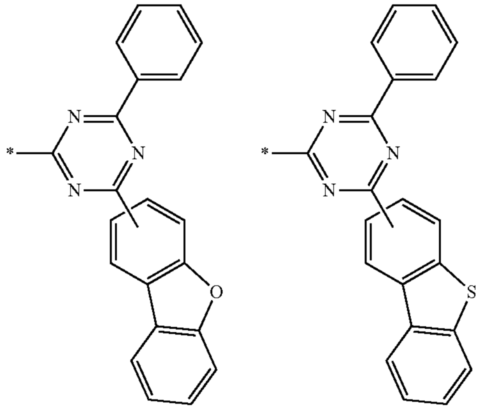
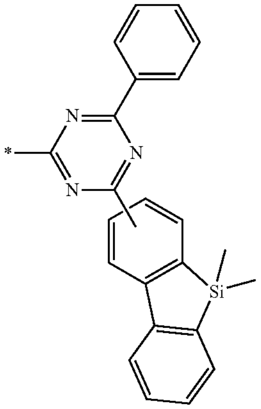

-continued
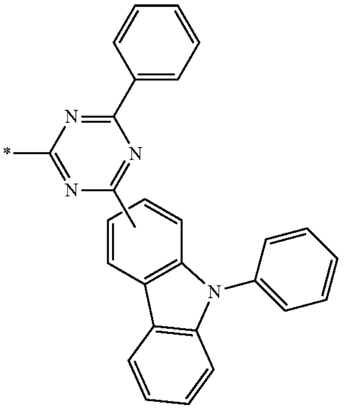
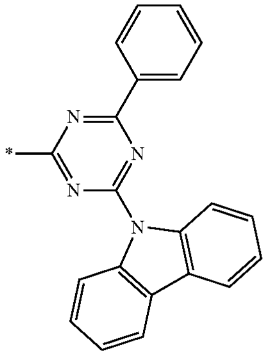
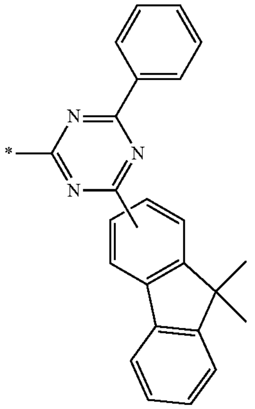
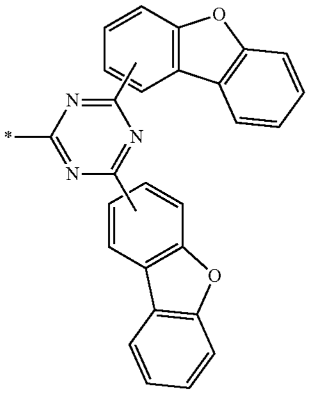
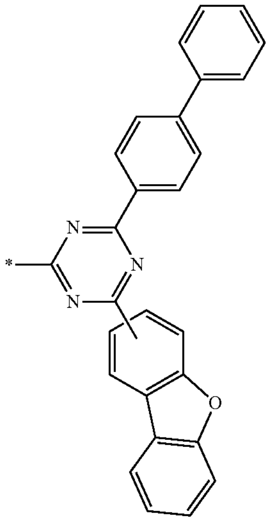
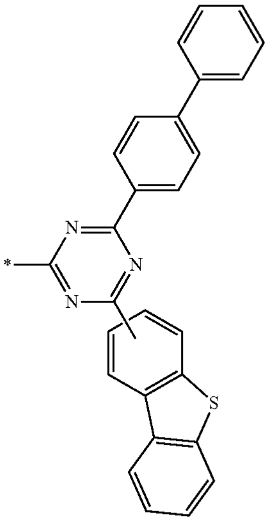
-continued
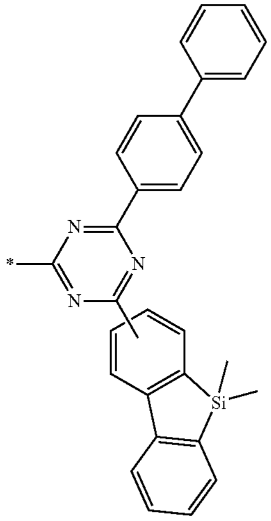
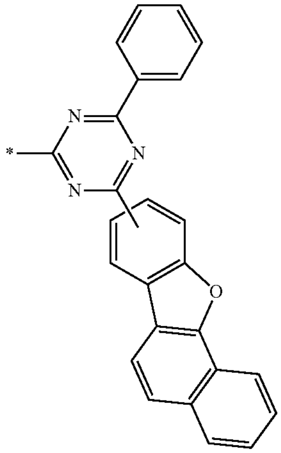
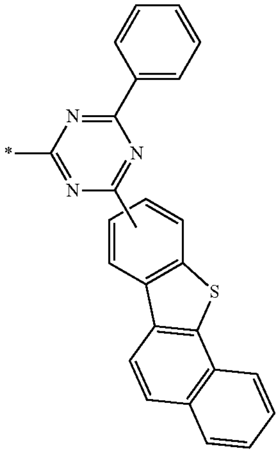
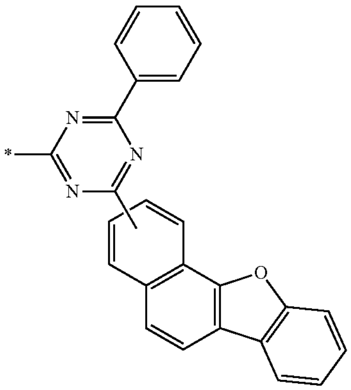

-continued
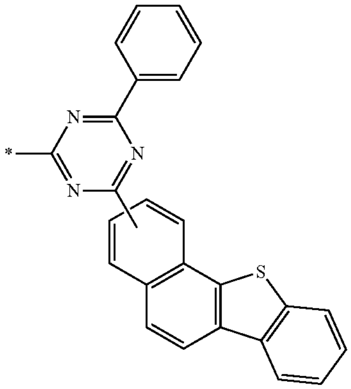
In Group I, * is a linking point.
For example, the compound for an organic optoelectronic device may be one selected from compounds of Group 1, but is not limited thereto.
[Group 1]
[A-5]
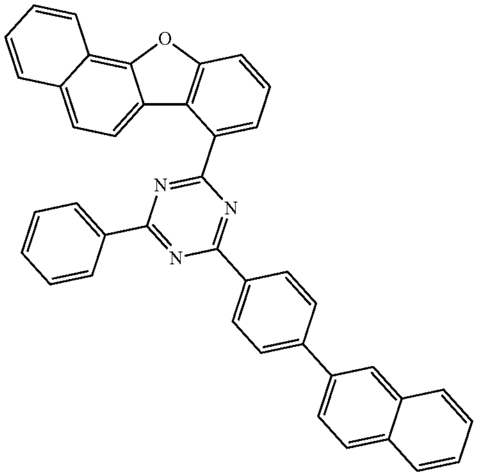
[A-6]
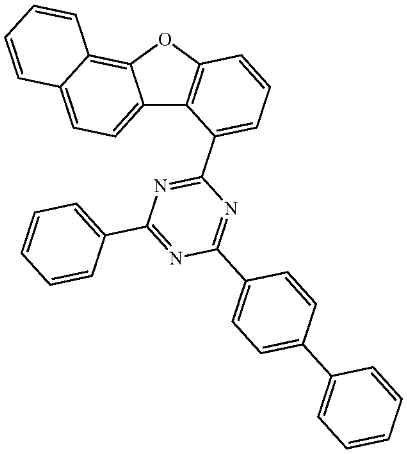
-continued
[A-7]
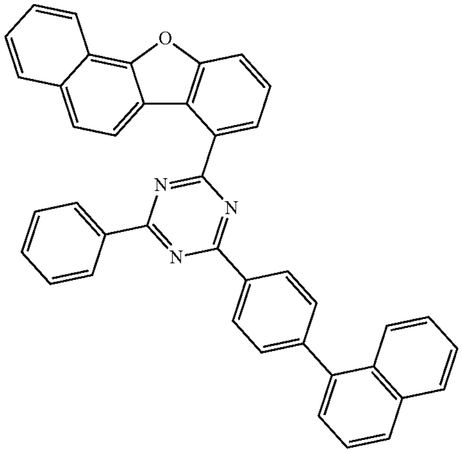
[A-11]
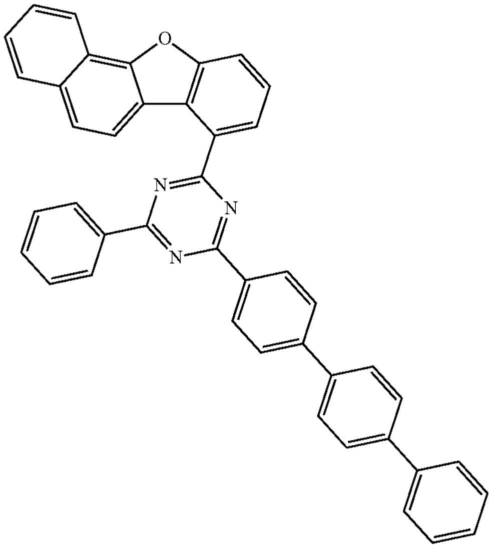
[A-12]
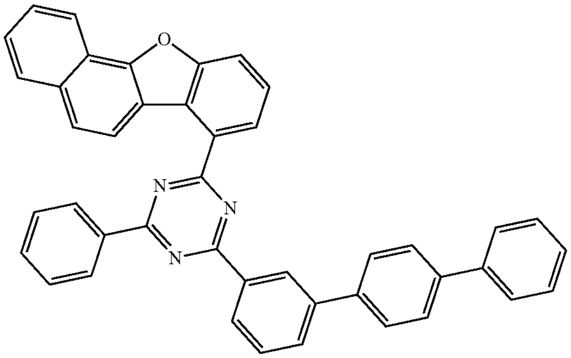

-continued
[A-13]
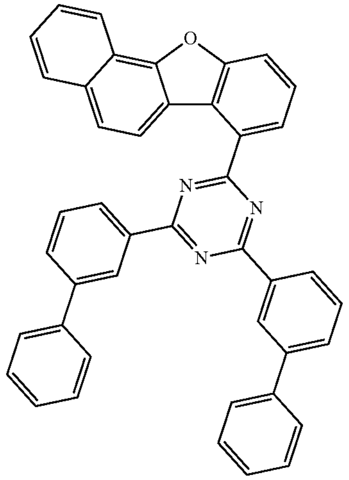
[A-15]
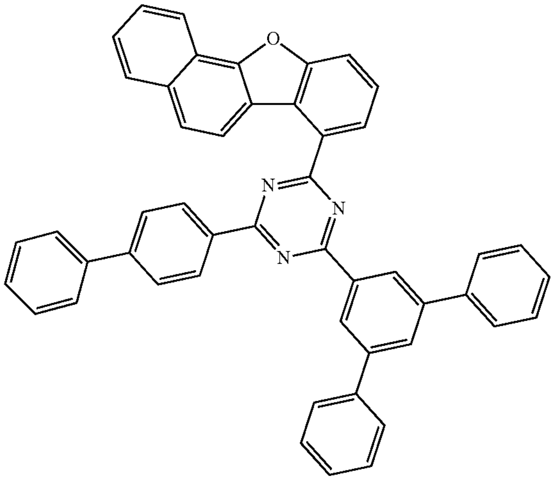
[A-16]
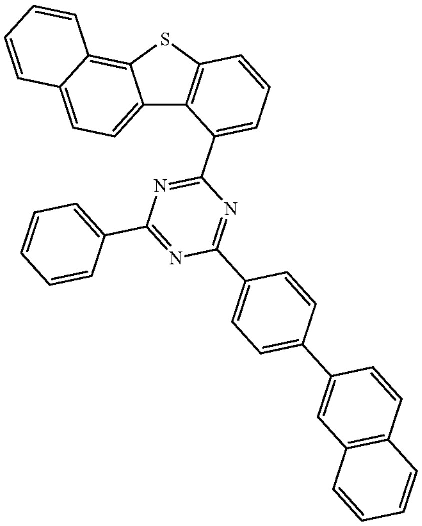
-continued
[A-19]
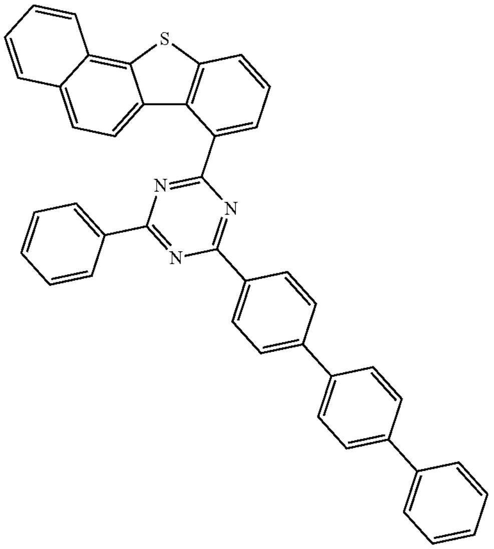
[A-25]
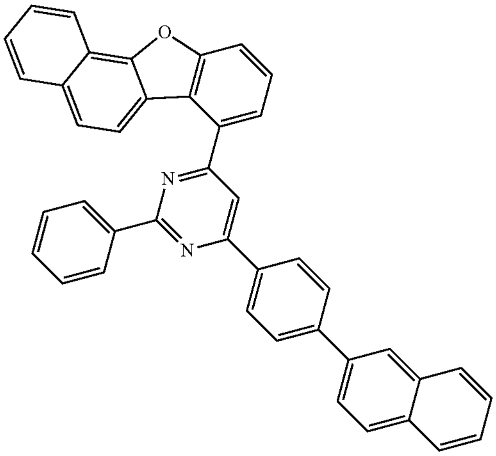
[A-26]
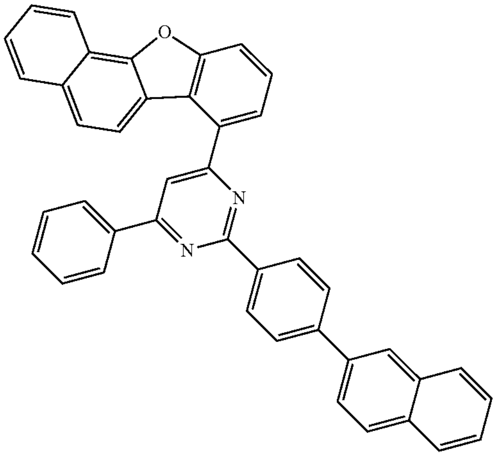

-continued
[A-27]
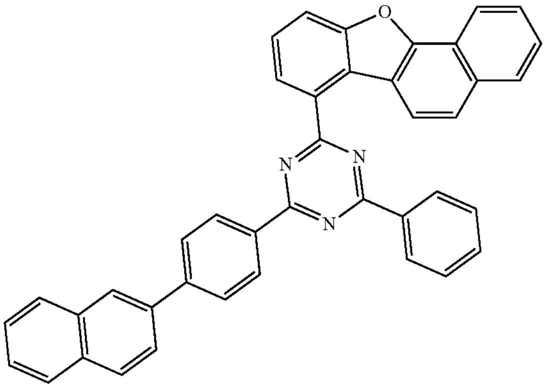
[A-63]
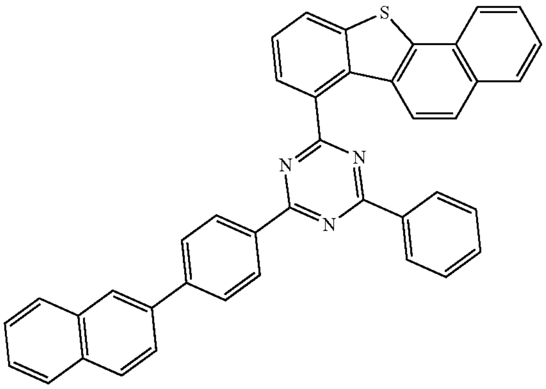
[A-99]
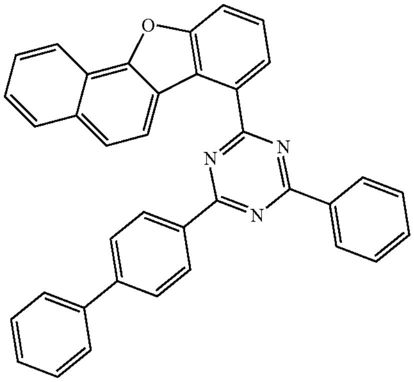
[A-100]
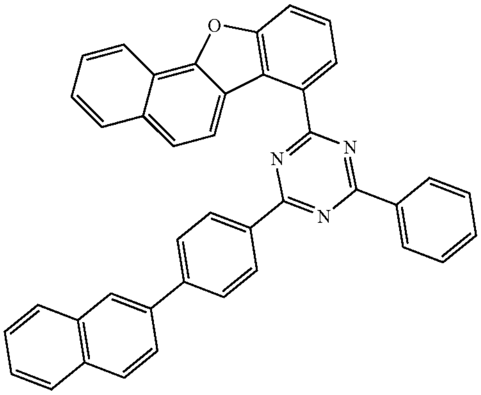
-continued
[A-101]
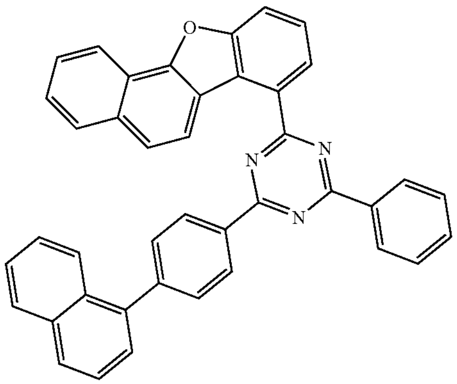
[A-102]
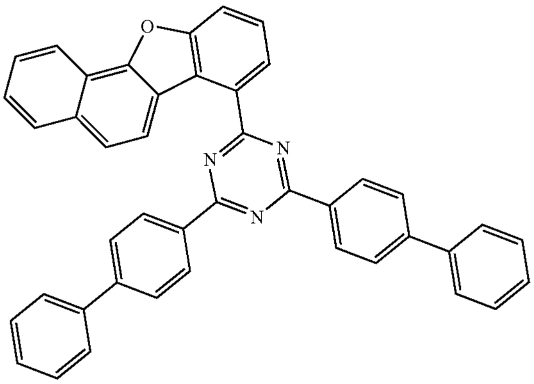
[A-117]
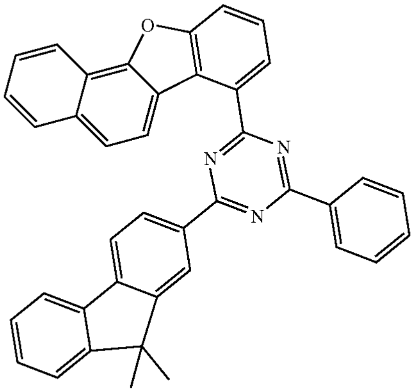
[A-119]
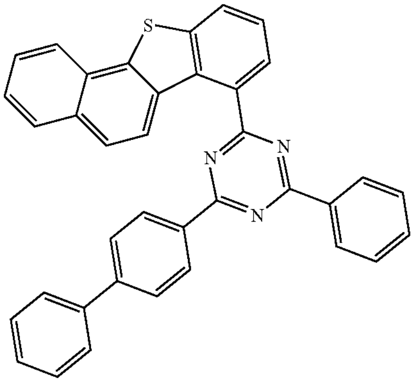

[A-120]
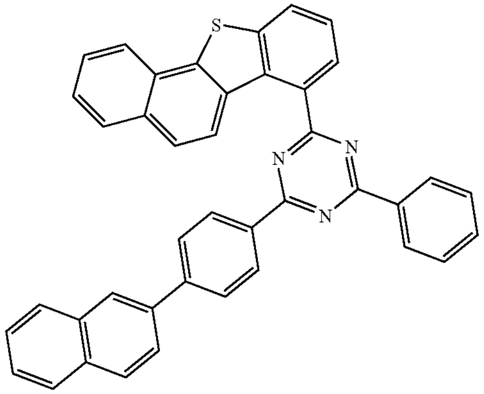
[A-121]
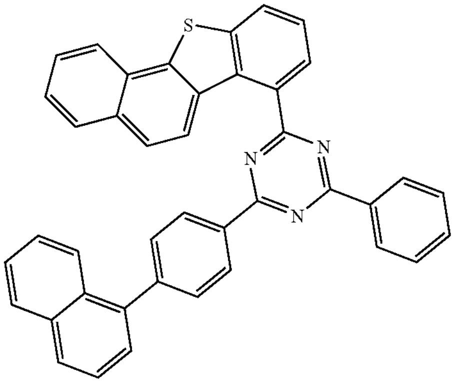
[A-122]
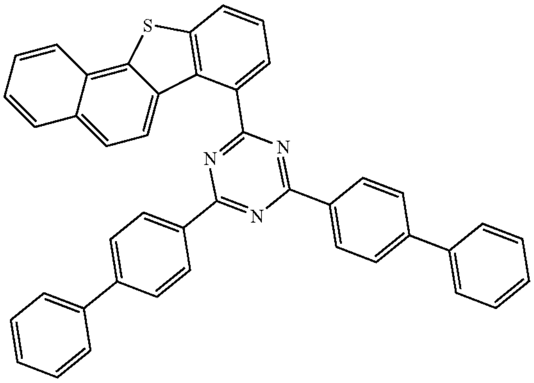
[A-137]
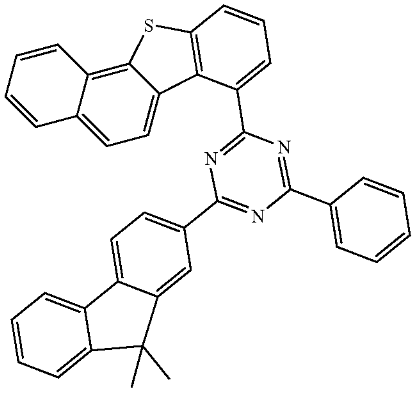
[A-139]
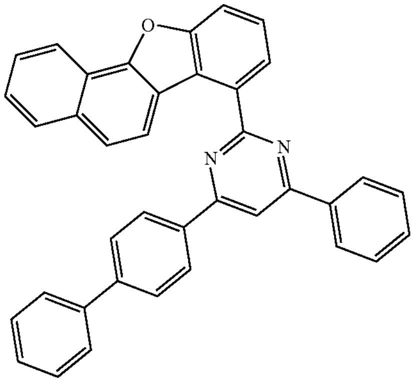
[A-140]
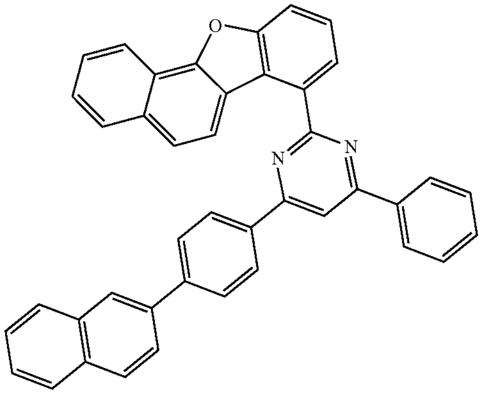
[A-141]
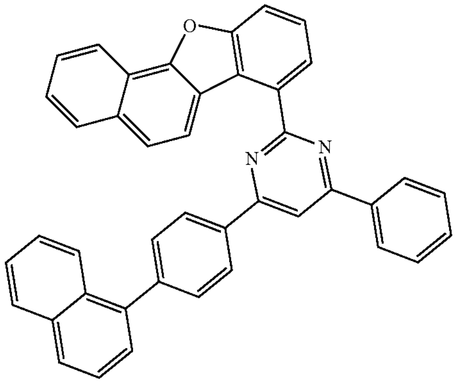
[A-142]
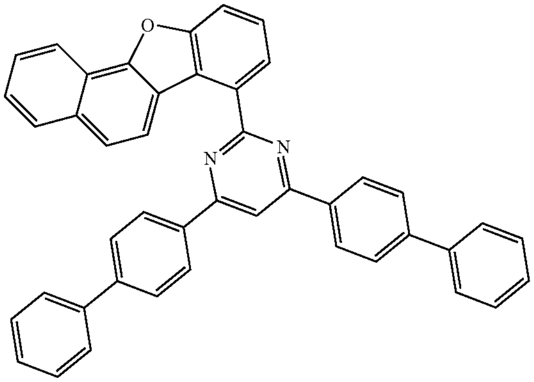

-continued
[A-143]
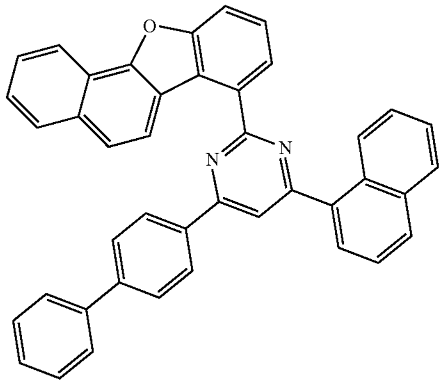
[A-144]
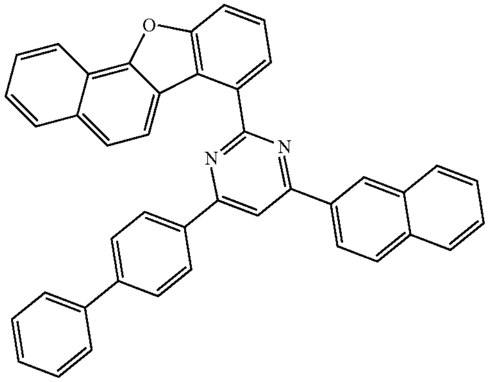
.
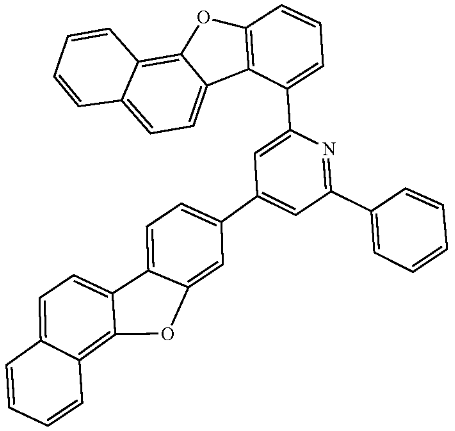
-continued
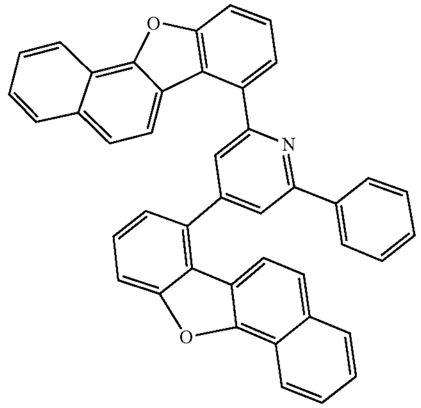
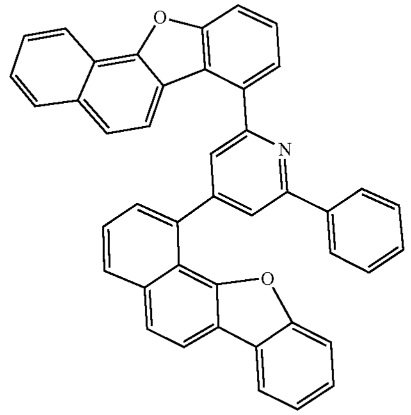
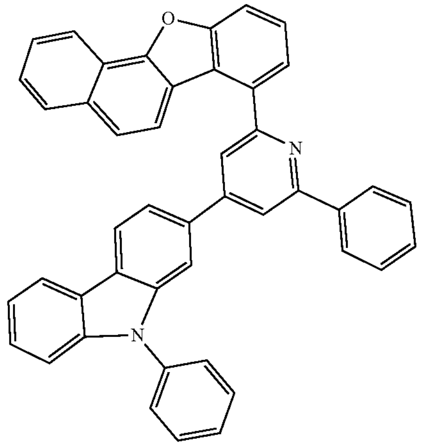
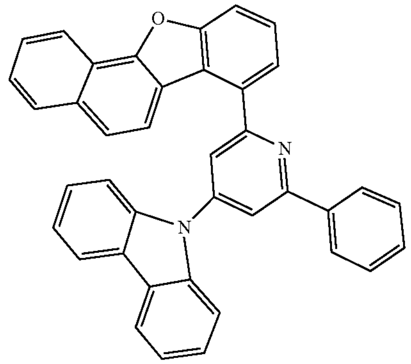

-continued

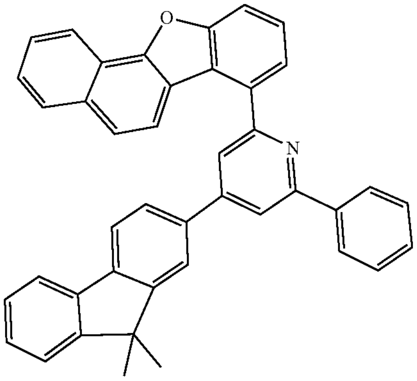

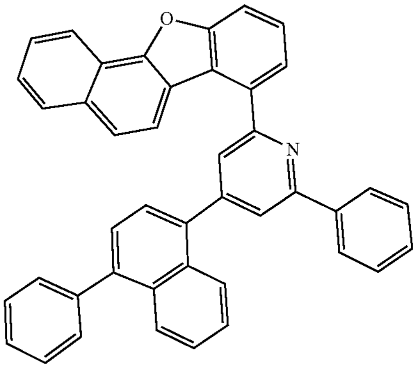

A composition for an organic optoelectronic device according to an embodiment may include a first compound for an organic optoelectronic device including the compound for an organic optoelectronic device described above, and a second compound for an organic optoelectronic device represented by Chemical Formula 3; or a combination of Chemical Formula 4 and Chemical Formula 5.

[Chemical Formula 3]

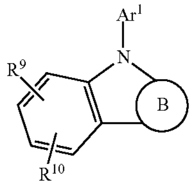

In Chemical Formula 3, $Ar^1$ is a substituted or unsubstituted C6 to C30 aryl group, a substituted or unsubstituted C2 to C30 heterocyclic group, or a combination thereof, and cyclic B is represented by Chemical Formula B-1 or Chemical Formula B-2,

[Chemical Formula B-1]

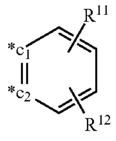

-continued

[Chemical Formula B-2]

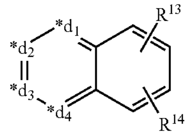

$*C_1$ and $*C_2$ of Chemical Formula B-1 are independently linking carbon, adjacent two of $*d_1$ to $*d_4$ in Chemical Formula B-2 are independently linking carbon, and the other two that are not linked are independently C—$R^d$, $R^d$ and $R^9$ and $R^{14}$ are independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^d$ and $R^9$ and $R^{14}$ is a group represented by Chemical Formula C,

[Chemical Formula C]

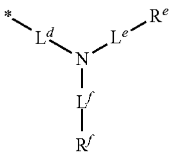

wherein, in Chemical Formula C, $L^d$ to $L^f$ are independently a single bond, or a substituted or unsubstituted C6 to C20 arylene group, $R^e$ and $R^f$ are independently a substituted or unsubstituted C6 to C30 aryl group, a substituted or unsubstituted C2 to C30 heterocyclic group, or a combination thereof, and

* is a linking point;

[Chemical Formula 4]

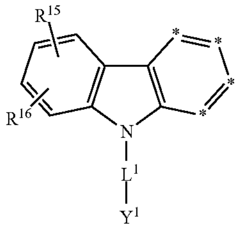

[Chemical Formula 5]

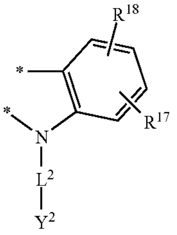

wherein, in Chemical Formula 4 and Chemical Formula 5, $Y^1$ and $Y^2$ are independently a substituted or unsubstituted C6 to C20 aryl group, or a substituted or unsubstituted C2 to C30 heterocyclic group, two adjacent *'s of Chemical Formula 4 are linked to Chemical Formula 5,

*'s of Chemical Formula 4 not linked to Chemical Formula 5 are independently C-$L^g$-$R^g$, $L^g$, $L^1$, and $L^2$ are independently a single bond, or a substituted or unsubstituted C6 to C20 arylene group, and $R^g$ and $R^{15}$ to $R^{18}$ are independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group.

The second compound for an organic optoelectronic device is used with the first compound for an organic optoelectronic device in a light emitting layer, and thereby charge mobility and stability are increased and luminous efficiency and life-span characteristics are improved.

For example, the compound for a second organic optoelectronic device represented by Chemical Formula 3 may be represented by one of Chemical Formula 3B-1, Chemical Formula 3B-2A, Chemical Formula 3B-2B, and Chemical Formula 3B-2C.

[Chemical Formula 3B-1]

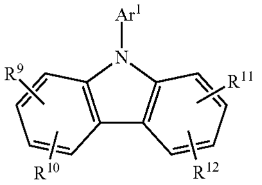

[Chemical Formula 3B-2A]

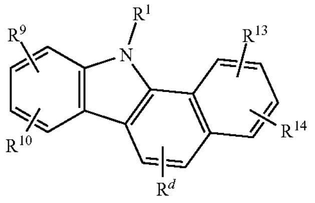

[Chemical Formula 3B-2B]

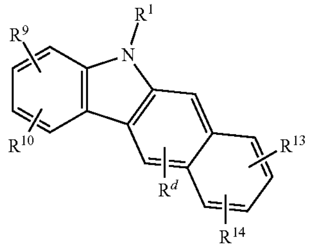

[Chemical Formula3B-2C]

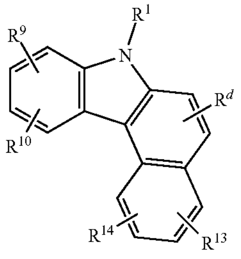

In Chemical Formula 3B-1, Chemical Formula 3B-2A, Chemical Formula 3B-2B, and Chemical Formula 3B-2C, $Ar^1$, $R^d$ and $R^9$ and $R^{14}$ are the same as described above.

For example, the compound for a second organic optoelectronic device represented by the combination of Chemical Formula 4 and Chemical Formula 5 may be represented by one of Chemical Formula Chemical Formula 4A to Chemical Formula 4E.

[Chemical Formula 4A]

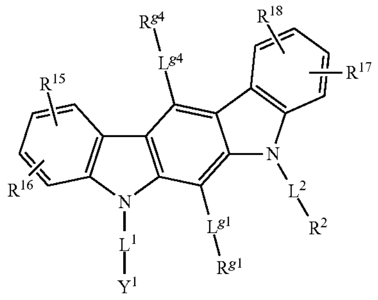

[Chemical Formula 4B]

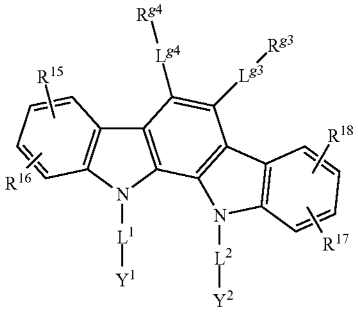

[Chemical Formula 4C]

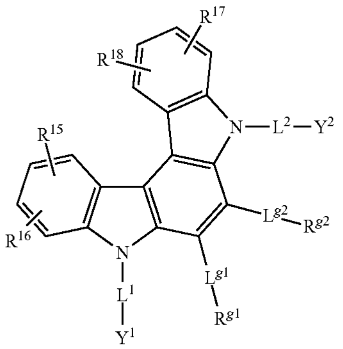

[Chemical Formula 4D]

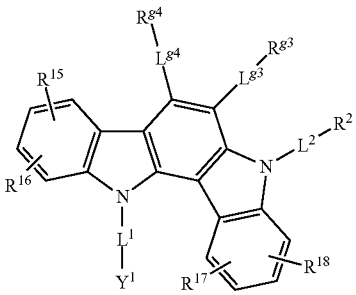

-continued

[Chemical Formula 4E]

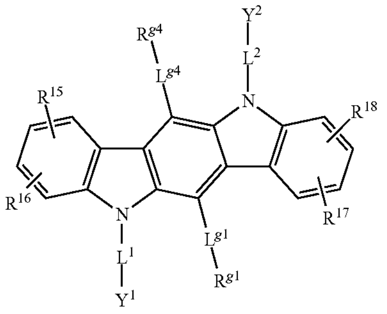

In Chemical Formula 4A to Chemical Formula 4E, $Y^1$ and $Y^2$, $L^1$ and $L^2$, and $R^{15}$ to $R^{18}$ are the same as described above, $L^{g1}$ to $L^{g4}$ are the same as the definitions of $L^1$ and $L^2$ described above, and $R^{g1}$ to $R^{g4}$ are as defined for $R^{15}$ to $R^{18}$ described above.

For example, $Y^1$ and $Y^2$ of Chemical Formulas 4 and 5 may independently be a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, and $R^{g1}$ to $R^{g4}$ and $R^{15}$ to $R^{18}$ may independently be hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In a specific embodiment of the present invention, $Y^1$ and $Y^2$ in Chemical Formulas 4 and 5 may independently be selected from substituents of Group II.

[Group II]

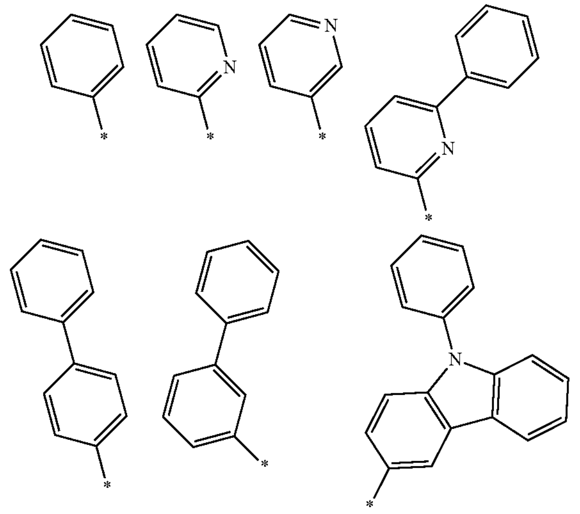

-continued

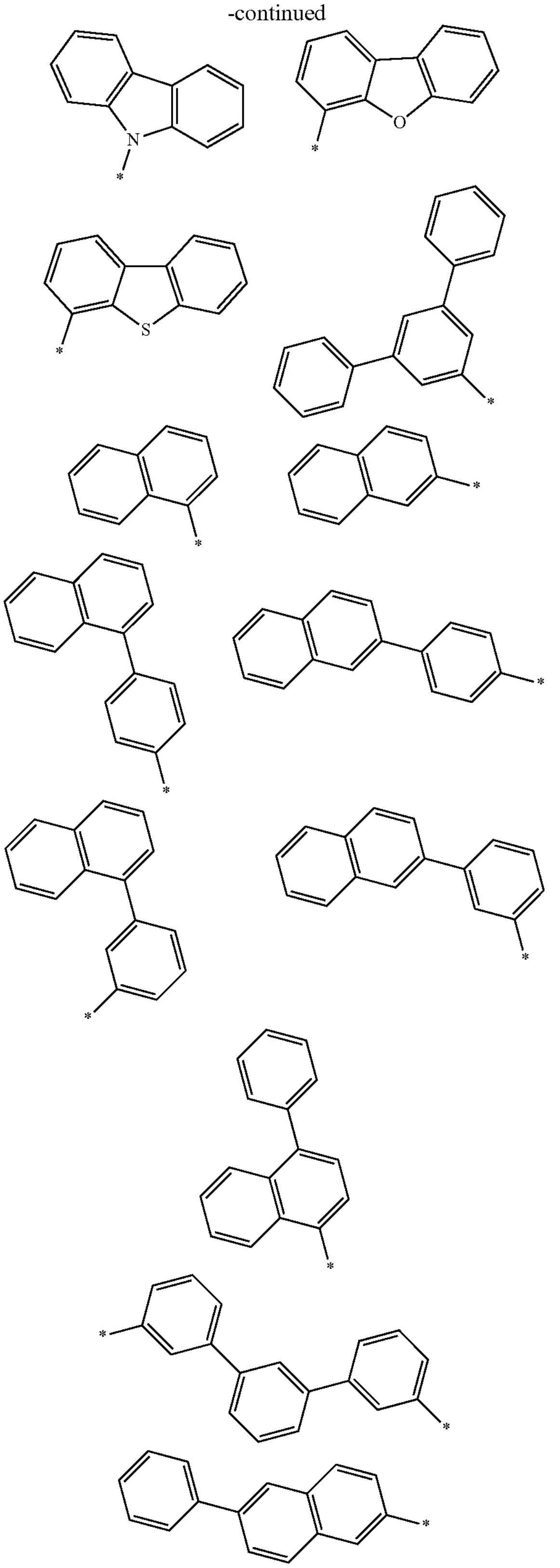

In Group II, * is a linking point with $L^1$ and $L^2$, respectively.

In an embodiment, the $R^{g1}$ to $R^{g4}$ and $R^{15}$ to $R^{18}$ may independently be hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

For example the $R^{g1}$ to $R^{g4}$ and $R^{15}$ to $R^{18}$ may independently be hydrogen, deuterium, a cyano group, or a substituted or unsubstituted phenyl group, and in one specific embodiment, the $R^{g1}$ to $R^{g4}$ are each hydrogen, and $R^{15}$ to $R^{18}$ may independently be hydrogen or a phenyl group.

In one specific embodiment of the present invention, the compound for a second organic optoelectronic device may be represented by Chemical Formula 4C.

Herein, $Y^1$ to $Y^2$ of Chemical Formula 3C may independently be a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, $L^1$, $L^2$, $L^{g1}$, and $L^{g2}$ may independently be a single bond, or a substituted or unsubstituted C6 to C20 arylene group, and $R^{g1}$, $R^{g2}$, and $R^{15}$ to $R^{18}$ may independently be hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

For example, the compound for the second organic optoelectronic device may be one selected from compounds of Group 2, but is not limited thereto.

[Group 2]

[B-1]

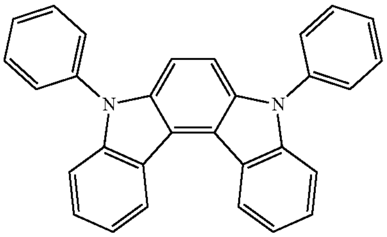

[B-2]

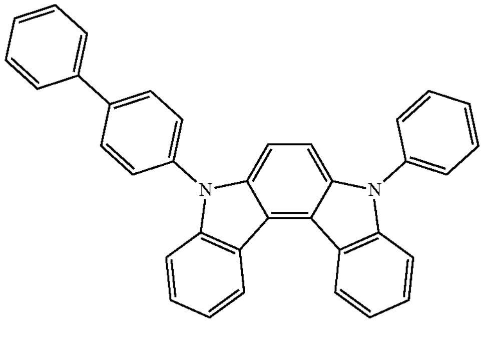

-continued

[B-3]

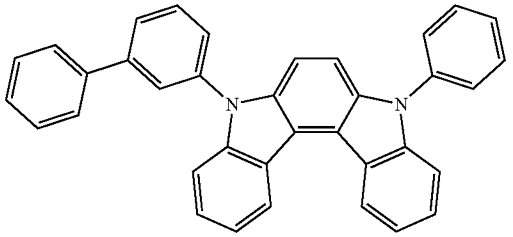

[B-4]

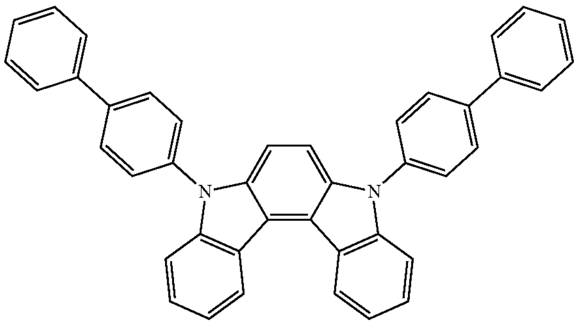

[B-5]

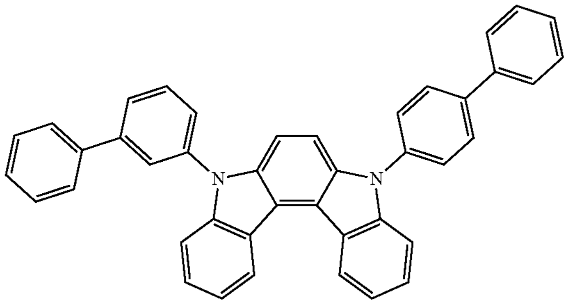

[B-6]

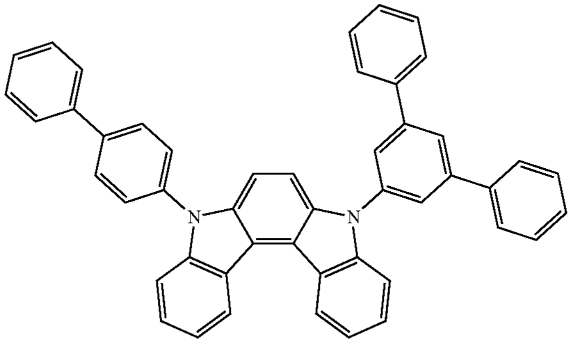

-continued
[B-7]
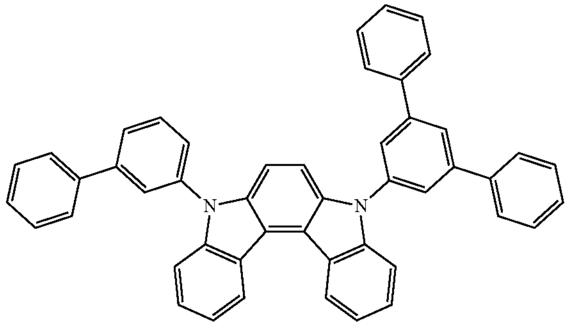
[B-8]
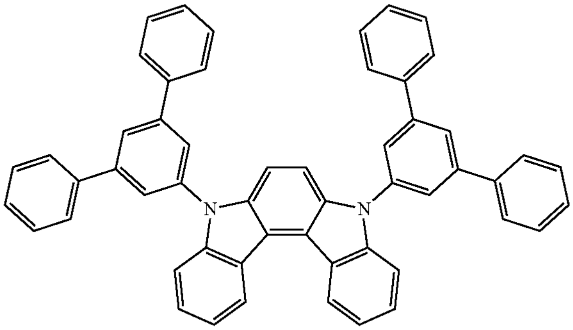
[B-9]
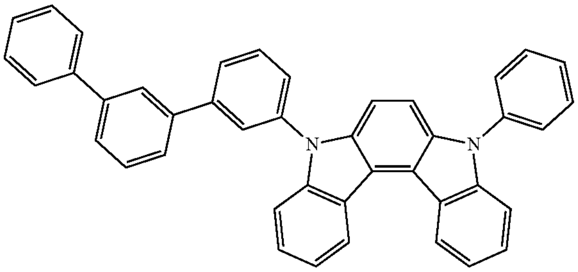
[B-10]
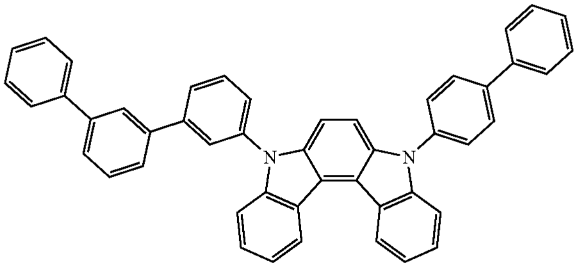
-continued
[B-11]
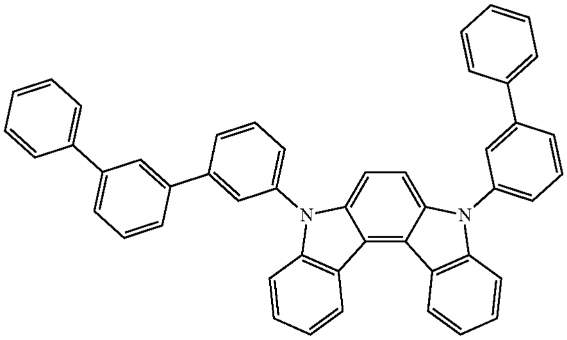
[B-12]
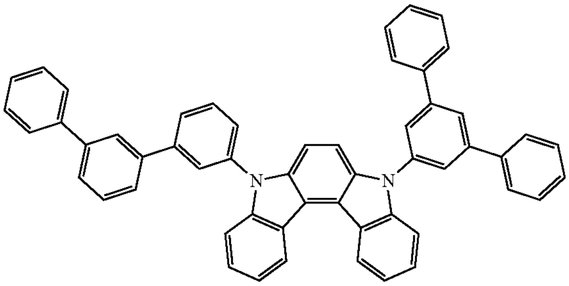
[B-13]
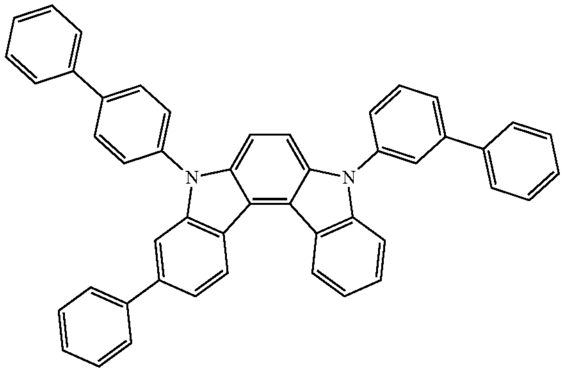
[B-14]
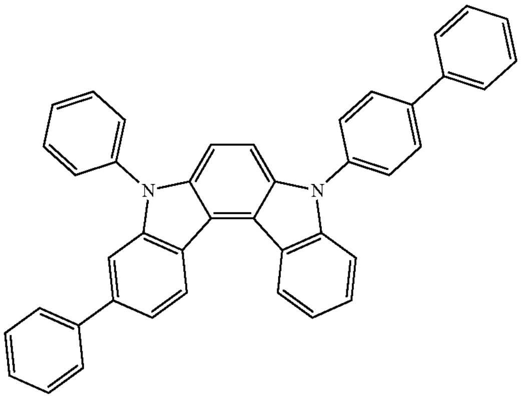

-continued
[B-15]
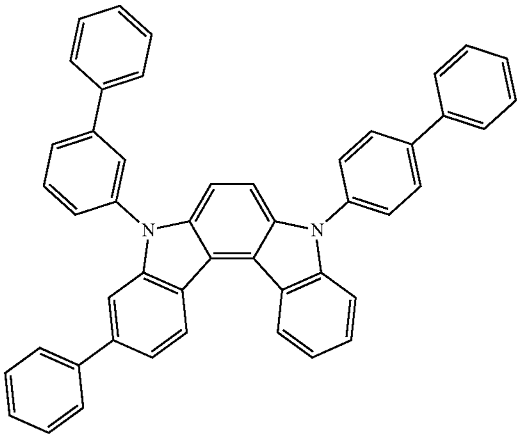
[B-16]
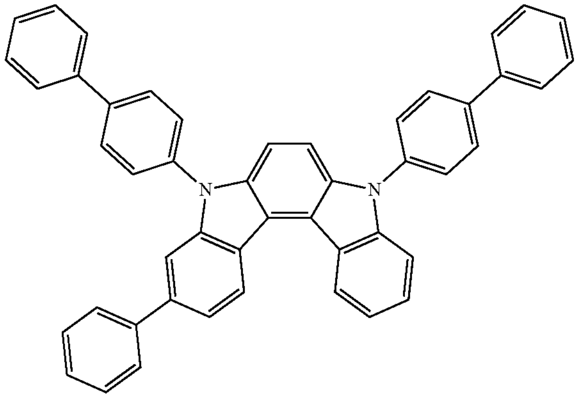
[B-17]
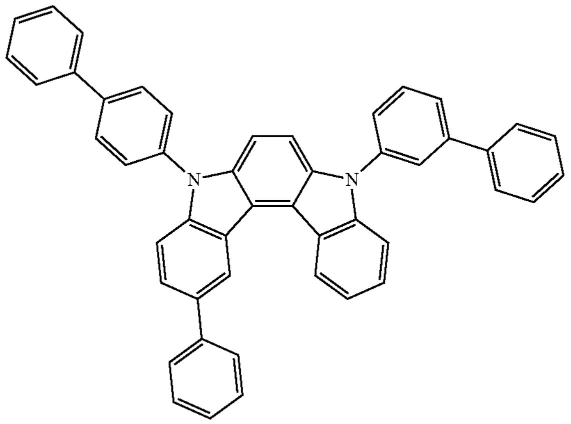
-continued
[B-18]
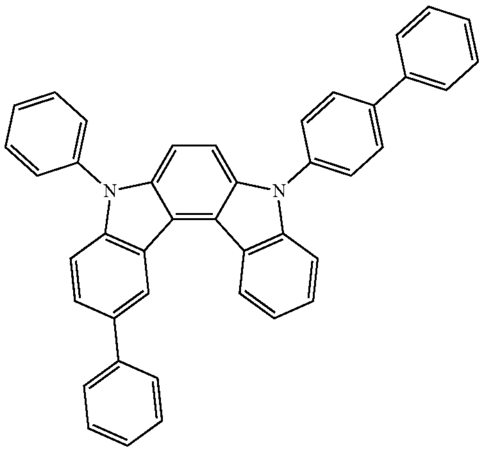
[B-19]
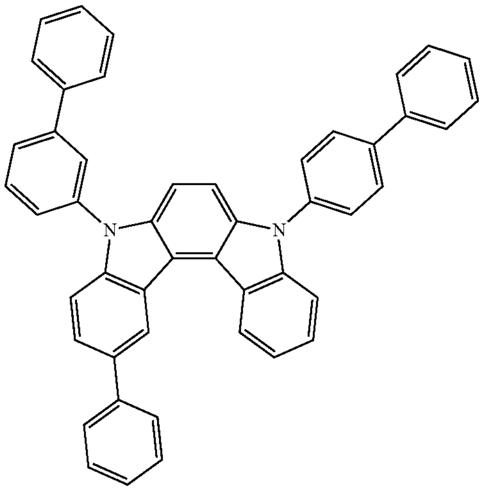
[B-20]
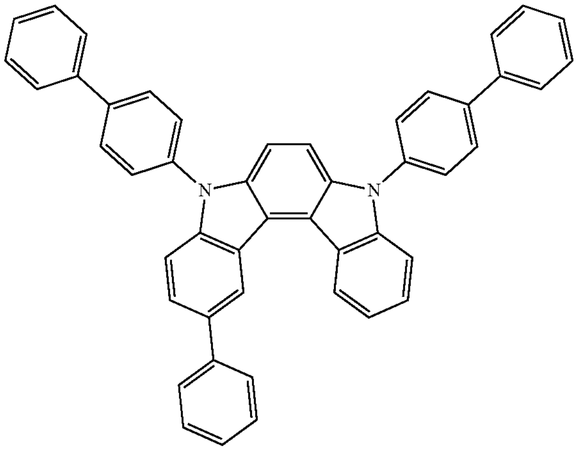

-continued
[B-21]
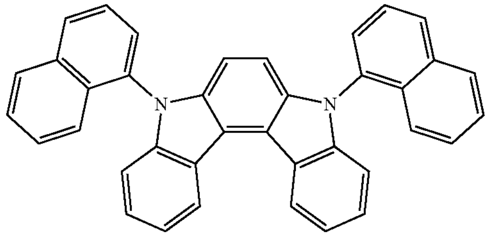
[B-22]
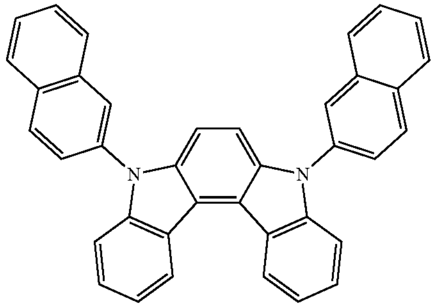
[B-23]
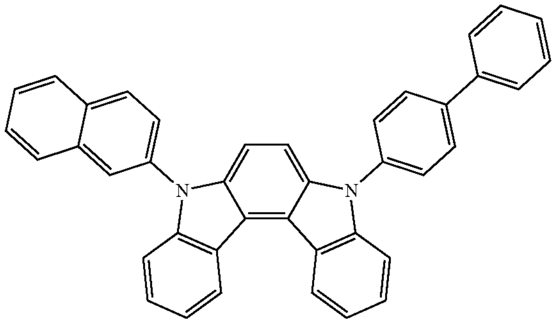
[B-24]
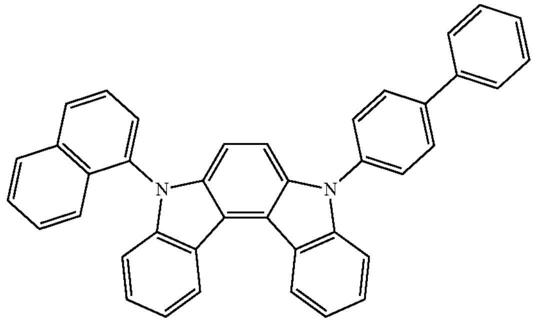
[B-25]
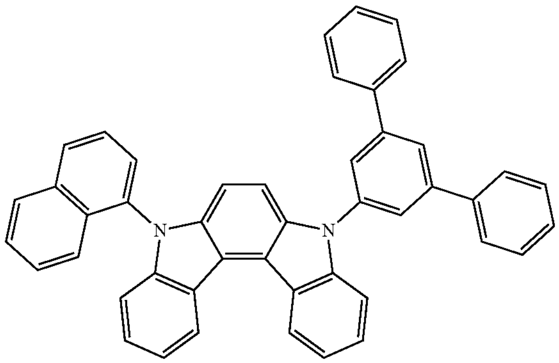
-continued
[B-25]
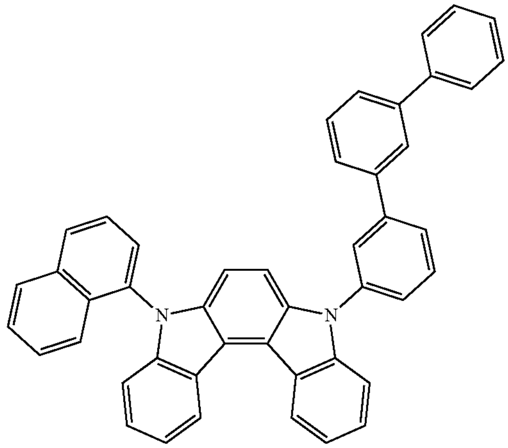
[B-25]
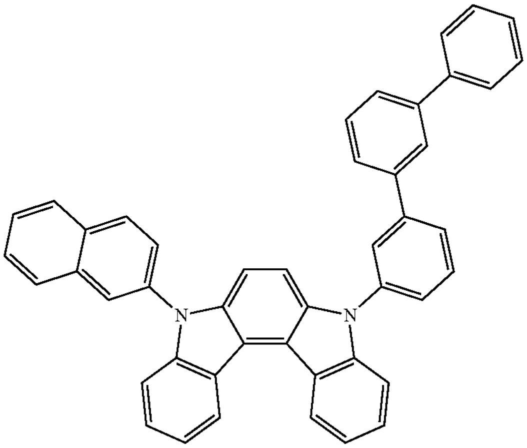
[B-25]
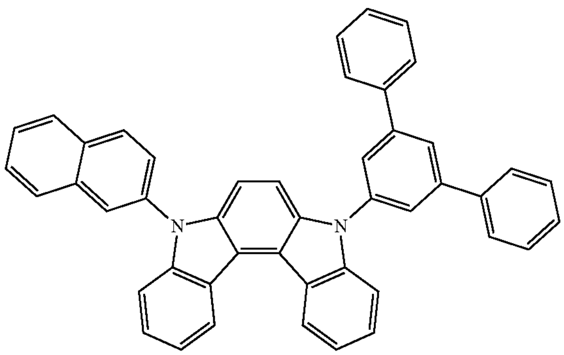

-continued
[B-29]
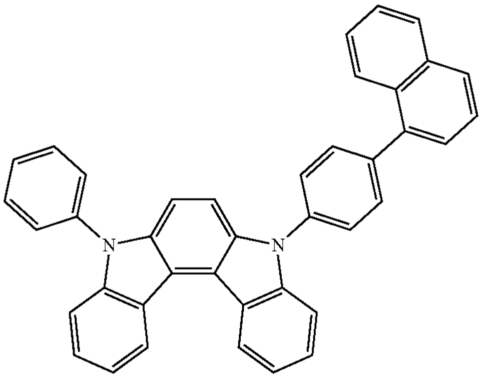
[B-30]
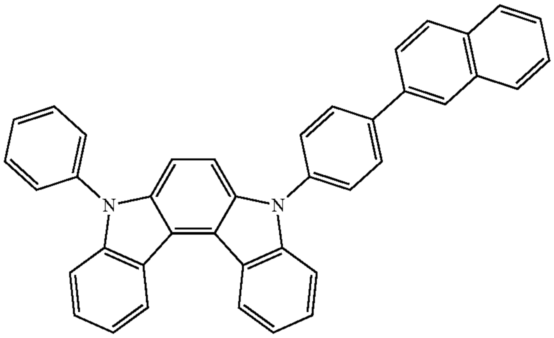
[B-31]
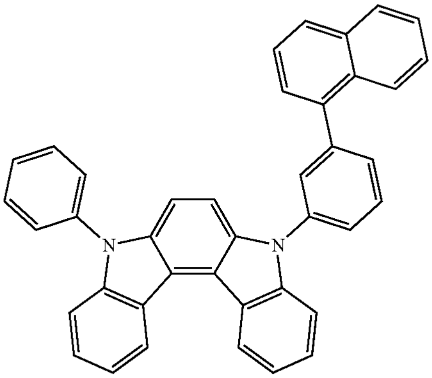
[B-32]
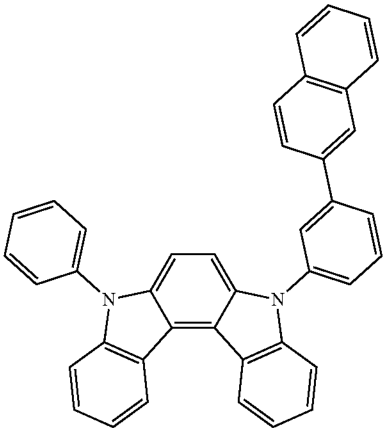
-continued
[B-33]
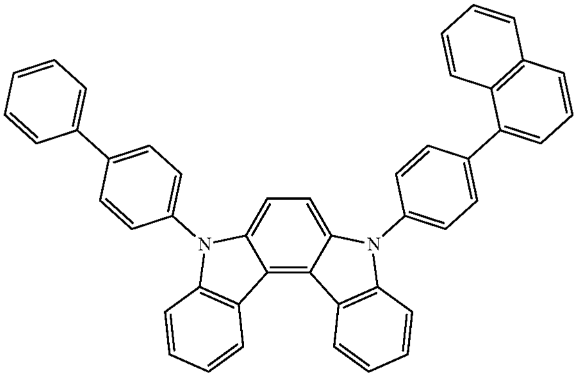
[B-34]
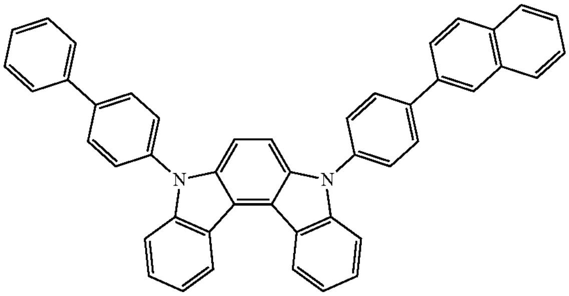
[B-35]
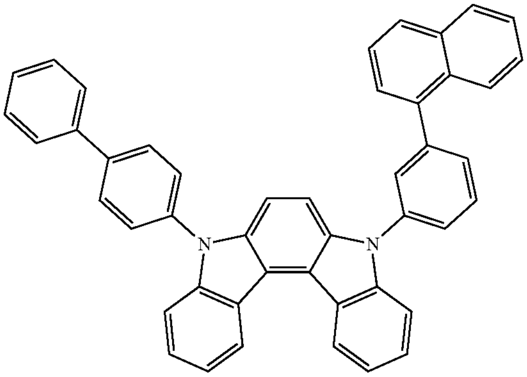
[B-36]
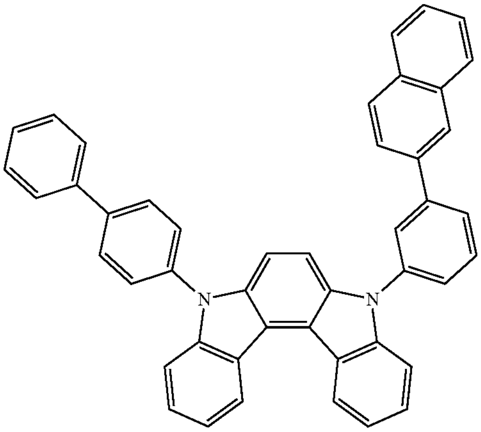

-continued
[B-37]
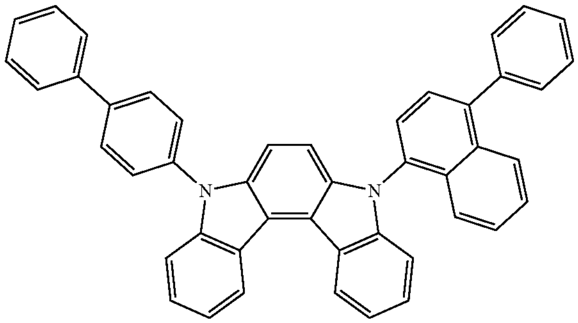
[B-38]
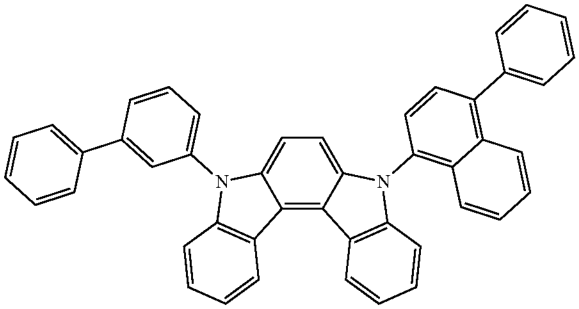
[B-39]
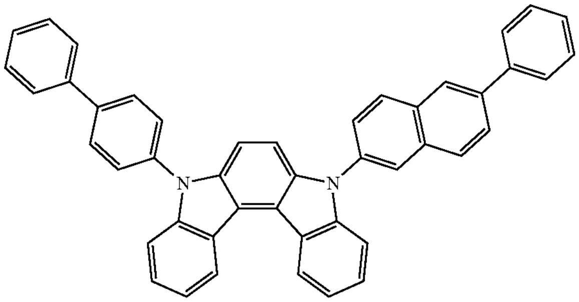
[B-40]
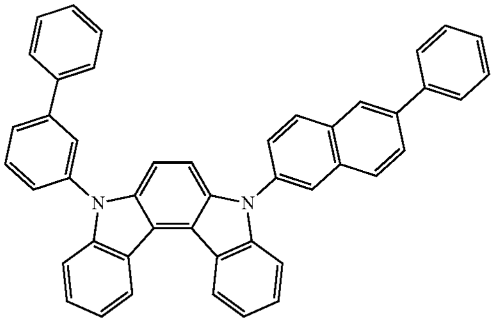
-continued
[B-41]
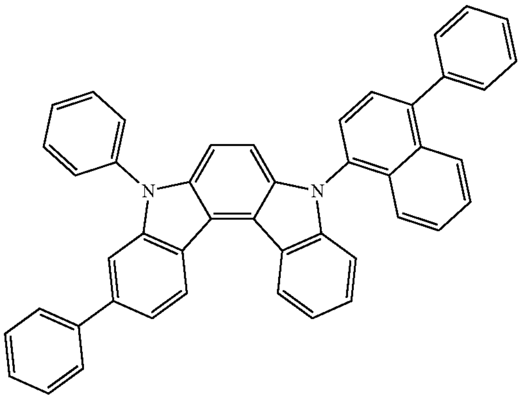
[B-42]
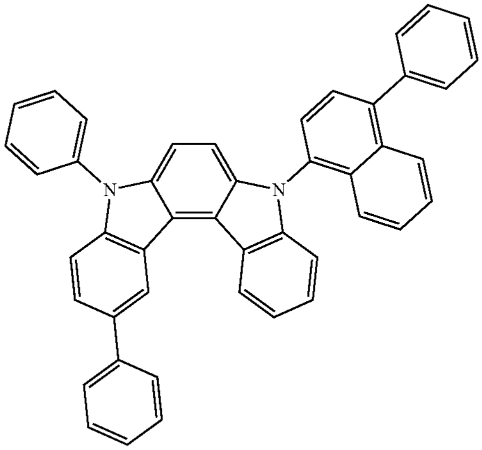
[B-43]
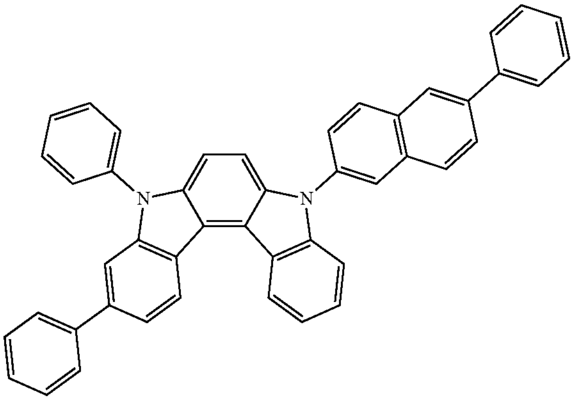

-continued
[B-44]
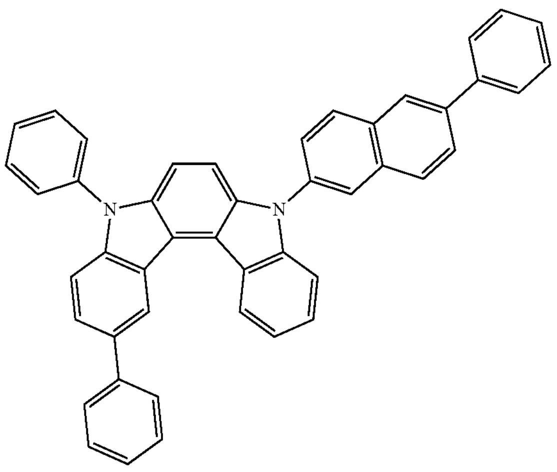
[B-45]
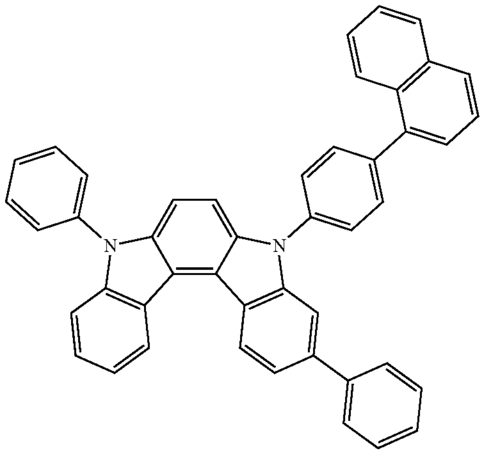
[B-46]
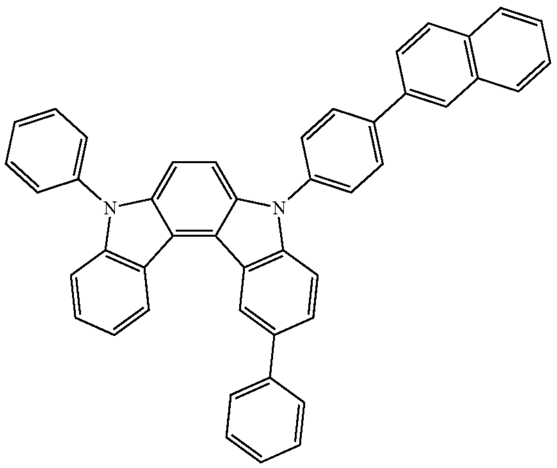
-continued
[B-47]
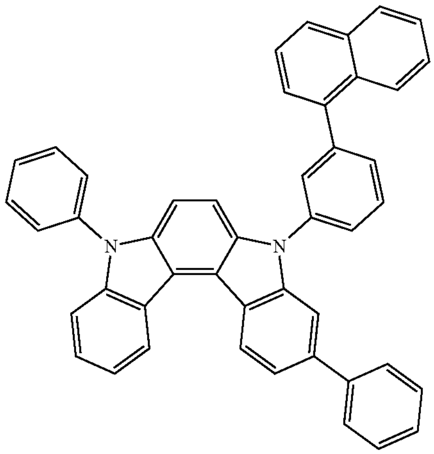
[B-48]
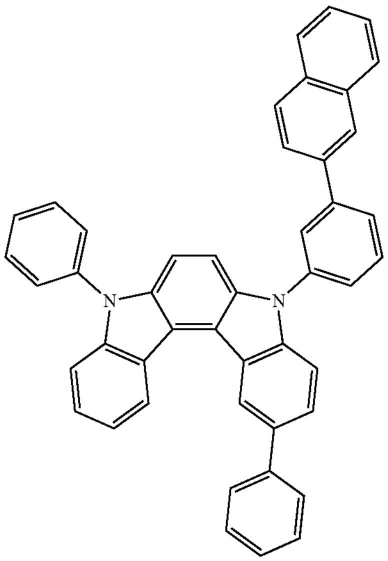
[B-49]
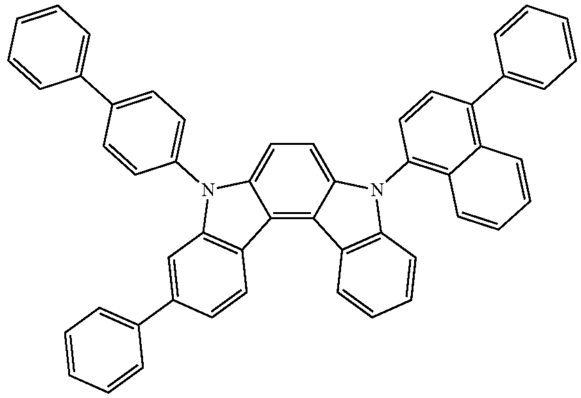

-continued
[B-50]
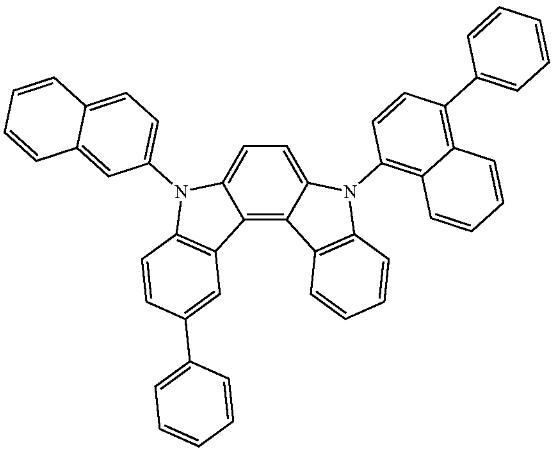
[B-51]
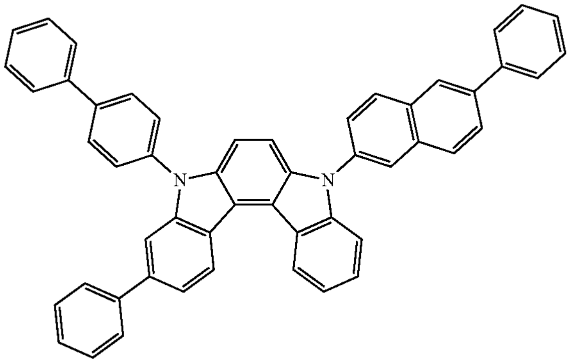
[B-52]
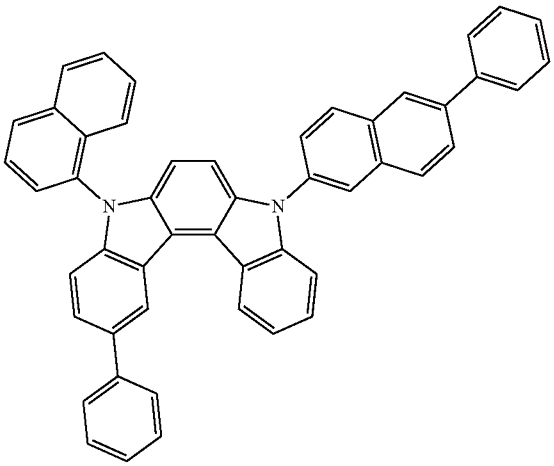
-continued
[B-53]
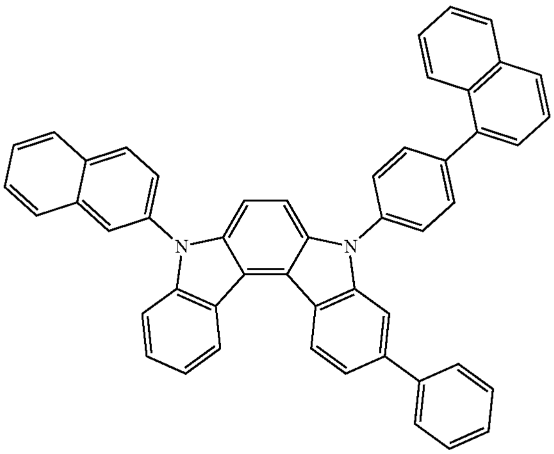
[B-54]
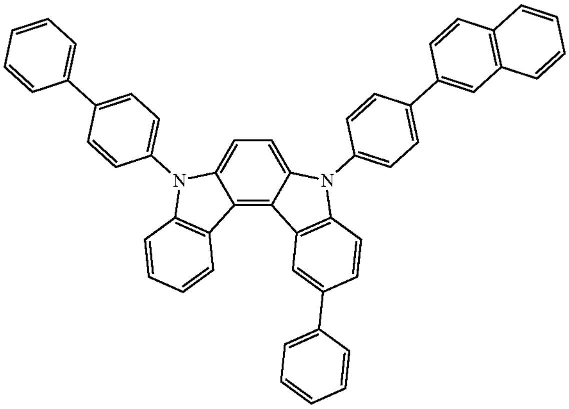
[B-55]
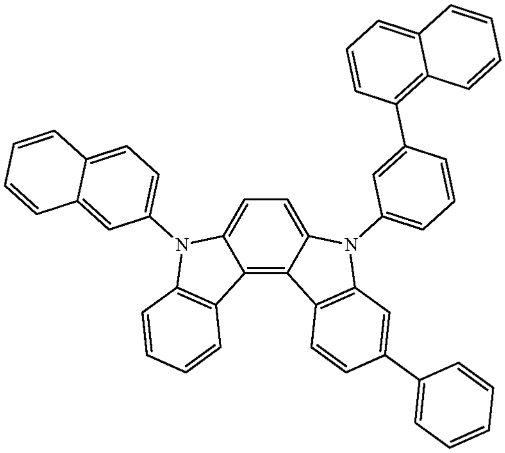

-continued

[B-56]

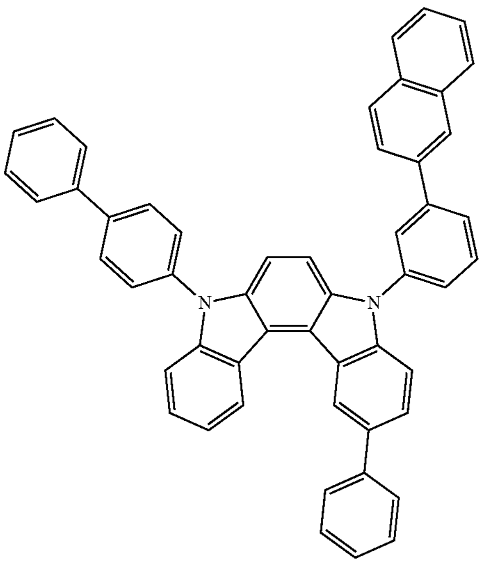

The compound for a first organic optoelectronic device and the compound for a second organic optoelectronic device may be for example included in a weight ratio of 1:99 to 99:1. Within the above range, an appropriate weight ratio by using the electron transport capability of the first compound for an organic optoelectronic device and the hole transport capability of the second compound for an organic optoelectronic device may be matched to implement bipolar characteristics and thus to improve efficiency and life-span. Within the range, for example, they may be included in a weight ratio of about 10:90 to 90:10, about 20:80 to 80:20, for example about 20:80 to about 70:30, about 20:80 to about 60:40, and about 20:80 to about 50:50. For example, they may be included in a weight ratio of 20:80 to 40:60, and as a specific example, it may be included in a weight ratio of 30:70, 40:60 or 50:50, for example, 30:70.

In addition to the aforementioned first compound for an organic optoelectronic device and second compound for an organic optoelectronic device, one or more compounds may be further included.

The aforementioned compound for an organic optoelectronic device or composition for an organic optoelectronic device may be a composition that further includes a dopant.

The dopant may be, for example, a phosphorescent dopant, for example, a red, green, or blue phosphorescent dopant, for example, a red or green phosphorescent dopant.

The dopant is mixed with the compound for an organic optoelectronic device or composition in a small amount to cause light emission, and may be generally a material such as a metal complex that emits light by multiple excitation into a triplet or more. The dopant may be, for example an inorganic, organic, or organic/inorganic compound, and one or more types thereof may be used.

Examples of the dopant include a phosphorescent dopant, and examples of the phosphorescent dopant may be organometallic compounds including Ir, Pt, Os, Ti, Zr, Hf, Eu, Tb, Tm, Fe, Co, Ni, Ru, Rh, Pd, or a combination thereof. The phosphorescent dopant may be, for example a compound represented by the following Chemical Formula Z, but is not limited thereto.

$L^cMX^c$ [Chemical Formula Z]

In Chemical Formula Z, M is a metal, and $L^c$ and $X^c$ are the same or different and are a ligand to form a complex compound with M.

The M may be, for example Ir, Pt, Os, Ti, Zr, Hf, Eu, Tb, Tm, Fe, Co, Ni, Ru, Rh, Pd, or a combination thereof and the $L^c$ and $X^c$ may be, for example a bidendate ligand.

The aforementioned compound for an organic optoelectronic device or composition for an organic optoelectronic device may provide a film using a dry film-forming method such as chemical vapor deposition.

Hereinafter, an organic optoelectronic device including the aforementioned compound for an organic optoelectronic device or composition for an organic optoelectronic device is described.

The organic optoelectronic device may be any device to convert electrical energy into photoenergy and vice versa without particular limitation, and may be, for example an organic photoelectric device, an organic light emitting diode, an organic solar cell, and an organic photo-conductor drum.

Herein, an organic light emitting diode as one example of an organic optoelectronic device is described referring to drawings.

FIGS. 1 and 2 are cross-sectional views of each organic light emitting diode according to one embodiment.

Referring to FIG. 1, an organic light emitting diode 100 according to an embodiment includes an anode 120 and a cathode 110 facing each other and an organic layer 105 disposed between the anode 120 and cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al, and $BaF_2$/Ca, but is not limited thereto.

The organic layer 105 may include the aforementioned compound for an organic optoelectronic device or composition for an organic optoelectronic device.

The organic layer 105 may include a light emitting layer 130, and the light emitting layer 130 may include the aforementioned compound for an organic optoelectronic device or composition for an organic optoelectronic device.

The composition for an organic optoelectronic device further including the dopant may be, for example, a green light emitting composition.

The light emitting layer 130 may include, for example, the aforementioned first compound for an organic optoelectronic device and second compound for an organic optoelectronic device as phosphorescent hosts, respectively.

The organic layer may further include an auxiliary layer in addition to the light emitting layer.

The auxiliary layer may be, for example, a hole auxiliary layer 140.

Referring to FIG. 2, an organic light emitting diode 200 further includes a hole auxiliary layer 140 as well as the light emitting layer 130. The hole auxiliary layer 140 may further increase hole injection and/or hole mobility between the anode 120 and the light emitting layer 130 and block electrons.

The hole auxiliary layer 140 may include, for example, at least one of compounds of Group D.

Specifically, the hole auxiliary layer 140 may include a hole transport layer between the anode 120 and the light emitting layer 130, and a hole transport auxiliary layer between the light emitting layer 130 and the hole transport layer, and at least one of the compounds of Group D may be included in the hole transport auxiliary layer.

[Group D]

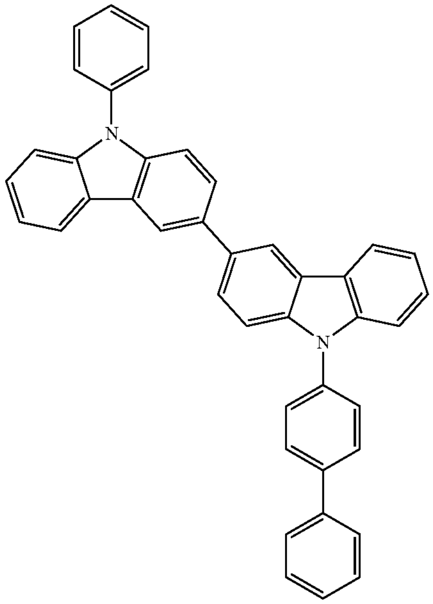

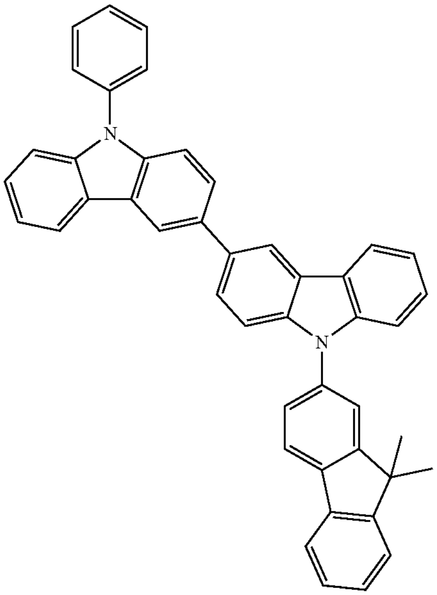

-continued

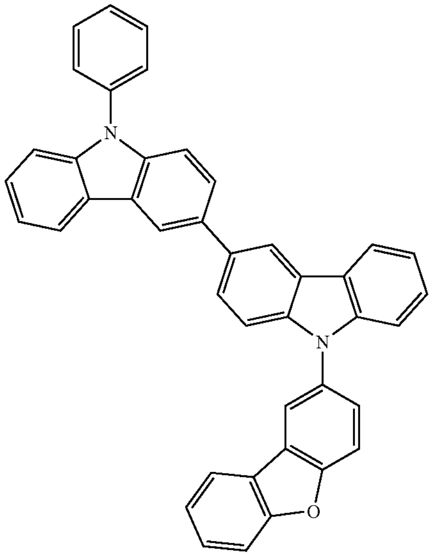

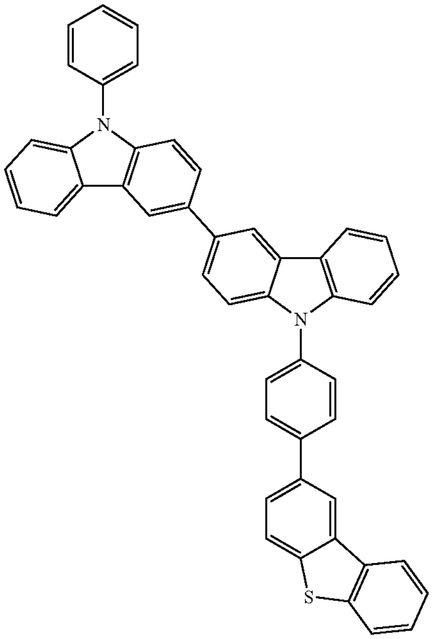

-continued
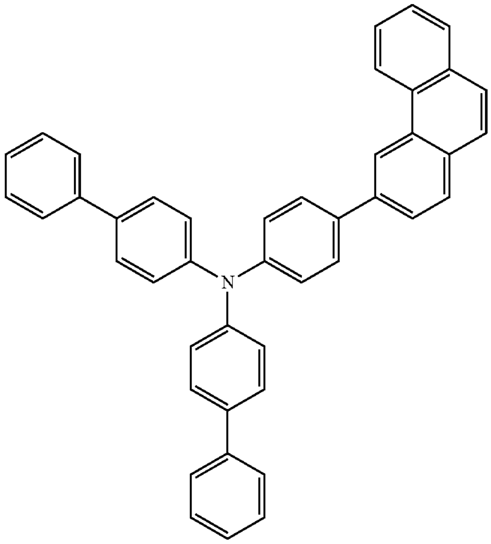
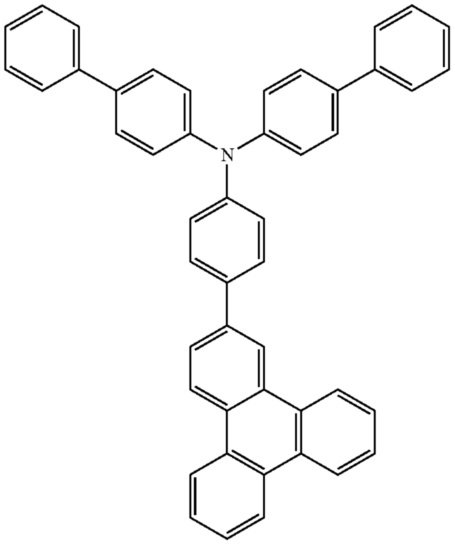
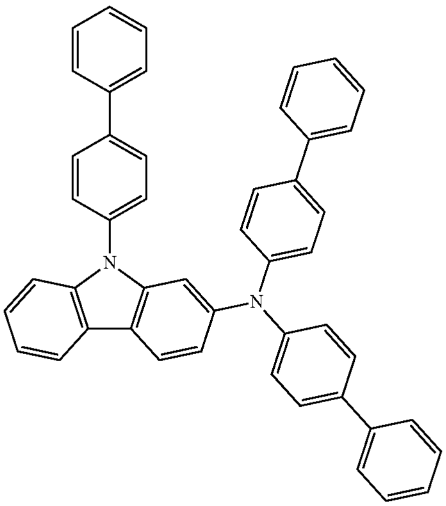
-continued
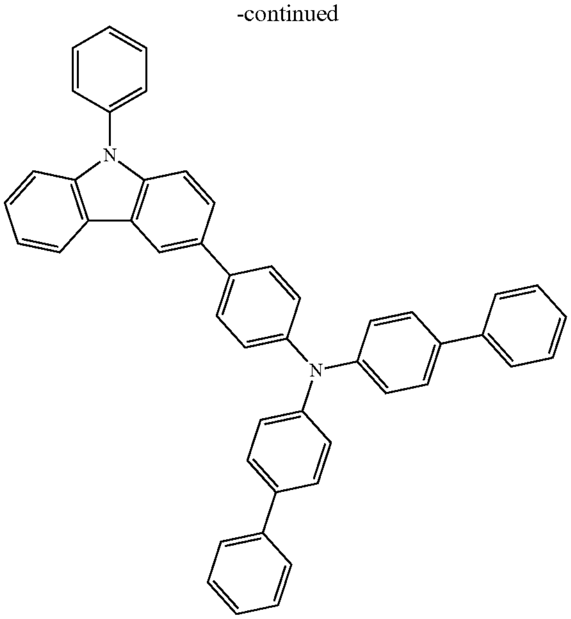
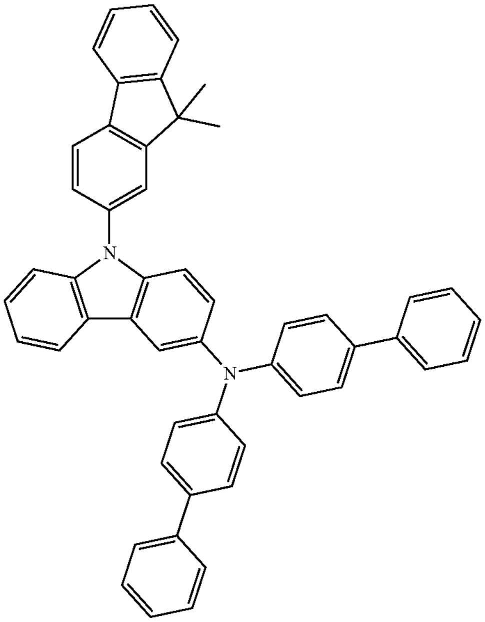

-continued
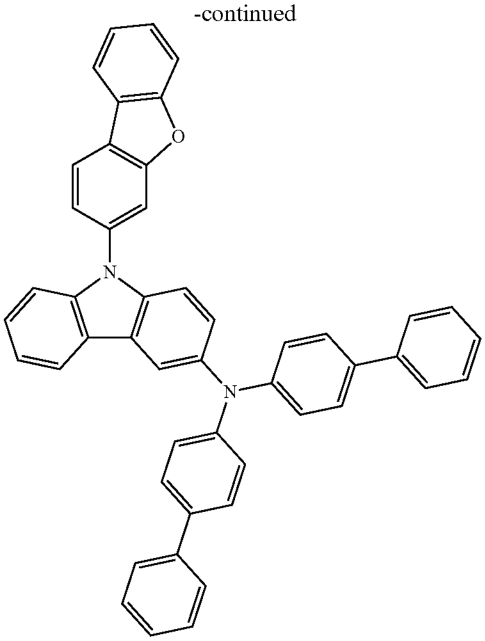
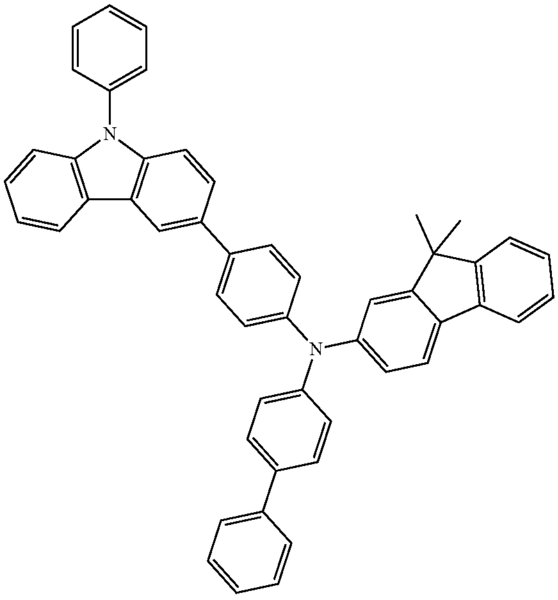
-continued
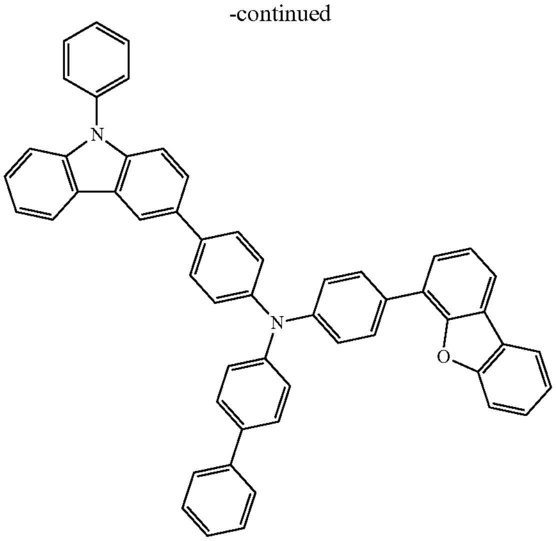
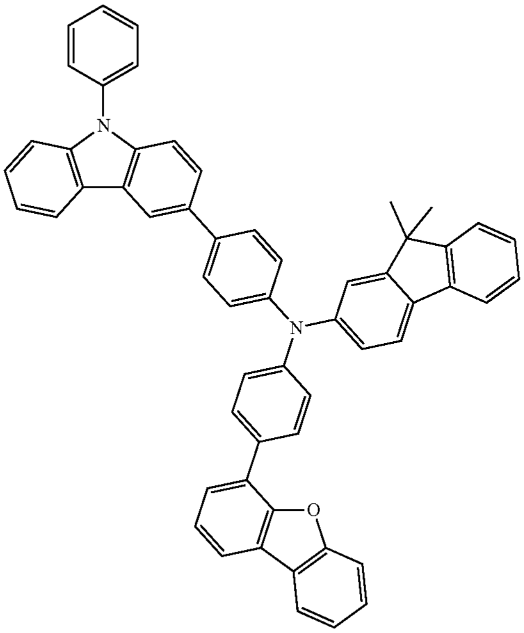
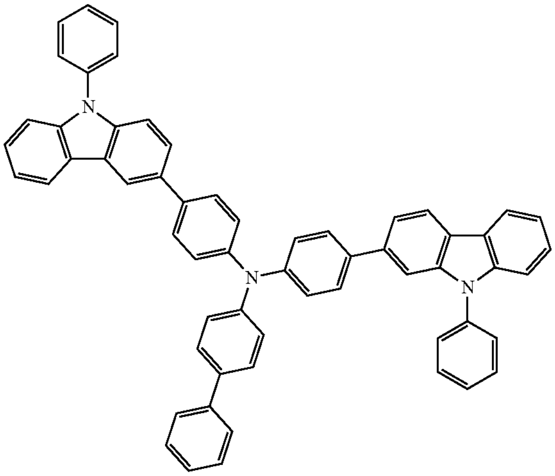

-continued
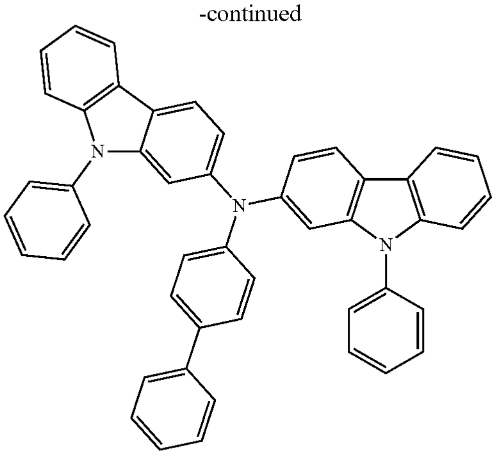
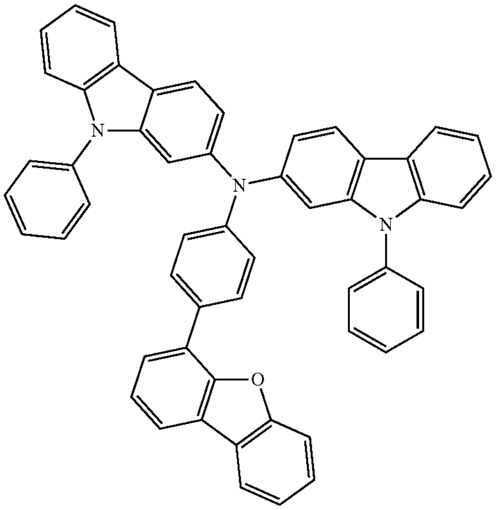
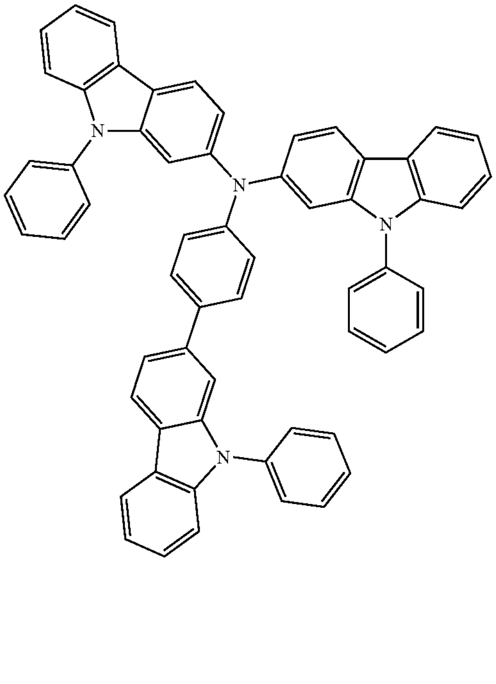
-continued
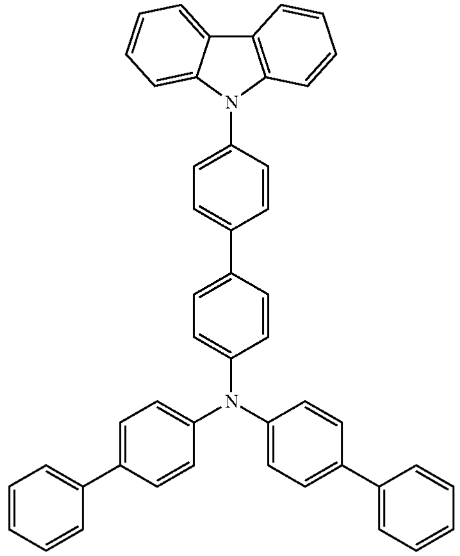
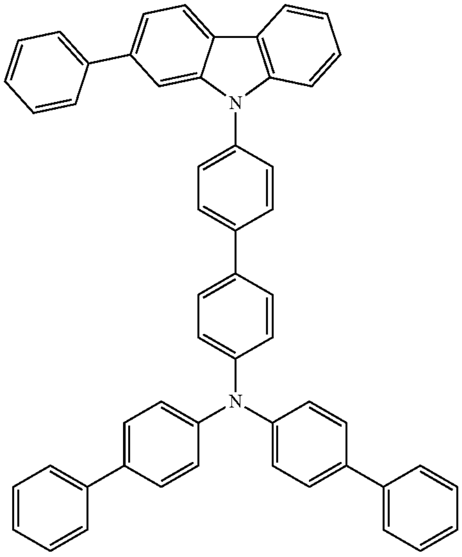
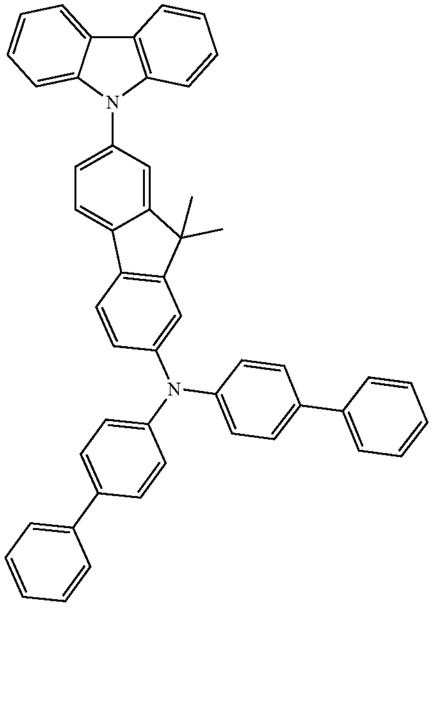

-continued
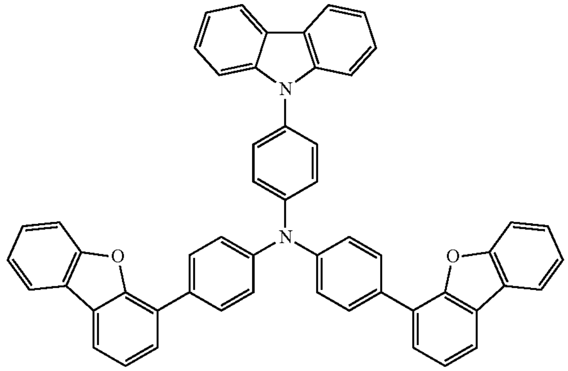
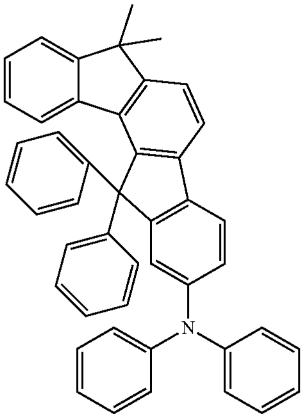
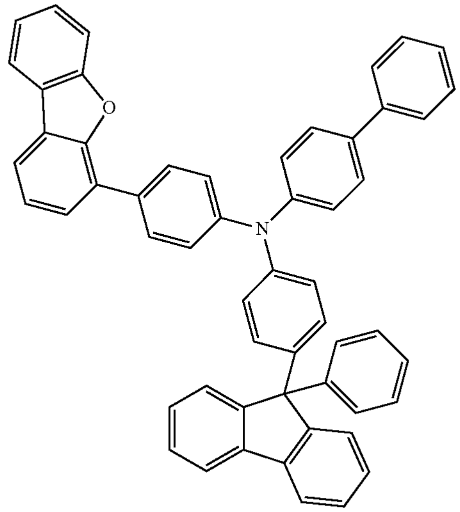
-continued
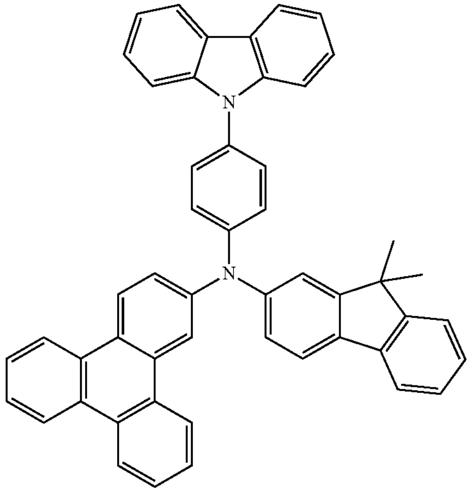
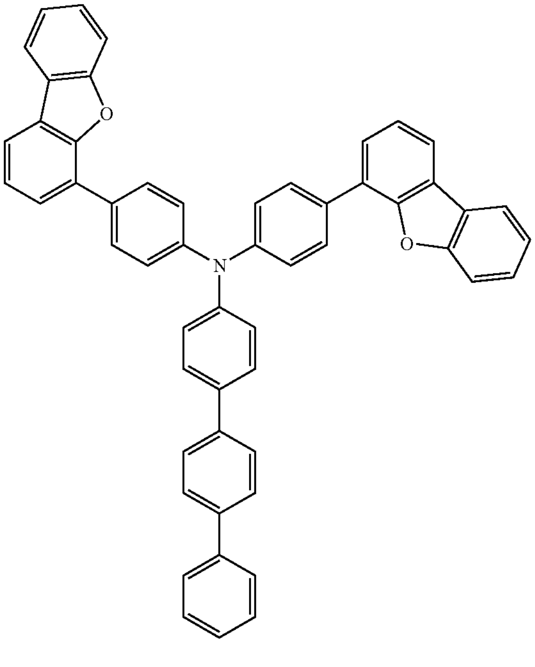
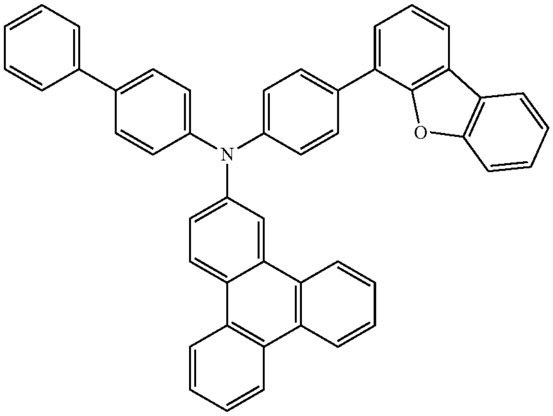

-continued
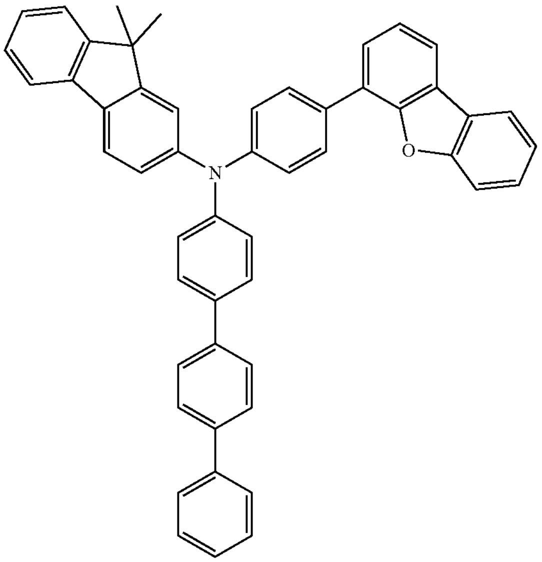
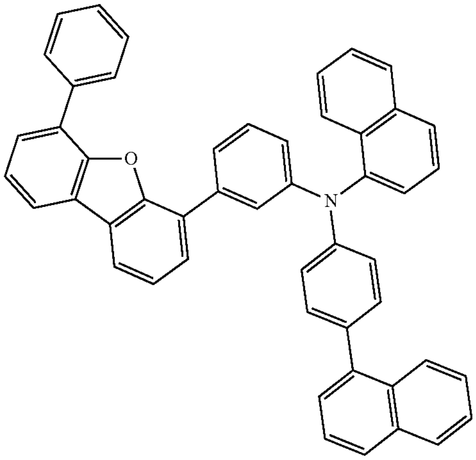
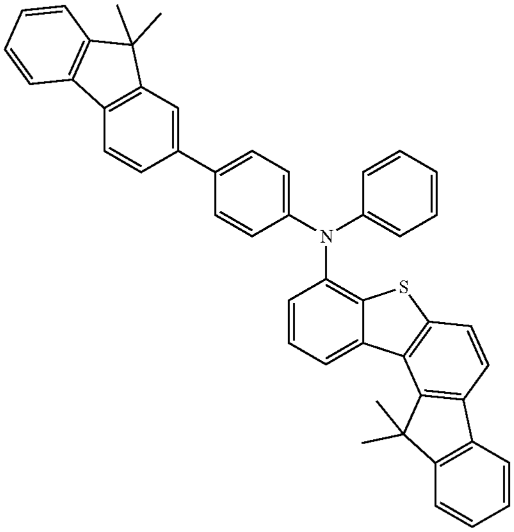
-continued
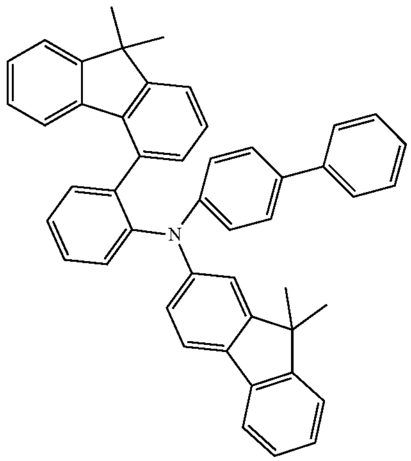
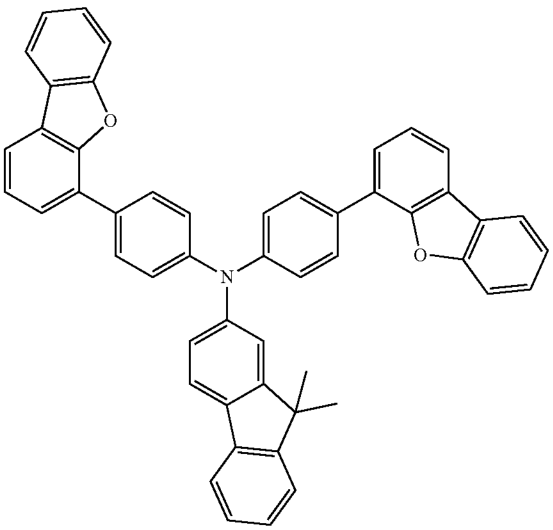
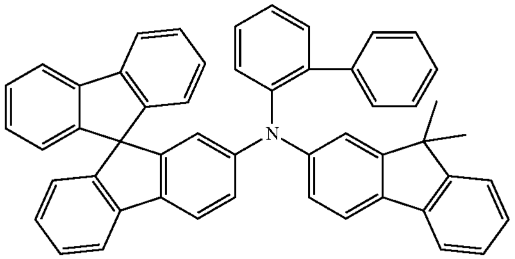

-continued
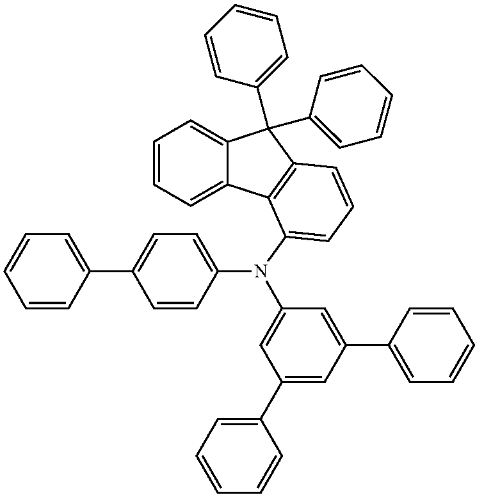
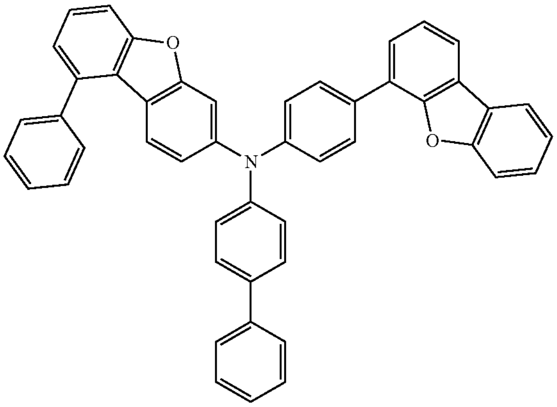
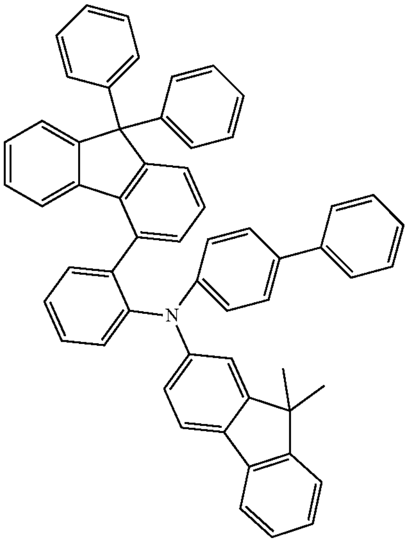
-continued
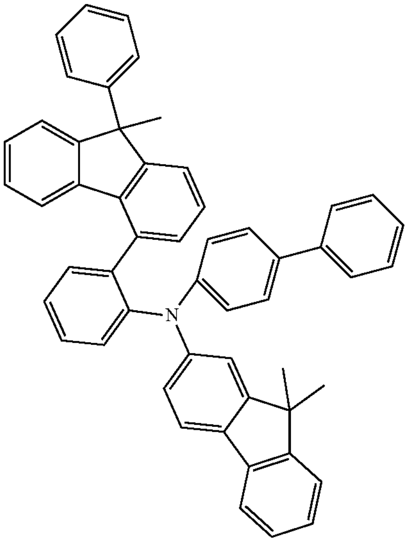
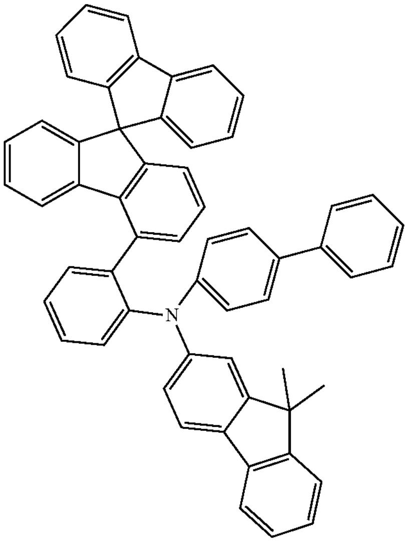
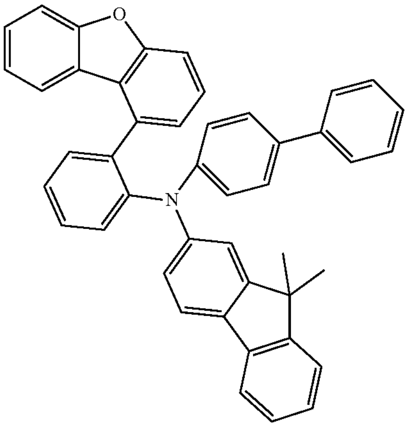

-continued
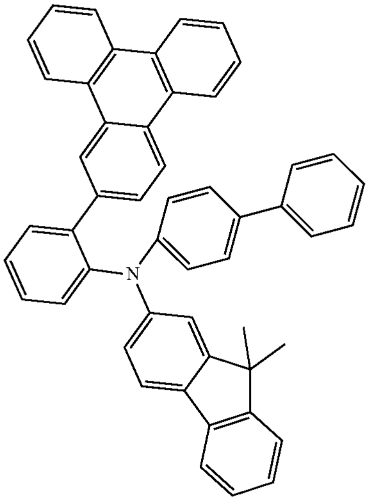
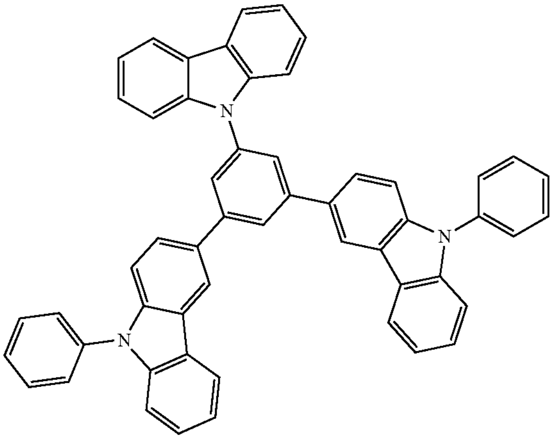
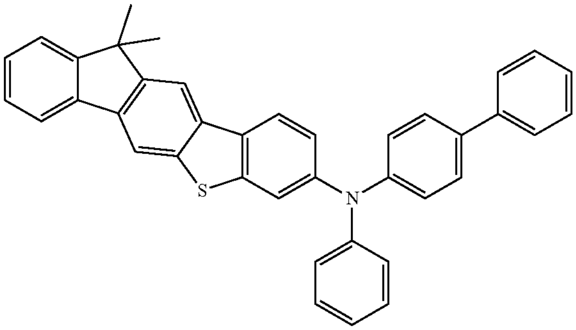
-continued
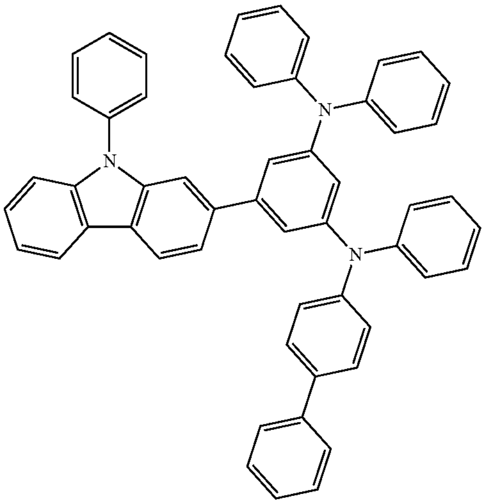
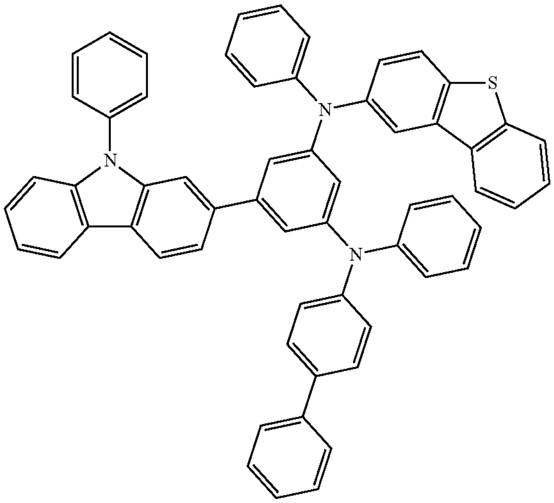
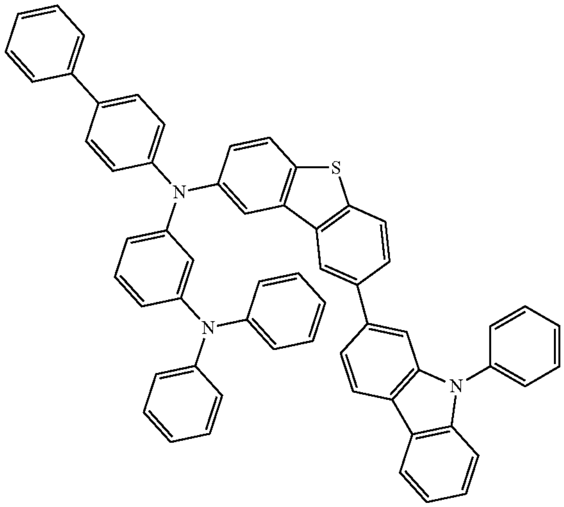

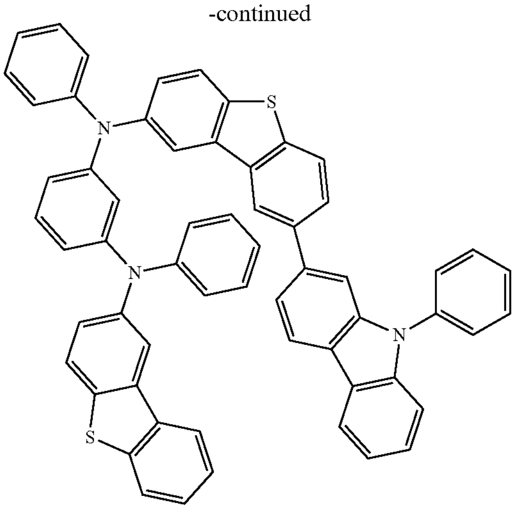
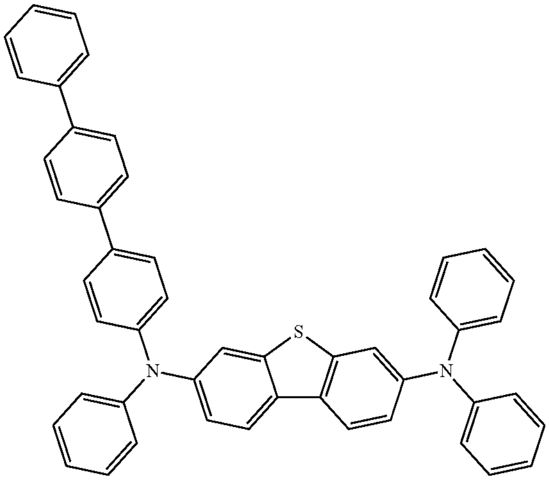
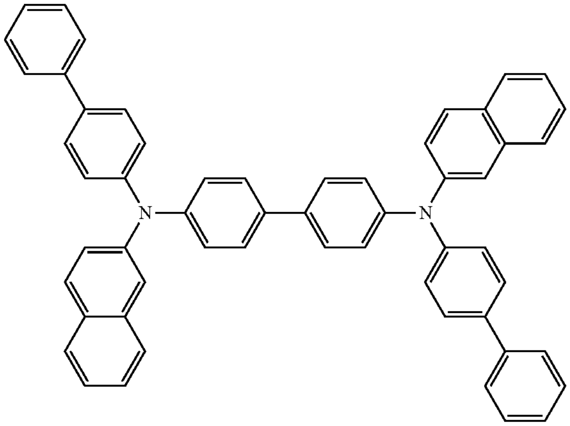
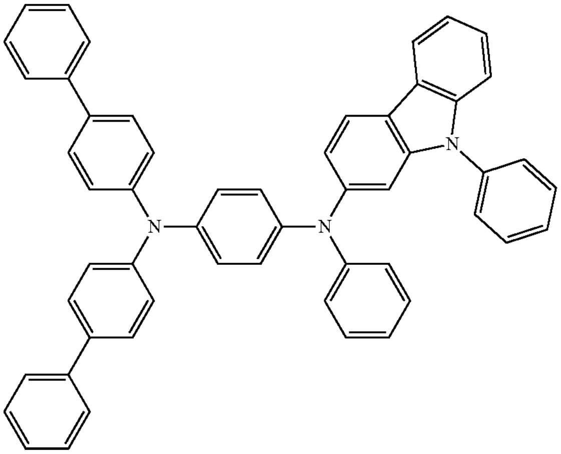
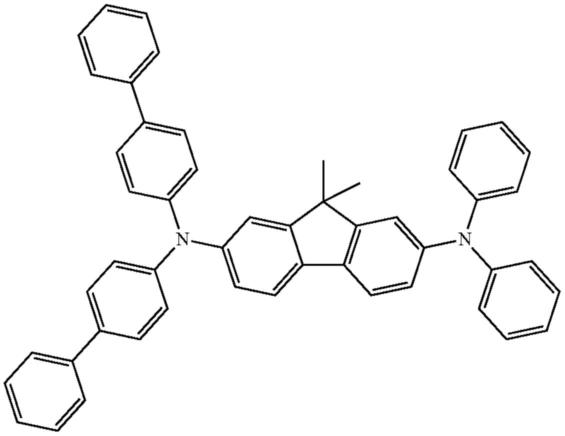
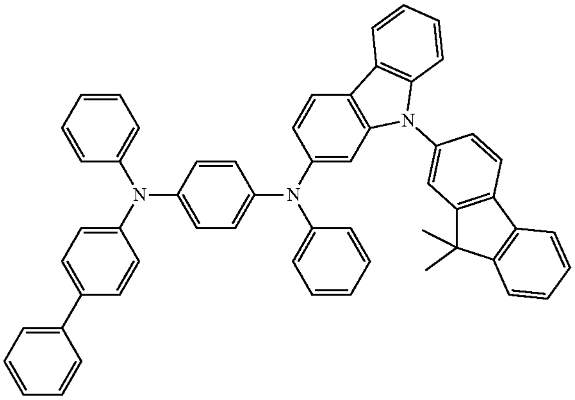

-continued
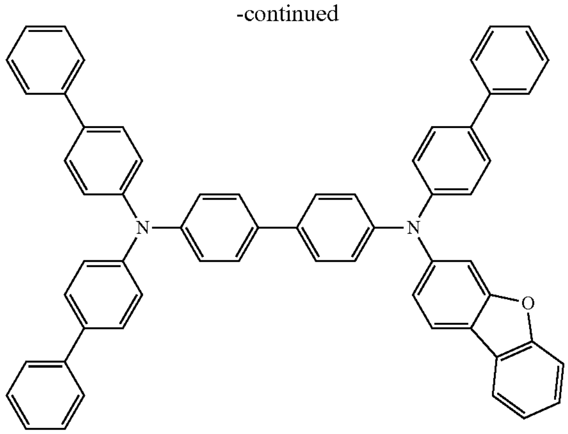
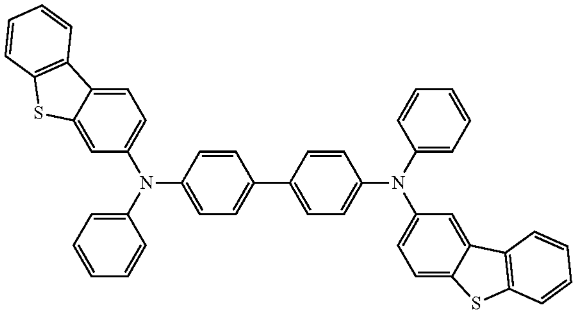
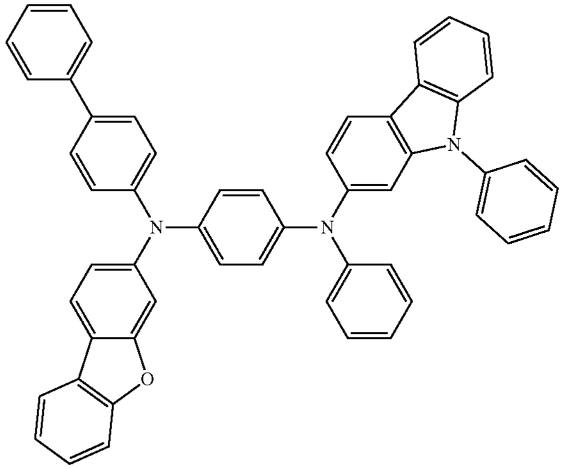
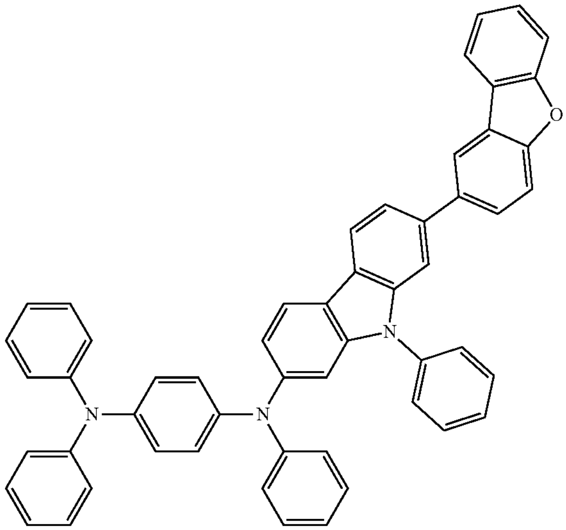
-continued
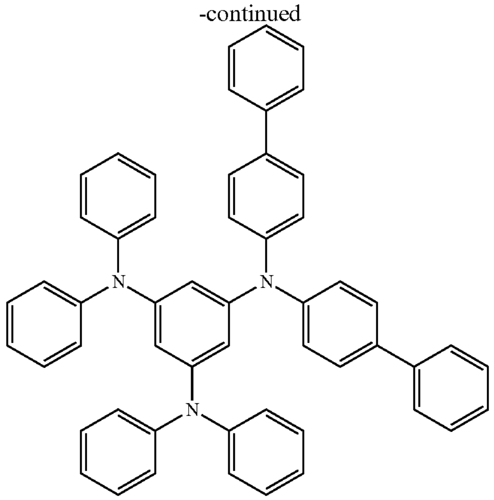
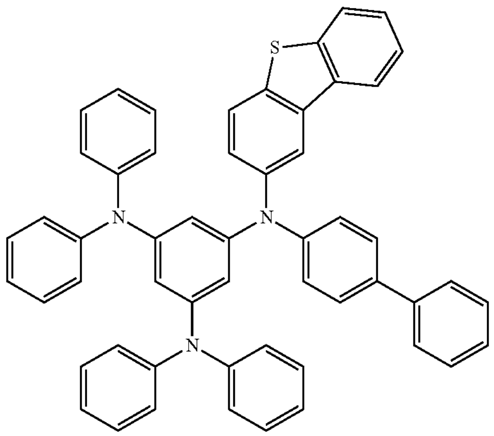
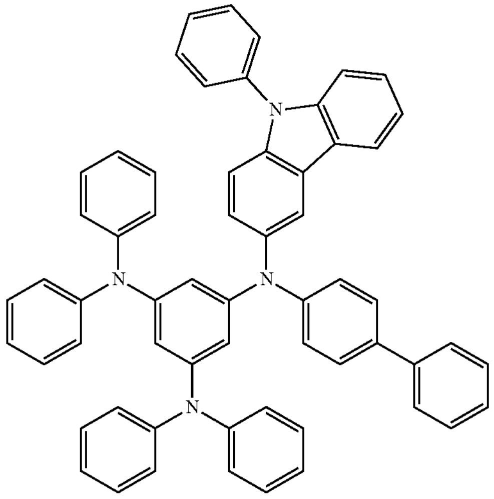

-continued
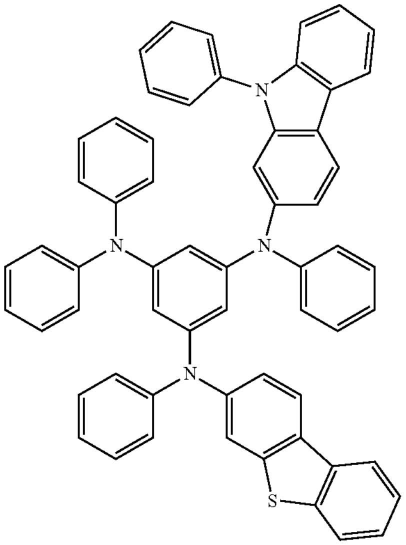
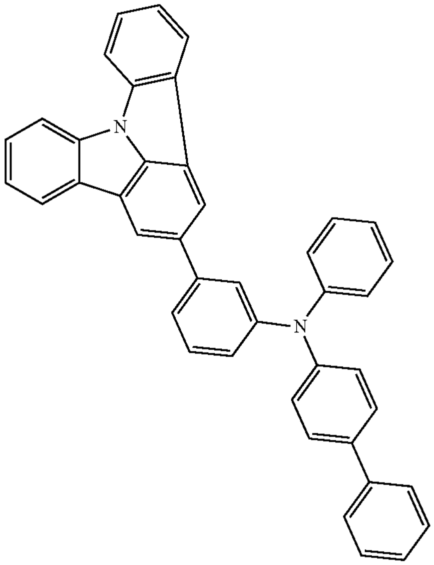
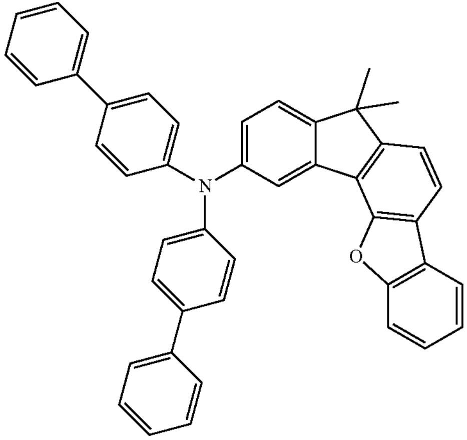
-continued
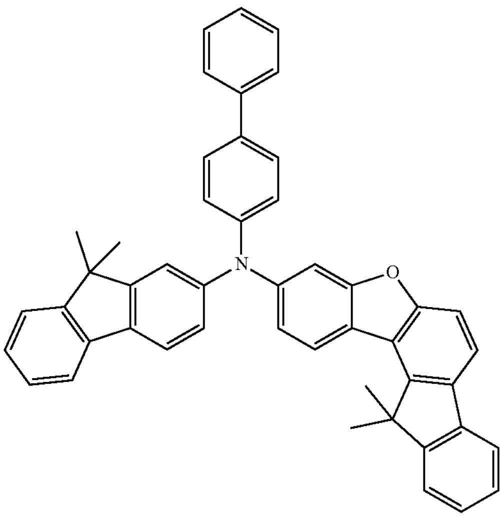
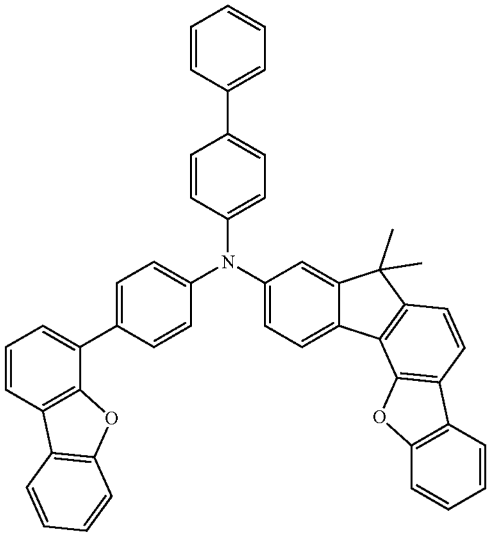
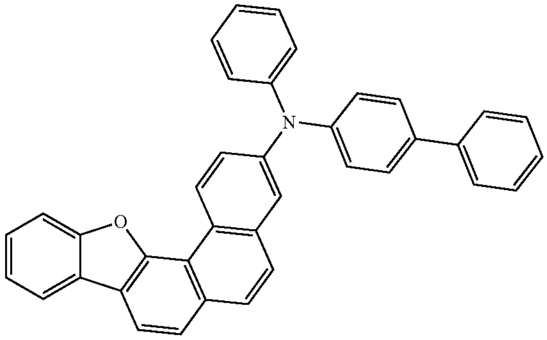

-continued
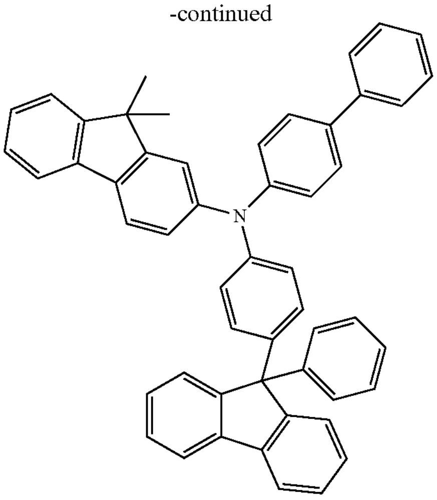
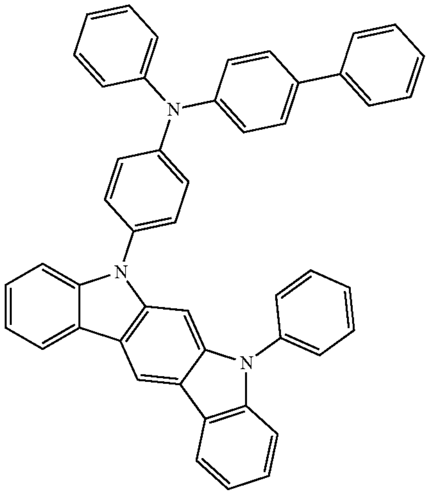
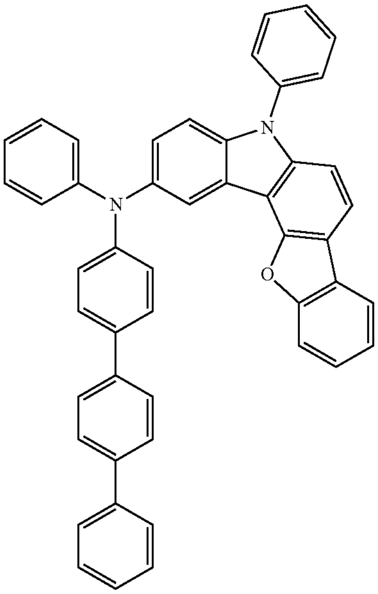
-continued
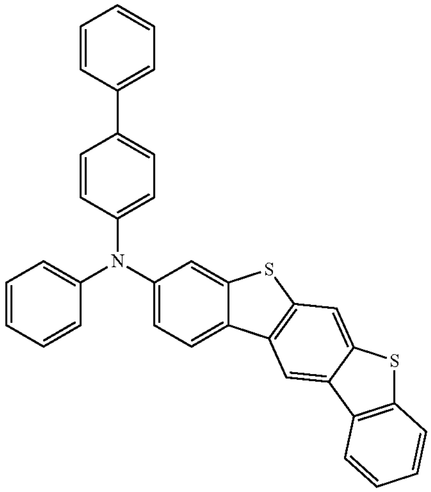
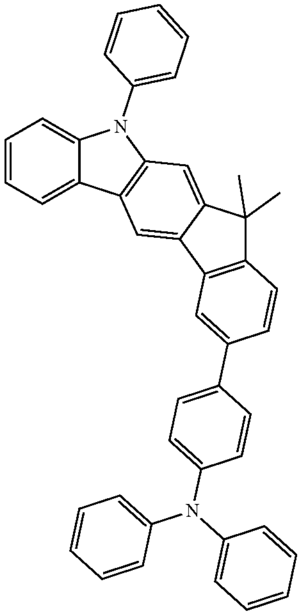
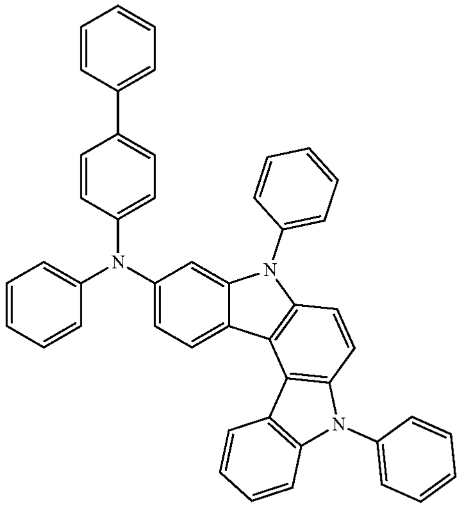

-continued

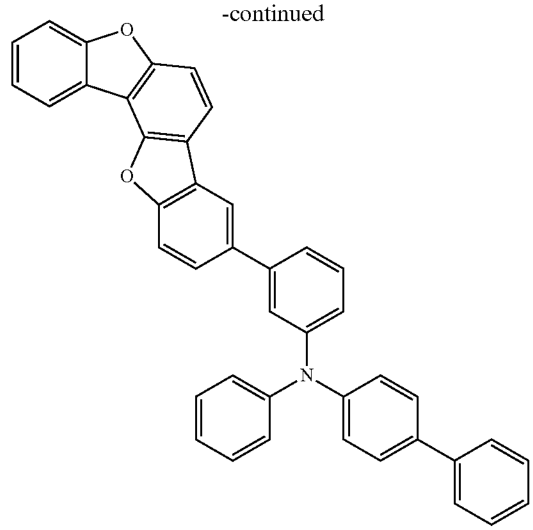

In the hole transport auxiliary layer, known compounds disclosed in U.S. Pat. No. 5,061,569A, JP1993-009471A, WO1995-009147A1, JP1995-126615A, JP1998-095973A, and the like and compounds similar thereto may be used in addition to the aforementioned compounds.

In an embodiment, in FIG. 1 or 2, an organic light emitting diode may further include an electron transport layer, an electron injection layer, or a hole injection layer as the organic layer 105.

The organic light emitting diodes 100 and 200 may be produced by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

Hereinafter, the embodiments are illustrated in more detail with reference to examples. However, these examples are exemplary, and the present scope is not limited thereto.

MODE FOR INVENTION

Hereinafter, starting materials and reactants used in Examples and Synthesis Examples were purchased from Sigma-Aldrich Co. Ltd., TCI Inc., Tokyo chemical industry or P&H tech as far as there in no particular comment or were synthesized by known methods.

(Preparation of Compound for Organic Optoelectronic Device)

The compound presented as a more specific example of the compound of the present invention was synthesized through the following steps.

(Preparation of First Compound for Organic Optoelectronic Device)

Synthesis Example 1: Synthesis of Compound A-6

[Reaction Scheme 1]

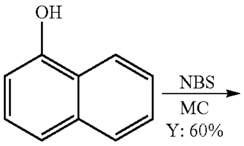

-continued

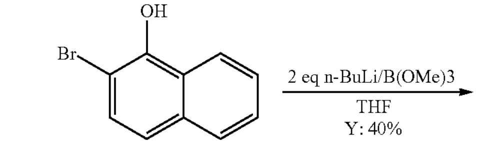

A-6-1

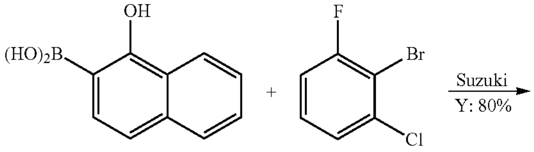

A-6-2

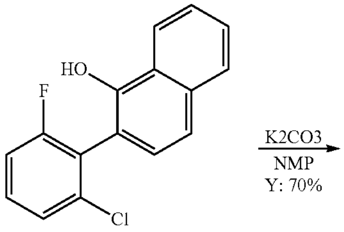

A-6-3

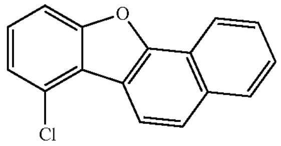

A-6-4

[Reaction Scheme 2]

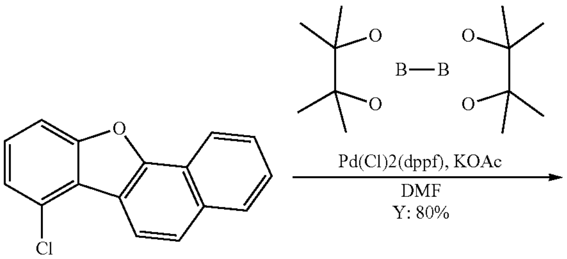

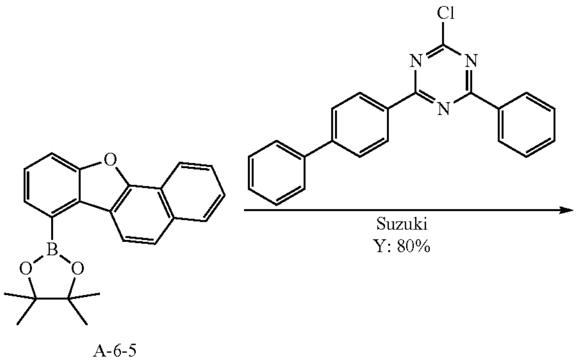

A-6-5

-continued

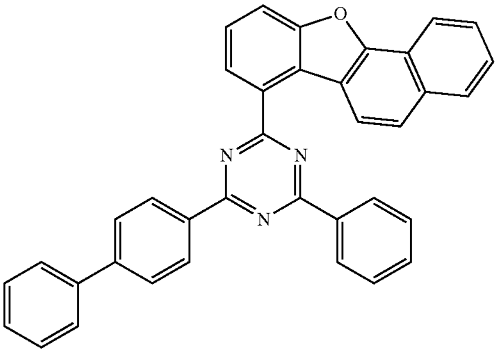

A-6

HRMS (70 eV, EI+): m/z calcd for C37H23N3O: 525.18, found: 526.33

Synthesis Example 2: Synthesis of Compound A-7

[Reaction Scheme 3]

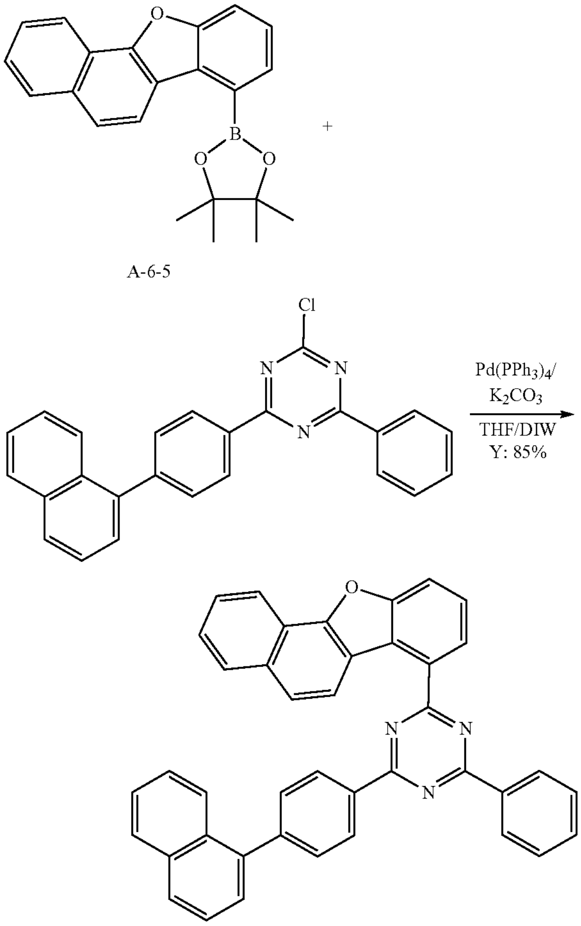

A-6-5

A-7

HRMS (70 eV, EI+): m/z calcd for C41H25N3O: 575.20, found: 576.33

Synthesis Example 3: Synthesis of Compound A-5

[Reaction Scheme 4]

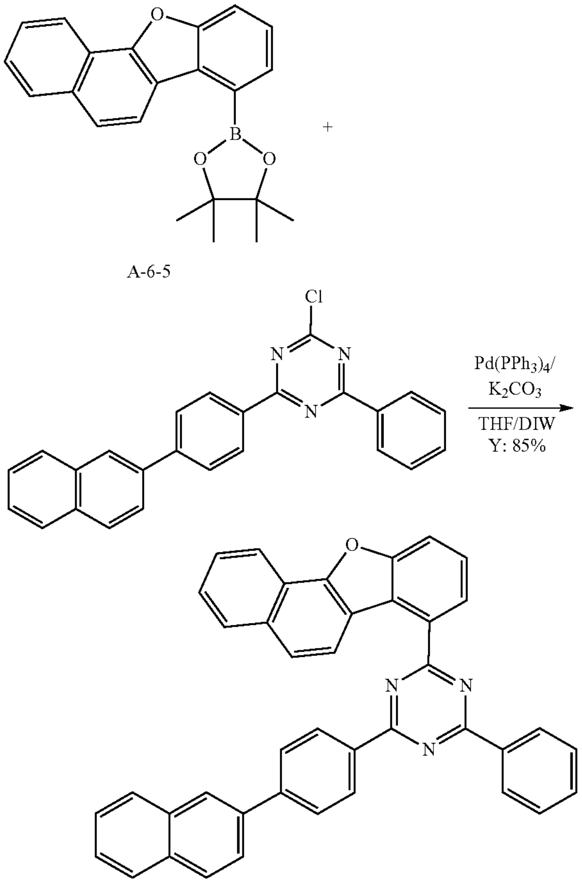

A-6-5

A-5

HRMS (70 eV, EI+): m/z calcd for C41H25N3O: 575.20, found: 576.39

Synthesis Example 4: Synthesis of Compound B-34

Compound B-34 was synthesized with reference to the disclosures disclosed in KR10-2018-0129656A.

[B-34]

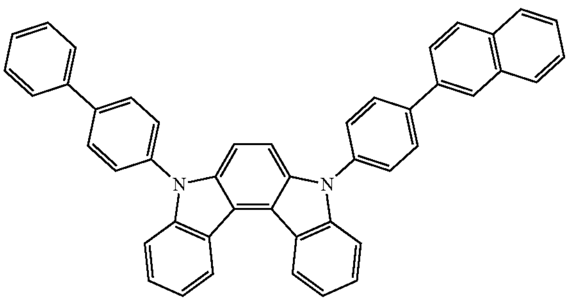

HRMS (70 eV, EI+): m/z calcd for C45H27N3O: 610.24, found: 611.24

Comparative Synthesis Example 1: Synthesis of Compound C-1

Compound C-1 was synthesized with reference to the disclosures disclosed in KR10-1970000 B1.

C-1

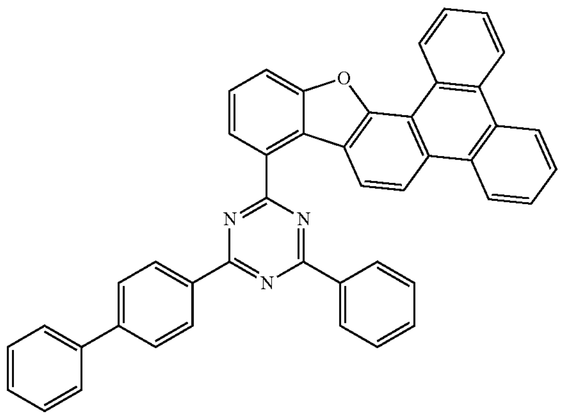

HRMS (70 eV, EI+): m/z calcd for C45H27N3O: 625.22, found: 626.20

Comparative Synthesis Example 2: Synthesis of Compound C-2

[Reaction Scheme 5]

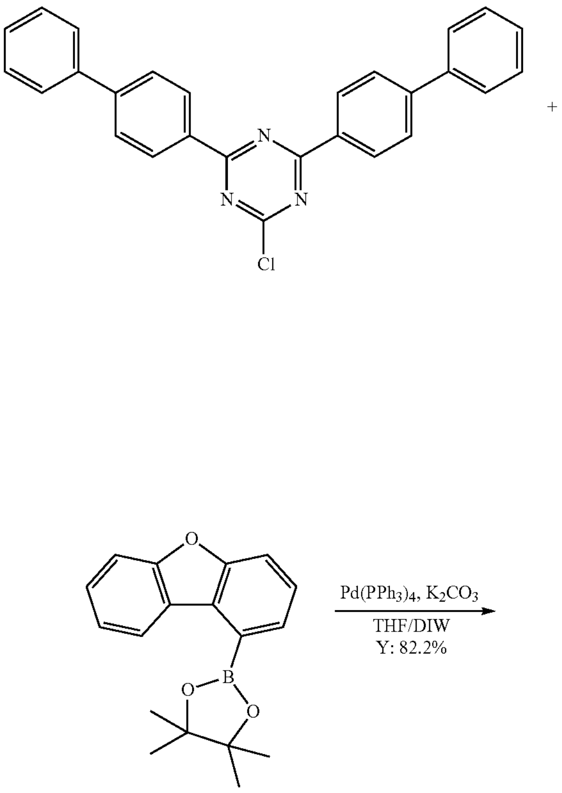

-continued

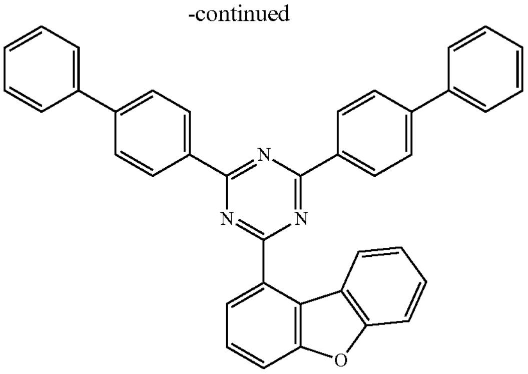

C-2

HRMS (70 eV, EI+): m/z calcd for C39H25N3O: 551.20, found: 552.20

(Manufacture of Organic Light Emitting Diode)

Example 1

A glass substrate coated with ITO (Indium tin oxide) with a thickness of 1500 Å was washed with distilled water ultrasonically. After washing with the distilled water, the glass substrate was washed with a solvent such as isopropyl alcohol, acetone, methanol, and the like ultrasonically and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 700 Å-thick to form a hole transport layer. On the hole transport layer, Compound C-1 was vacuum-deposited to form a 400 Å-thick hole transport auxiliary layer. On the hole transport auxiliary layer, 400 Å-thick light emitting layer was formed by using Compound A-6 as a host and doping 2 wt % of [Ir(piq)$_2$acac] as a dopant by a vacuum-deposition. Subsequently, on the light emitting layer, a 300 Å-thick electron transport layer was formed by simultaneously vacuum-depositing Compound D and Liq in a ratio of 1:1, and on the electron transport layer, Liq and Al were sequentially vacuum-deposited to be 15 Å-thick and 1200 Å-thick, producing an organic light emitting diode.

The organic light emitting diode had a five-layered organic thin layer, and specifically the following structure.

ITO/Compound A (700 Å)/Compound B (50 Å)/Compound C (700 Å)/Compound C-1 (400 Å)/EML [Compound A-6:[Ir(piq)$_2$acac] (2 wt %)] (400 Å)/Compound D: Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN)

Compound C: N-(biphenyl-4-yl)-9,9-dimethyl-N-(4-(9-phenyl-9H-carbazol-3-yl)phenyl)-9H-fluoren-2-amine Compound C-1: N, N-di([1,1'-biphenyl]-4-yl)-7,7-dimethyl-7H-fluoreno[4,3-b]benzofuran-10-amine Compound D: 8-(4-(4,6-di(naphthalen-2-yl)-1,3,5-triazin-2-yl)phenyl)quinoline Examples 2 to 10 and Comparative Examples 1 to 4

Organic light emitting diodes according to Examples 2 to 10 and Comparative Examples 1 to 4 were produced according to the same method as Example 1 except that the light emitting layer host was changed as shown in Tables 1 to 4.

Evaluation: Measurement of Driving Voltage, Current Efficiency, and Life-span Characteristics Driving voltages, current efficiency, life-span characteristics of the organic light emitting diodes according to Examples 1 to 10 and Comparative Examples 1 to 4 were evaluated. Specific measurement methods thereof are as follows, and the results are shown in Tables 1 to 4.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Current Efficiency

Current efficiency (cd/A) at the same current density (10 mA/$cm^2$) were calculated by using the luminance, current density, and voltages (V) from the items (1) and (2).

(4) Measurement of Driving Voltage

A driving voltage of each diode was measured using a current-voltage meter (Keithley 2400) at 15 mA/$cm^2$.

(5) Measurement of Life-span

T97 life-spans of the organic light emitting diodes according to Examples 1 to 10, and Comparative Examples 1 to 4 were measured as a time when their luminance decreased down to 97% relative to the initial luminance (cd/$m^2$) after emitting light with 9000 cd/$m^2$ as the initial luminance (cd/$m^2$) and measuring their luminance decrease depending on a time with a Polanonix life-span measurement system.

(6) Calculation of T97 Life-span Ratio (%)

T97 life-span ratio (%) is a relative value of T97(h).

T97 life-span ratio (%)={[T97(h) of Example]/{[T97(h) of Comparative Example]}×100

(7) Calculation of Driving Voltage Ratio (%)

Driving voltage ratio (%) is a relative value of the driving voltage (V).

Driving voltage ratio (%)={[driving voltage (V) of Example]/{[driving voltage (V) of Comparative Example]}×100

(8) Calculation of Current Efficiency Ratio (%)

Current Efficiency Ratio (%) is a relative value of the current efficiency (Cd/A).

Current efficiency ratio (%)={[current efficiency (Cd/A) of Example]/{[current efficiency (Cd/A) of Comparative Example]}×100

TABLE 1

| No. | Light emitting host | Driving voltage ratio (%) | Current efficiency ratio (%) | T97 life-span ratio (%) |
|---|---|---|---|---|
| Example 1 | Compound A-6 | 96 | 105 | 102 |
| Example 2 | Compound A-5 | 92 | 115 | 118 |
| Comparative Example 1 | Compound C-1 | 100 | 100 | 100 |

TABLE 2

| No. | Light emitting host | Driving voltage ratio (%) | Current efficiency ratio (%) | T97 life-span ratio (%) |
|---|---|---|---|---|
| Example 3 | Compound A-6 | 100 | 102 | 160 |
| Example 4 | Compound A-7 | 98 | 105 | 148 |
| Example 5 | Compound A-5 | 96 | 112 | 185 |
| Comparative Example 2 | Compound C-2 | 100 | 100 | 100 |

TABLE 3

| No. | Co-deposited host (Mixing weight ratio = 5:5) | Driving voltage ratio (%) | Current efficiency ratio (%) | T97 life-span ratio (%) |
|---|---|---|---|---|
| Comparative Example 3 | C-1:B-34 | 100 | 100 | 100 |
| Example 6 | A-6:B-34 | 96 | 105 | 102 |
| Example 7 | A-5:B-34 | 89 | 122 | 128 |

TABLE 4

| No. | Co-deposited host (Mixing weight ratio = 5:5) | Driving voltage ratio (%) | Current efficiency ratio (%) | T97 life-span ratio (%) |
|---|---|---|---|---|
| Comparative Example 4 | C-2:B-34 | 100 | 100 | 100 |
| Example 8 | A-6:B-34 | 100 | 103 | 144 |
| Example 9 | A-7:B-34 | 98 | 107 | 133 |
| Example 10 | A-5:B-34 | 93 | 119 | 180 |

Referring to Tables 1 to 4, the compounds according to the present invention exhibited greatly improved current efficiency and life-span characteristics compared with the compounds according to comparative examples.

Compared with Compound C-1, the compounds according to the present invention maintained similar life-span characteristics but exhibited greatly improved current efficiency and driving voltage, and compared with Compound C-2, the compounds according to the present invention maintained driving similar voltage characteristics and exhibited greatly improved current efficiency and life-span. The compounds according to an embodiment of the present invention exhibited all improved driving, efficiency, and life-span characteristics, compared with the compounds according to the comparative examples, and thus were optimized in all terms.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims.

DESCRIPTION OF SYMBOLS

100, 200: organic light emitting diode
105: organic layer
110: cathode
120: anode
130: light emitting layer
140: hole auxiliary layer

The invention claimed is:

1. A composition for an organic optoelectronic device, the composition comprising:

a first compound for an organic optoelectronic device represented by Chemical Formula 1a-2-1, and a second compound for an organic optoelectronic device represented by Chemical Formula 4C:

[Chemical Formula 1a-2-1]

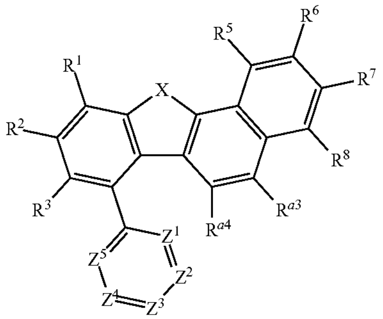

[Chemical Formula 1e-2-1]

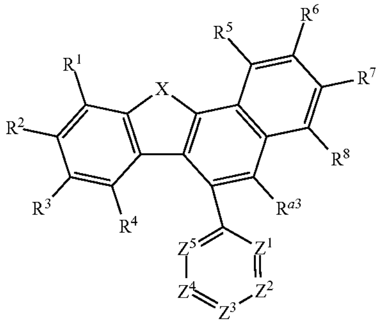

wherein, in Chemical Formula 1a-2-1,

X is O or S, $R^{a3}$, $R^{a4}$, $R^1$ to $R^3$, and $R^5$ to $R^8$ are independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof, $Z^1$ to $Z^5$ are independently N or C—$R^b$, at least one of Z to $Z^5$ is N, $R^b$ is independently hydrogen, deuterium, a substituted or unsubstituted C1 to C20 alkyl group, a substituted or unsubstituted C6 to C30 aryl group, or a combination thereof, the moiety represented by

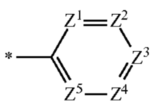

is a group of Group I, and

[Group I]

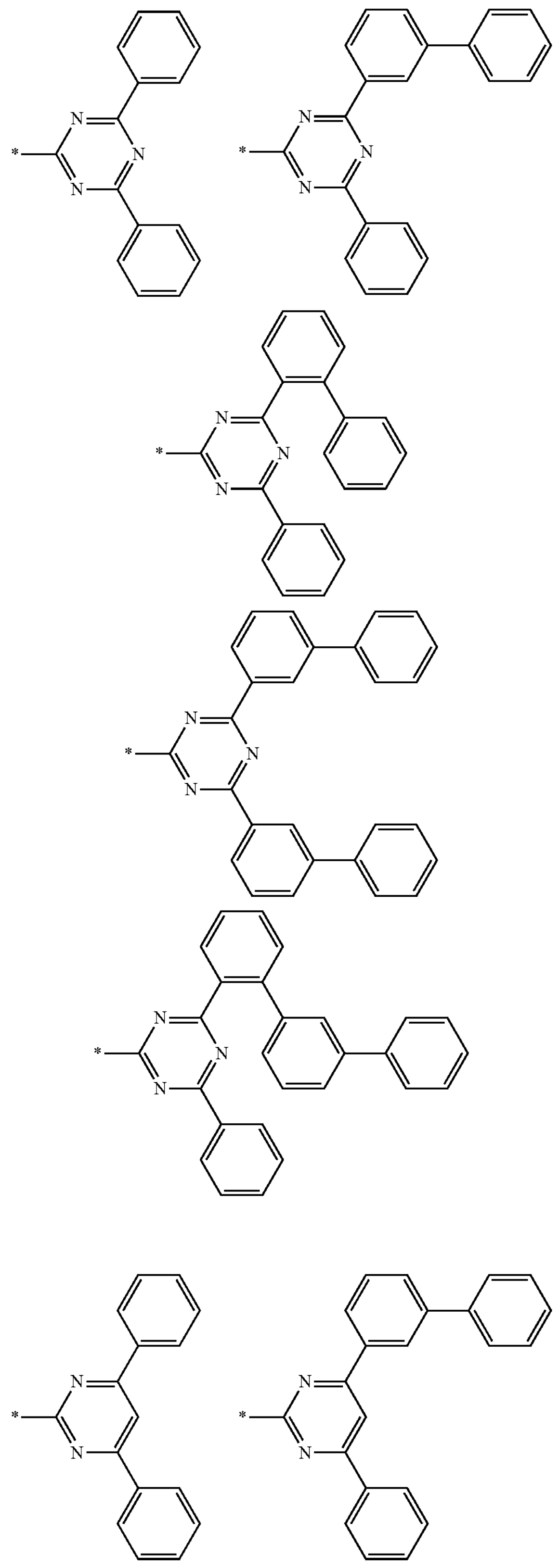

-continued
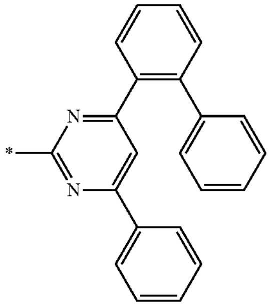
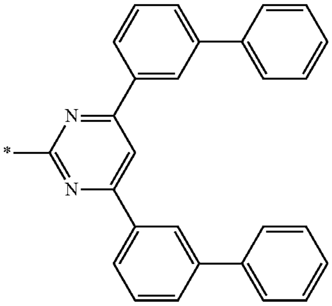
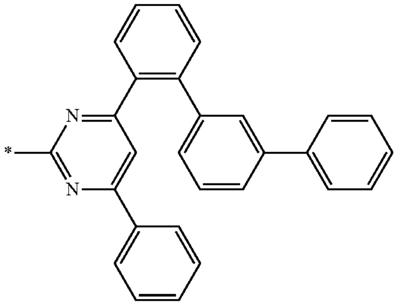
-continued
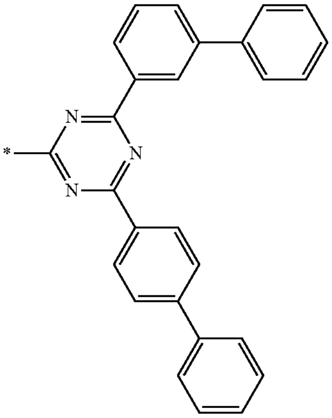
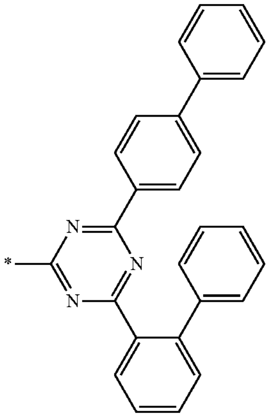
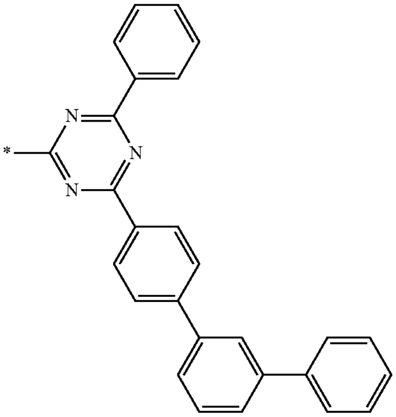
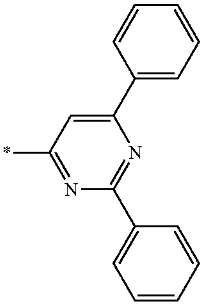
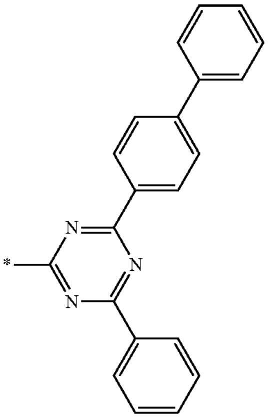
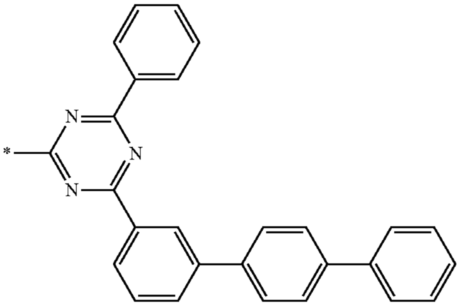

-continued
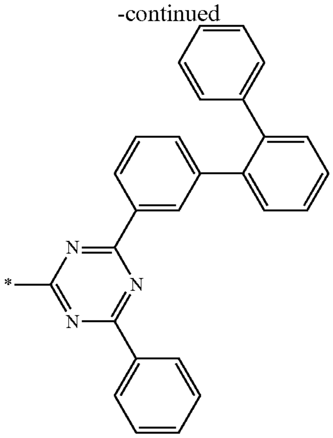
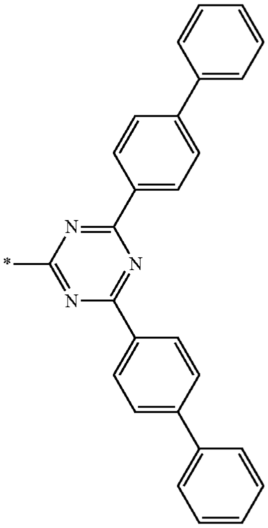
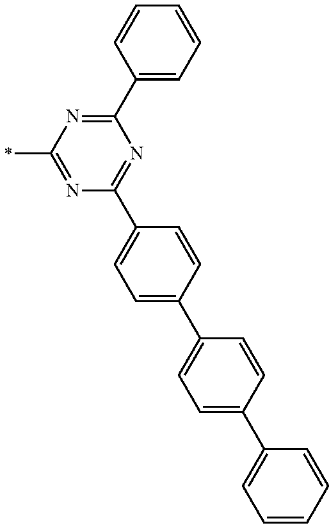
-continued
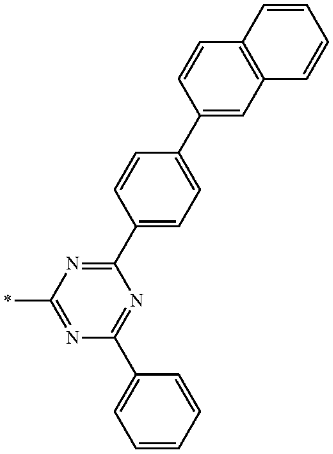
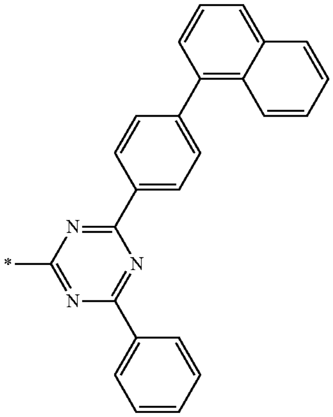
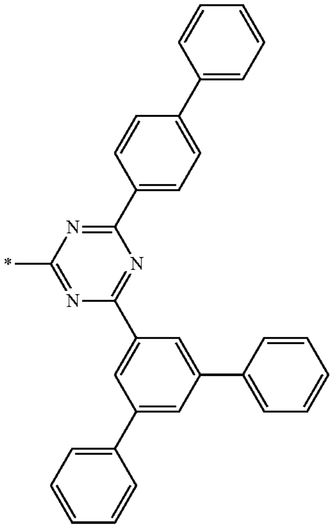

-continued
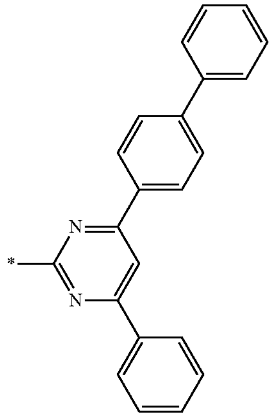
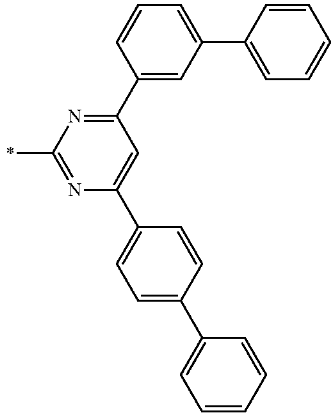
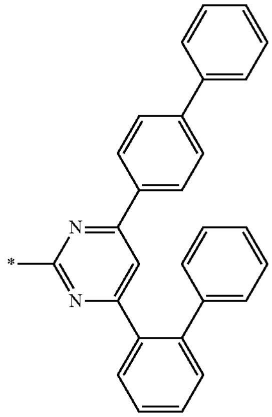
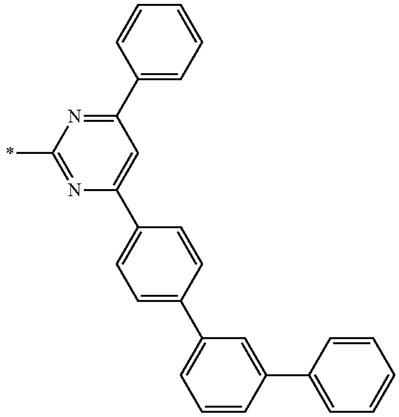
-continued
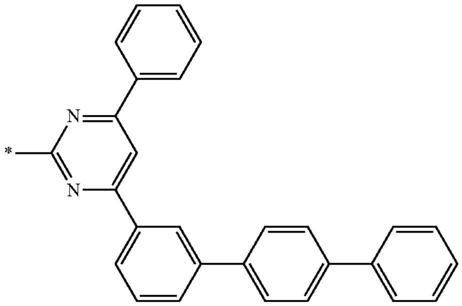
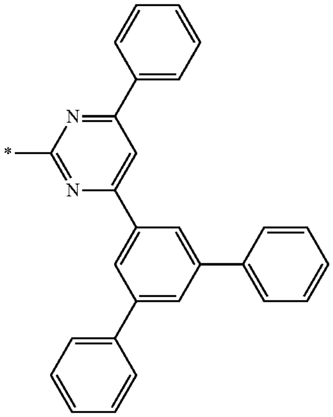
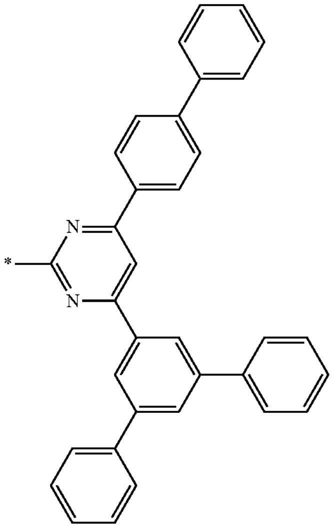
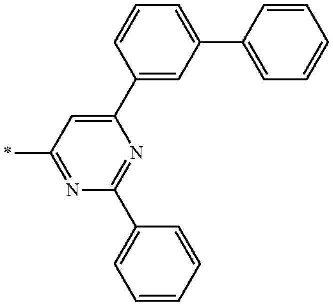

-continued
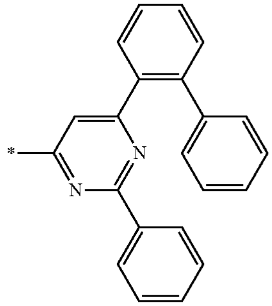
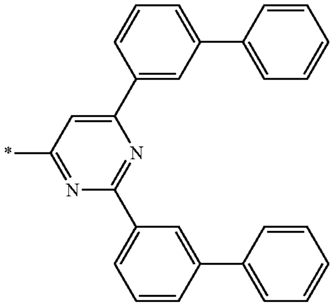
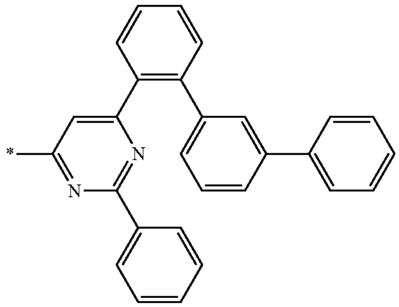
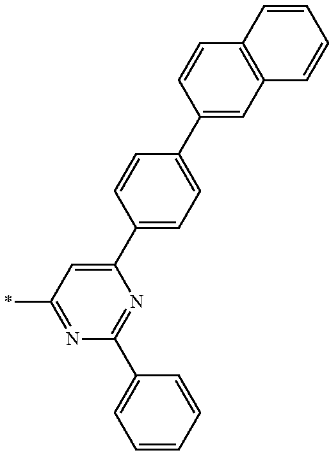
-continued
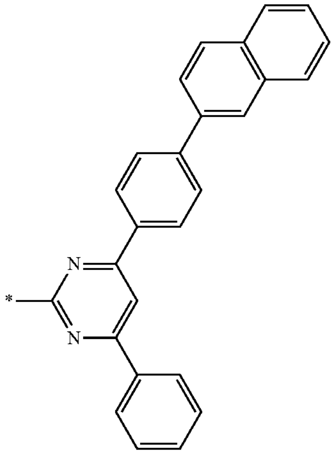
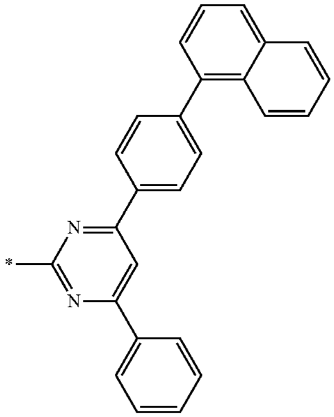
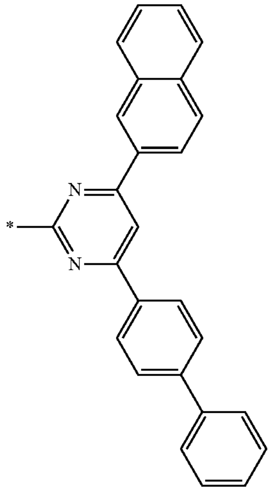

-continued
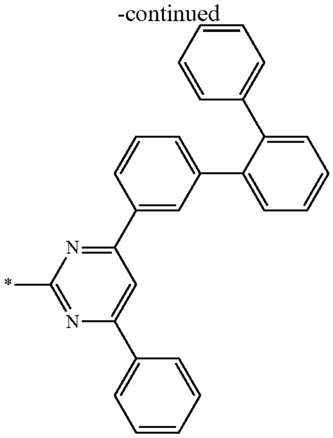
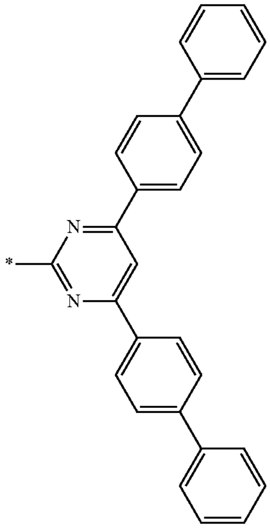
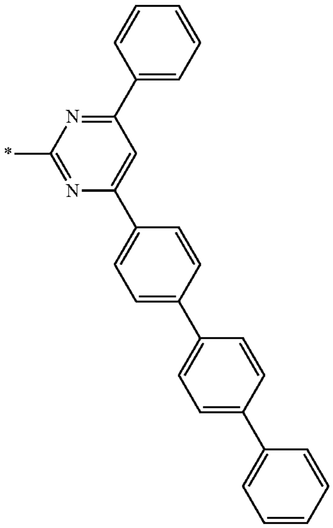
-continued
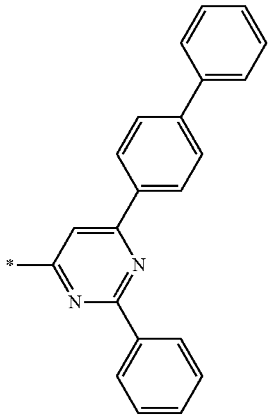
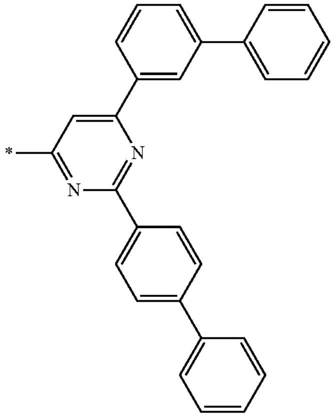
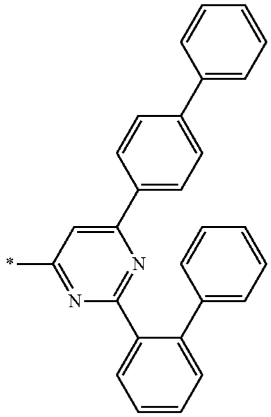
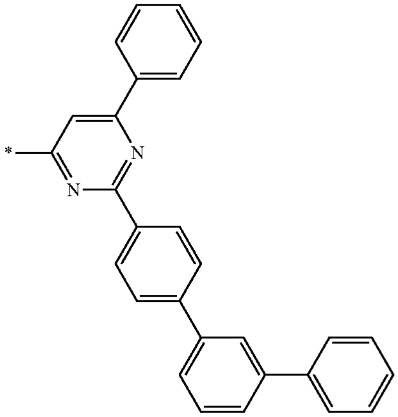

-continued

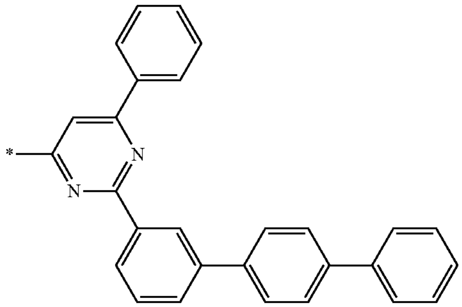

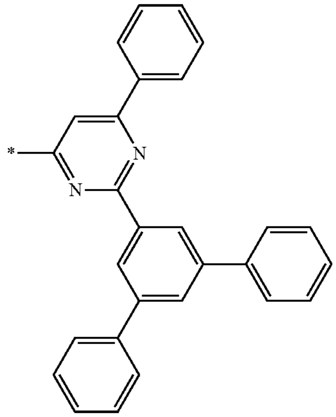

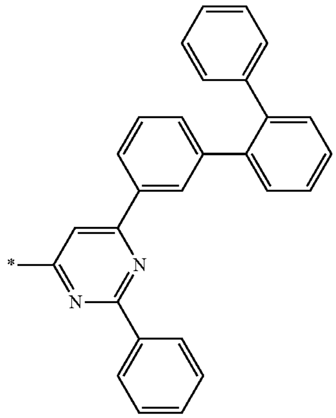

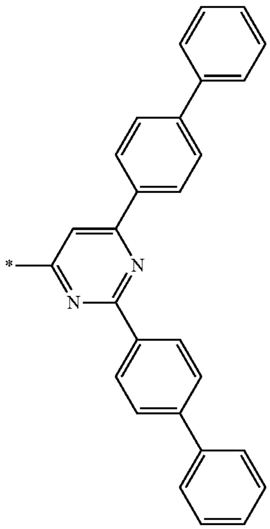

-continued

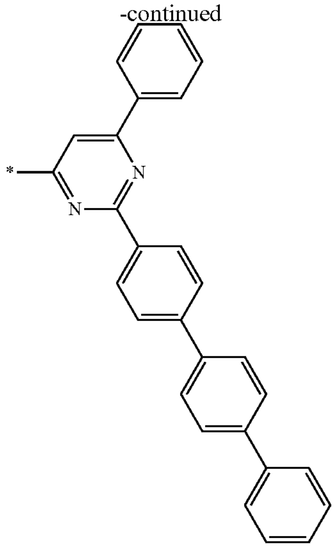

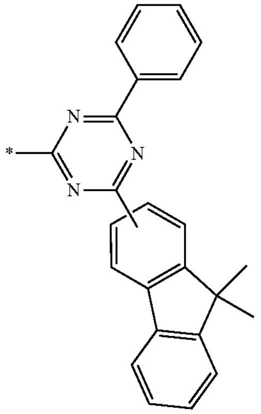

the "substituted" of Chemical Formula 1a-2-1 refers to replacement of at least one hydrogen by deuterium, a cyano group, a C1 to C10 alkyl group, or a C6 to C20 aryl group; and

[Chemical Formula 4C]

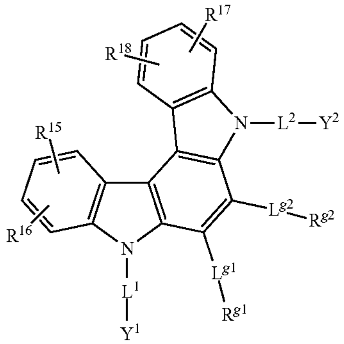

wherein, in Chemical Formula 4C, $Y^1$ and $Y^2$ are independently a substituted or unsubstituted C6 to C20 aryl group or a substituted or unsubstituted C2 to C30 heterocyclic group, provided that at least one of $Y^1$ and $Y^2$ is a substituted or unsubstituted naphthyl group, $Lg^1$, $Lg^2$, $L^1$, and $L^2$ are independently a single bond or a substituted or unsubstituted C6 to C20 arylene group, $Rg^1$, $Rg^2$, and $R^{15}$ to $R^{18}$ are independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, and the "substituted" of Chemical Formula 4C refers to replacement of at least one hydrogen by deuterium, a cyano group, a C1 to C5 alkyl group, or a C6 to C18 aryl group.

2. The composition for an organic optoelectronic device of claim 1, wherein the first compound is a compound of Group 1:

[Group 1]

[A-5]

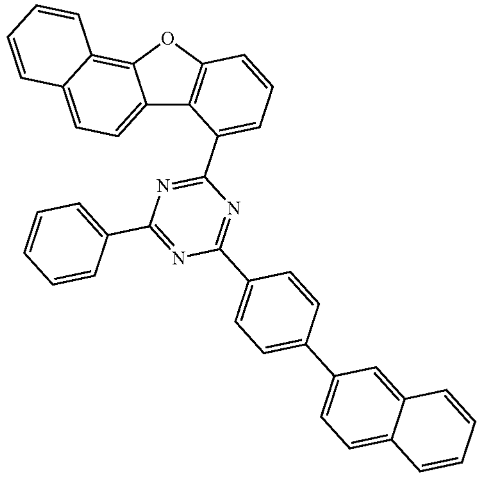

[A-6]

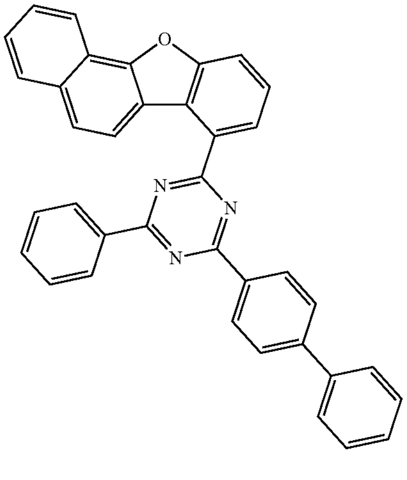

-continued

[A-7]

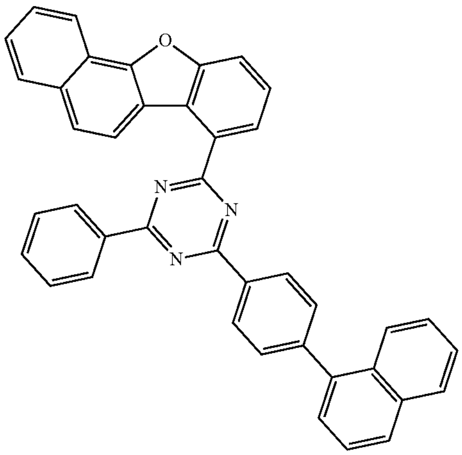

[A-11]

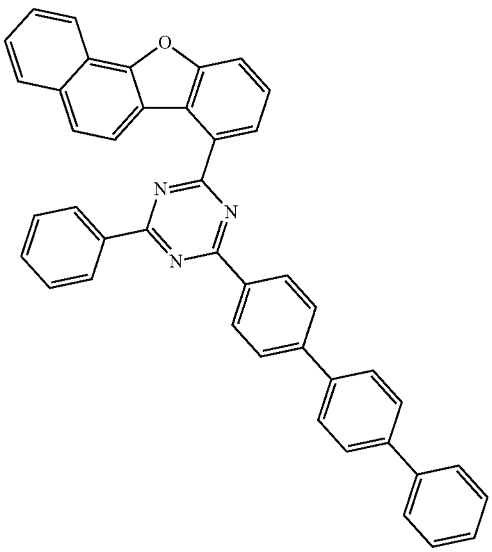

[A-12]

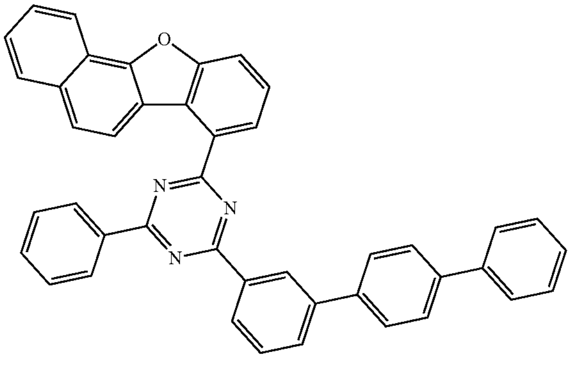

-continued
[A-13]
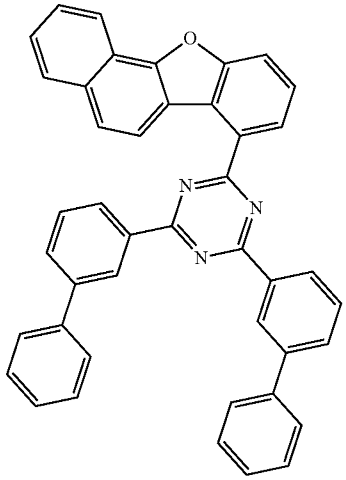
[A-15]
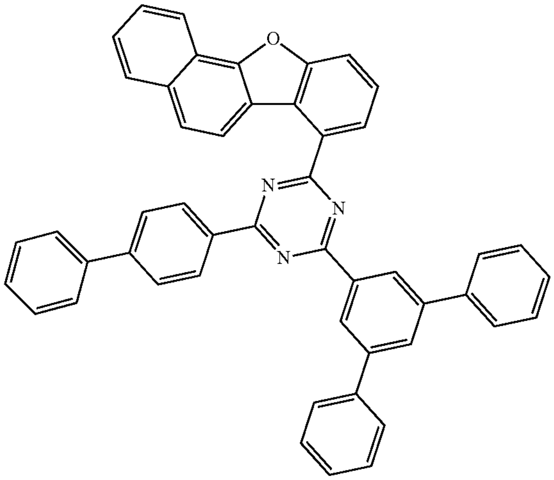
[A-16]
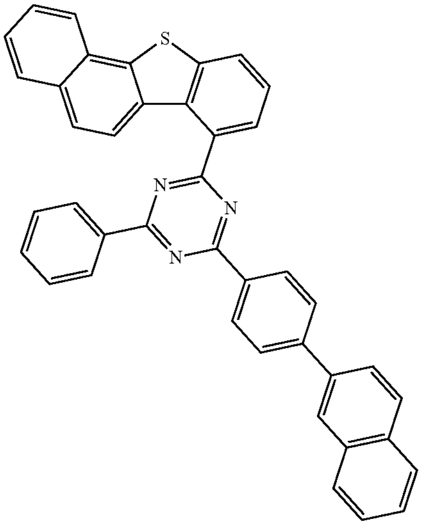
-continued
[A-19]
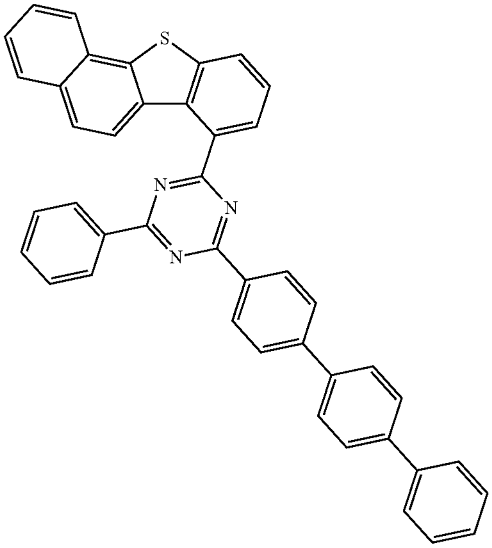
[A-25]
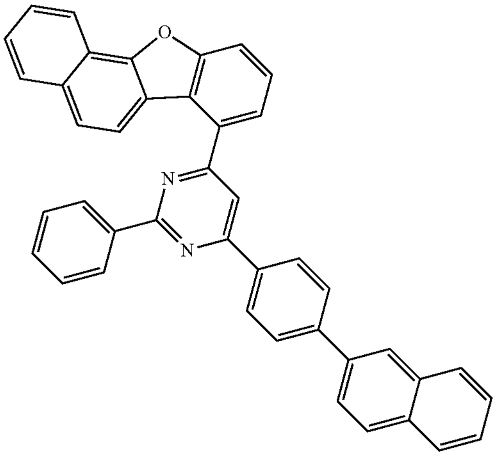
[A-26]
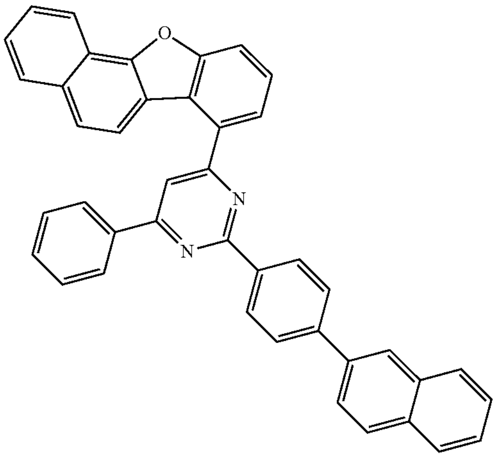

-continued
[A-27]
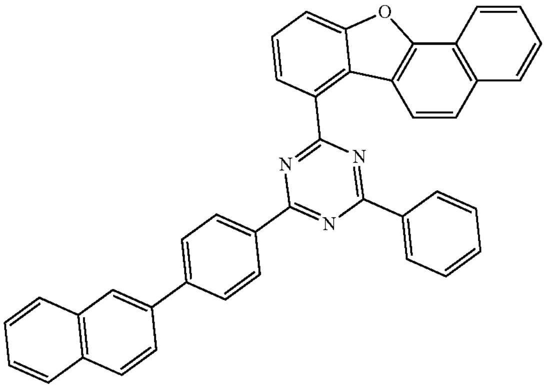
[A-63]
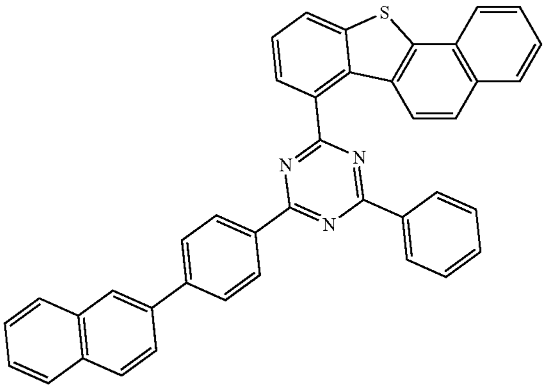
[A-99]
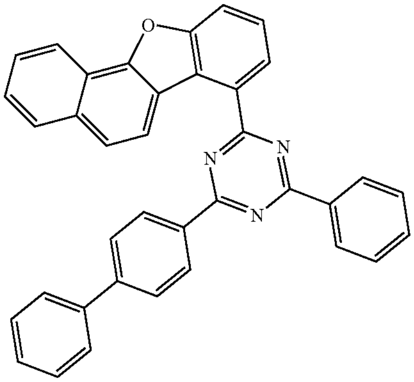
[A-100]
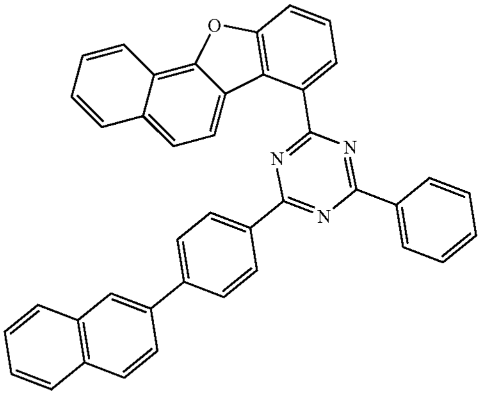
-continued
[A-101]
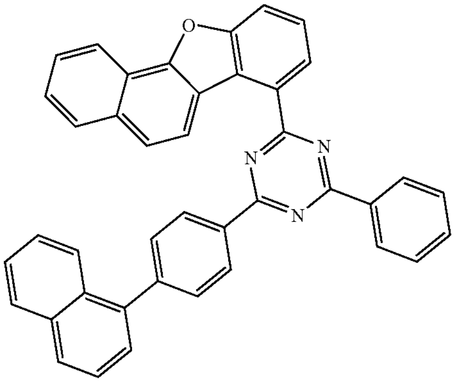
[A-102]
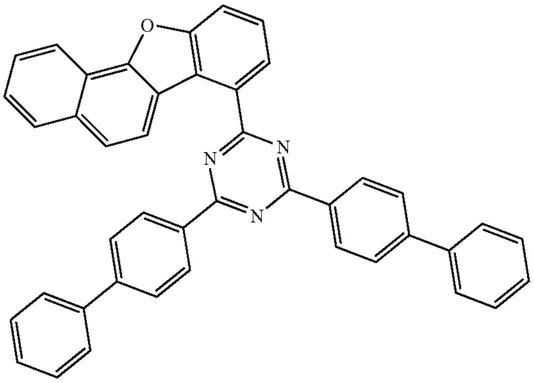
[A-117]
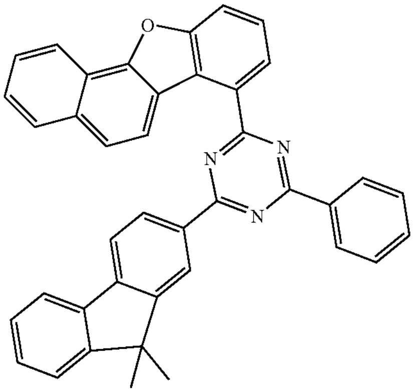
[A-119]
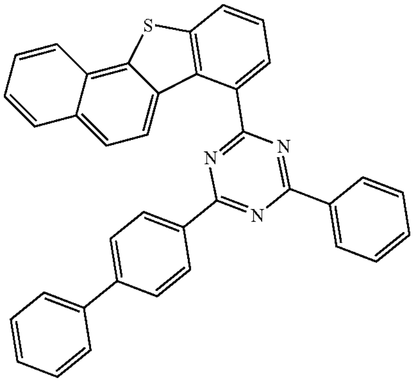

-continued
[A-120]
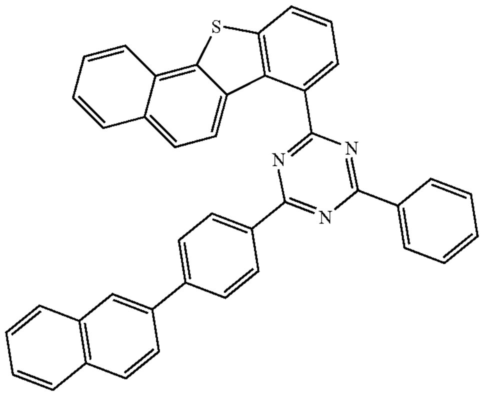
[A-121]
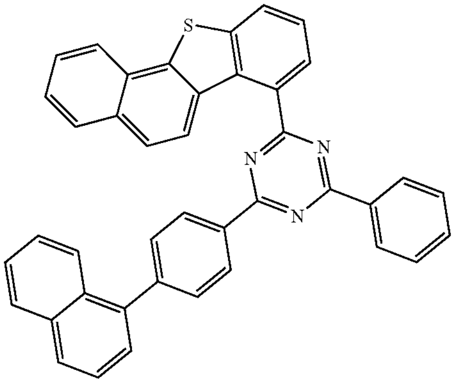
[A-122]
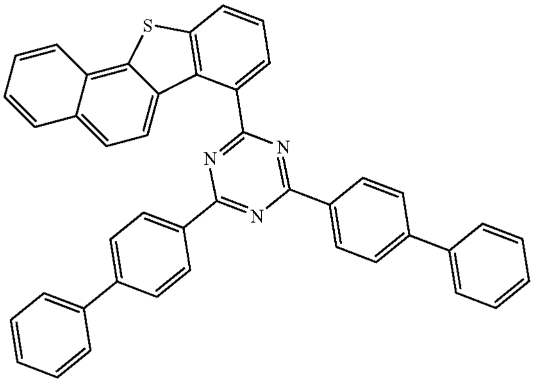
[A-137]
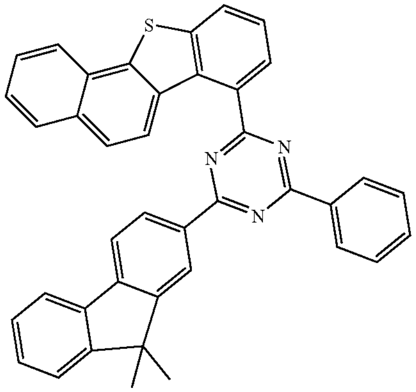
-continued
[A-139]
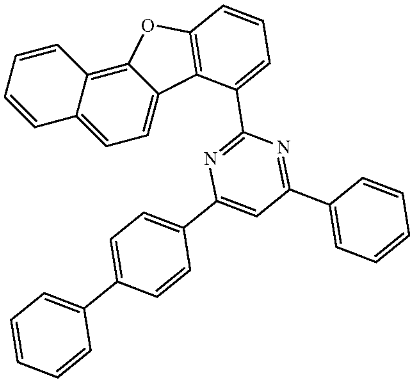
[A-140]
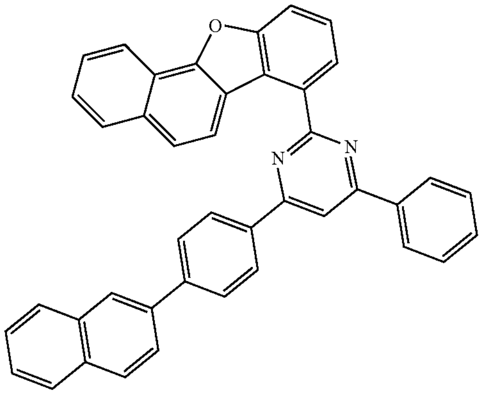
[A-141]
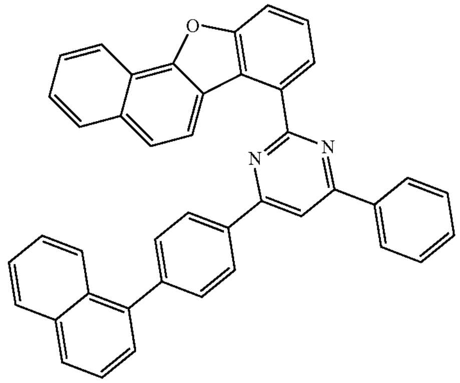
[A-142]
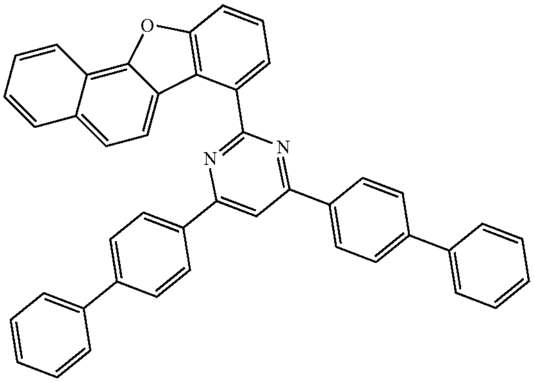

-continued

[A-143]

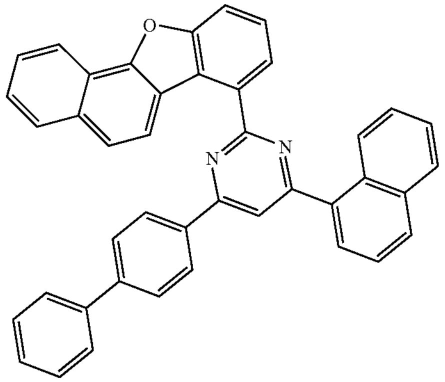

[A-144]

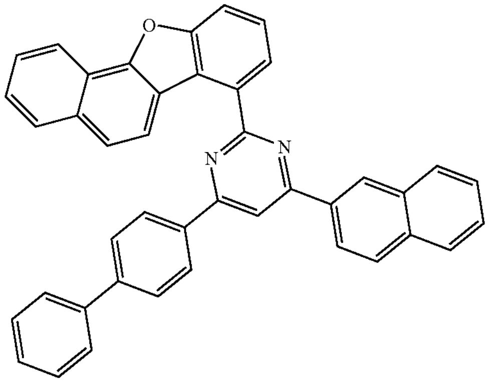

.

3. The composition for an organic optoelectronic device of claim 1, wherein, in Chemical Formula 4C:

$Y^1$ and $Y^2$ are independently a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, provided that at least one of $Y^1$ and $Y^2$ is a substituted or unsubstituted naphthyl group, and $R^{g1}$, $R^{g2}$, and $R^{15}$ to $R^{18}$ are independently hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

4. A organic optoelectronic device, comprising:

an anode and a cathode facing each other, and at least one organic layer disposed between the anode and the cathode, wherein the at least one organic layer comprises the composition for an organic optoelectronic device of claim 1.

5. The organic optoelectronic device of claim 4, wherein:

the at least one organic layer comprises a light emitting layer, and the light emitting layer comprises the composition for an organic optoelectronic device.

6. A display device comprising the organic optoelectronic device of claim 4.

* * * * *